(12) United States Patent
Caruso et al.

(10) Patent No.: US 8,623,876 B2
(45) Date of Patent: Jan. 7, 2014

(54) SUBSTITUTED PYRROLO-PYRAZOLE DERIVATIVES AS KINASE INHIBITORS

(75) Inventors: Michele Caruso, Milan (IT); Italo Beria, Nerviano (IT); Maria Gabriella Brasca, Cusago (IT); Ron Ferguson, Casale Litta (IT); Helena Posteri, Travedona Monate (IT)

(73) Assignee: Nerviano Medical Sciences S.R.L., Nerviano (MI) (IT)

( * ) Notice: Subject to any disclaimer, the term of this patent is extended or adjusted under 35 U.S.C. 154(b) by 51 days.

(21) Appl. No.: 13/495,688

(22) Filed: Jun. 13, 2012

(65) Prior Publication Data

US 2012/0277248 A1    Nov. 1, 2012

Related U.S. Application Data

(62) Division of application No. 12/444,792, filed as application No. PCT/EP2007/060685 on Oct. 9, 2007, now Pat. No. 8,227,472.

(30) Foreign Application Priority Data

Oct. 11, 2006   (EP) .................................... 06122136

(51) Int. Cl.
| | | |
|---|---|---|
| *A61K 31/497* | (2006.01) | |
| *A01N 43/40* | (2006.01) | |
| *A61K 31/445* | (2006.01) | |
| *A01N 43/56* | (2006.01) | |
| *A61K 31/415* | (2006.01) | |
| *C07D 211/32* | (2006.01) | |
| *C07D 231/54* | (2006.01) | |
| *C07D 487/02* | (2006.01) | |

(52) U.S. Cl.
USPC ...... 514/254.06; 514/322; 514/407; 546/199; 548/360.5

(58) Field of Classification Search
USPC .................... 514/254.06, 322, 407; 546/199; 548/360.5
See application file for complete search history.

(56) References Cited

U.S. PATENT DOCUMENTS 7,407,971 B2    8/2008   Brasca et al.

FOREIGN PATENT DOCUMENTS

| WO | 02/12242 | 2/2002 |
| WO | 2004/056827 | 7/2004 |

OTHER PUBLICATIONS

International Search Report mailed Jul. 2, 2008 in related International Publication No. PCT/EP2007/060685.
Vippagunta et al. Advanced Drug Delivery Reviews, 2001, vol. 48, pp. 3-26.
U.S. Official Action mailed Oct. 20, 2011 in related U.S. Appl. No. 12/444,792.

*Primary Examiner* — Samira Jean-Louis
(74) *Attorney, Agent, or Firm* — Scully, Scott, Murphy & Presser, P.C.

(57) ABSTRACT

Substituted pyrrolo-pyrazole derivatives of formula (I) and pharmaceutically acceptable salts thereof, as defined in the specification, process for their preparation and pharmaceutical compositions comprising them are disclosed; the compounds of the invention may be useful in therapy in the treatment of diseases associated with dysregulated protein kinase activity, like cancer.

4 Claims, No Drawings

SUBSTITUTED PYRROLO-PYRAZOLE DERIVATIVES AS KINASE INHIBITORS

This application is a divisional of U.S. patent application Ser. No. 12/444,792 filed on Apr. 8, 2009, which is a National Stage Entry of PCT/EP2007/060685 filed on Oct. 9, 2007, and claims the benefit of EP Patent Application No. 06122136.2 filed on Oct. 11, 2006, the entire contents of each of which are incorporated herein by reference.

The present invention relates to certain substituted pyrrolo-pyrazole compounds, which modulate the activity of protein kinases. The compounds of this invention are therefore useful in treating diseases caused by dysregulated protein kinase activity. The present invention also provides methods for preparing these compounds, pharmaceutical compositions comprising these compounds, and methods of treating diseases utilizing pharmaceutical compositions comprising these compounds.

The use of mitotic inhibitors in cancer therapy is a widely accepted clinical strategy for the treatment of a broad range of human cancers. Taxanes (Paclitaxel and Docetaxel) and Vinca Alkaloids (Vincristine and Vinblastine) work by either stabilizing or destabilizing microtubules with catastrophic consequences in cells progressing through mitosis. They are first line therapeutics for several tumour types and second line in cisplatin-refractory Ovarian, Breast, Lung, bladder and esophagus cancers (Taxanes). However, due to the role of microtubules in processes such as cell movement, phagocytosis and axonal transport certain toxicities such as peripheral neuropathy are frequently observed with these agents. Progression through mitosis is a requirement of all proliferating cells and hence cancer therapies that have targets in mitosis are generally applicable to a wide range of tumour types. Several protein kinases play key roles in the orchestration of the cell cycle and some of them are already subject to targeted therapies in the oncology setting including Cdk-2 and Aurora-A. The fidelity of mitosis is of paramount importance and several "checkpoints" exist in normal cells to maintain chromosome integrity during the cell cycle. These checkpoints often go away during oncogenic transformation and this permits cancer cells to tolerate anueploidy and chromosomal instability. Inhibition of mitosis in "checkpoint compromised" tumour cells should have catastrophic consequences as cancer cells try to carry forward an aberrant mitosis.

The Polo-like kinase family, comprising 4 serine/threonine kinases (Plk-1-4), are predominantly involved in the entry into, progression through and exit from mitosis. These kinases are characterized by having an n-terminal kinase domain and a unique, c-terminal, "Polo-Box" domain. This domain is responsible for targeting the kinase to various mitotic structures (centrosomes, kinetochores, spindle poles, midbody) and the temporal and spatial regulation of Plks are important for normal progression through mitosis (reviewed in van Vugt and Medema, Oncogene 2005, 24(17):2844-59; Barr et al, Nat Rev Mol Cell Biol. 2004, 5(6):429-40; Dai and Cogswell, Prog Cell Cycle Res. 2003, 5:327-34; Glover et al, Genes Dev. 1998, 12(24):3777-87). The most characterized member of the family is Plk-1 and its activity has been implicated in several processes during mitosis including the G2/M transition by regulating Cdk-1 activity in multiple ways (activation of Cdc25c, nuclear translocation of cyclin B, inactivation of Myt-1 and Wee-1) (Inoue et al, EMBO J. 2005, 24(5): 1057-67; van Vugt et al, J Biol Chem. 2004, 9(35):36841-54; Watanabe et al, Proc Natl Acad Sci U S A. 2004, 101(13): 4419-24 2004; Nakajima et al, J Biol Chem. 2003, 278(28): 25277-80; Toyoshima-Morimoto et al, J Biol Chem. 2002, 277(50):48884-8; Bartholomew et al, Mol Cell Biol., 2001 21(15):4949-59; Qian et al, Mol Biol Cell. 2001, 12(6):1791-9; Roshak et al, Cell Signal. 2000, 12(6):405-11); centrosome maturation and separation; regulation of chromosomal-arm cohesion at prophase and sister chromatid separation at metaphase/anaphase transition; activation of the Anaphase Promoting Complex to start mitotic exit; cytokinesis. Plk-1 is over-expressed in several tumour cells including breast, ovarian, non small cell lung, colon, head and neck, endometrial and esophageal carcinomas and its over-expression often correlates with poor prognosis.

Disruption of Plk-1 function by various means in tumoural cells (siRNA and antisense ablation, dominant negative proteins and immunodepletion) results in an aberrant mitosis followed by mitotic catastrophy whilst causing a "checkpoint-mediated" cell cycle arrest in normal cells. Thus, pharmacological attenuation of Plk-1 function may have a therapeutic benefit in the treatment of several diverse cancers.

SUMMARY OF THE INVENTION

Several heterocyclic compounds are known in the art as protein kinase inhibitors for the treatment of hyperproliferative diseases such as for the treatment of cancer. As an example, 2-carboxamido-pyrazoles and 2-ureido-pyrazoles, and derivatives thereof, have been disclosed as protein kinase inhibitors in the international patent applications WO 01/12189, WO 01/12188, WO 02/48114 and WO 02/70515 (Pfizer Italia Srl).

Fused bicyclic compounds comprising pyrazole moieties and possessing kinase inhibitory activity have been also disclosed in WO 00/69846, WO 02/12242, WO 03/28720 and WO04/56827 (Pfizer Italia Srl).

Some specific compounds of the aforementioned WO 02/12242 are excluded from the present general formula.

Despite these developments, there is still need for effective agents for said disease.

The present inventors have now discovered that compounds of formula (I), described below, are kinase inhibitors and are thus useful in therapy as antitumor agents and lack, in terms of both toxicity and side effects, the aforementioned drawbacks associated with currently available antitumor drugs.

Accordingly, a first object of the present invention is to provide a substituted pyrrolo-pyrazole compound represented by formula (I),

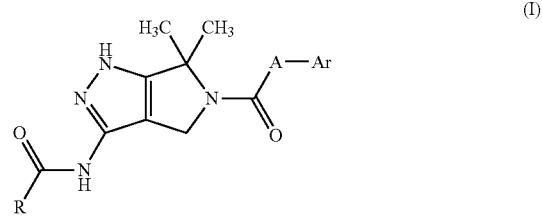

wherein
R is hydrogen or an optionally further substituted group selected from: saturated or unsaturated, straight or branched $C_1$-$C_6$ alkyl, $C_3$-$C_6$ cycloalkyl, heterocyclyl and aryl;
A is $CH_2$ or NH;
Ar is an optionally substituted aryl, provided that
when A is $CH_2$ and Ar is phenyl then R is other than 3-bromophenyl, 4-fluorophenyl, 4-tert-butylphenyl, cyclopropyl or 2-naphthyl and when A is CH₂ and Ar is thiophene then R is other than 3-bromophenyl, 4-fluorophenyl, 4-tert-butylphenyl, cyclopropyl, 2-naphthyl or benzyl; and isomers, tautomers, hydrates, solvates, complexes, metabolites, prodrugs, carriers, N-oxides and pharmaceutically acceptable salts thereof.

The present invention also provides methods of synthetizing the substituted pyrrolo pyrazole derivatives of formula (I) prepared through a process consisting of standard synthetic transformations.

The present invention also provides a method for treating diseases caused by and/or associated with dysregulated protein kinase activity, particularly PLK family, protein kinase C in different isoforms, Met, PAK-4, PAK-5, ZC-1, STLK-2, DDR-2, Aurora 1, Aurora 2, Bub-1, Chk1, Chk2, HER2, raf1, MEK1, MAPK, EGF-R, PDGF-R, FGF-R, IGF-R, PI3K, wee1 kinase, Src, Abl, Akt, MAPK, ILK, MK-2, IKK-2, Cdc7, Nek, Cdk/cyclin kinase family, more particularly PLK-1 and PLK-3, which comprises administering to a mammal in need thereof an effective amount of a substituted pyrrolo-pyrazole compound represented by formula (I) as defined above.

A preferred method of the present invention is to treat a disease caused by and/or associated with dysregulated protein kinase activity selected from the group consisting of cancer, cell proliferative disorders, viral infections, autoimmune and neurodegenerative disorders.

Another preferred method of the present invention is to treat specific types of cancer including but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocitic leukaemia, acute lymphoblastic leukaemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Another preferred method of the present invention is to treat specific cellular proliferation disorders such as, for example, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

Another preferred method of the present invention is to treat viral infections, in particular the prevention of AIDS development in HIV-infected individuals.

In addition, the method of the present invention also provides tumor angiogenesis and metastasis inhibition as well as the treatment of organ transplant rejection and host versus graft disease.

The present invention also provides a pharmaceutical composition comprising one or more compounds of formula (I) or a pharmaceutically acceptable salt thereof and a pharmaceutically acceptable excipient, carrier or diluent.

The present invention further provides a pharmaceutical composition comprising a compound of formula (I) in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

DETAILED DESCRIPTION OF THE INVENTION

Unless otherwise specified, when referring to the compounds of formula (I) per se as well as to any pharmaceutical composition thereof or to any therapeutic treatment comprising them, the present invention includes all of the hydrates, solvates, complexes, metabolites, prodrugs, carriers, N-oxides and pharmaceutically acceptable salts of the compounds of this invention.

A metabolite of a compound of formula (I) is any compound into which this same compound of formula (I) is converted in vivo, for instance upon administration to a mammal in need thereof. Typically, without however representing a limiting example, upon administration of a compound of formula (I), this same derivative may be converted into a variety of compounds, for instance including more soluble derivatives like hydroxylated derivatives, which are easy to be excreted. Hence, depending upon the metabolic pathway thus occurring, any of these hydroxylated derivatives may be regarded as a metabolite of the compounds of formula (I).

Prodrugs are any covalently bonded compounds, which release in vivo the active parent drug according to formula (I).

N-Oxides are compounds of formula (I) wherein nitrogen and oxygen are tethered through a dative bond.

If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form.

In addition to the above, as known to those skilled in the art, the unsubstituted nitrogen on the pyrazole ring of the compounds of formula (I) rapidly equilibrates in solution to form a mixture of tautomers, as depicted below:

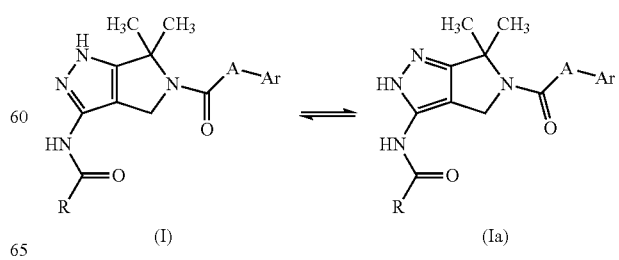

wherein R, A and Ar are as defined above.

Accordingly, in the present invention, where only one tautomer is indicated for the compounds of formula (I), the other tautomer (Ia) is also within the scope of the present invention, unless specifically noted otherwise.

In the present description, unless otherwise specified, with the term "straight or branched $C_1$-$C_6$ alkyl", hence comprehensive of $C_1$-$C_4$ alkyl, we intend any of the groups such as, for instance, methyl, ethyl, n-propyl, isopropyl, n-butyl, isobutyl, tert-butyl, sec-butyl, n-pentyl, n-hexyl, and the like.

With the term "$C_3$-$C_6$ cycloalkyl" we intend, unless otherwise provided, 3- to 6-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene and cyclohexadiene.

With the term "heterocyclyl" (also known as "heterocycloalkyl") we intend a 3- to 7-membered, saturated or partially unsaturated carbocyclic ring where one or more carbon atoms are replaced by heteroatoms such as nitrogen, oxygen and sulfur. Not limiting examples of heterocyclyl groups are, for instance, pyran, pyrrolidine, pyrroline, imidazo line, imidazolidine, pyrazolidine, pyrazoline, thiazoline, thiazolidine, dihydrofuran, tetrahydrofuran, 1,3-dioxolane, piperidine, piperazine, morpholine and the like.

With the term "aryl" we intend carbocyclic or heterocyclic with from 1 to 2 ring moieties, either fused or linked to each other by single bonds, wherein at least one of the rings is aromatic; if present, any aromatic heterocyclic ring also referred to as heteroaryl group, comprises a 5 to 6 membered ring with from 1 to 3 heteroatoms selected among N, NH, O or S. Examples of aryl groups according to the invention are, for instance, phenyl, biphenyl, α- or β-naphthyl, dihydronaphthyl, thienyl, benzothienyl, furyl, benzofuranyl, pyrrolyl, imidazolyl, pyrazolyl, thiazolyl, isothiazolyl, oxazolyl, isoxazolyl, pyridyl, pyrazinyl, pyrimidinyl, pyridazinyl, indolyl, isoindolyl, purinyl, quinolyl, isoquinolyl, dihydroquinolinyl, quinoxalinyl, benzodioxolyl, indanyl, indenyl, triazolyl, and the like.

According to the present invention and unless otherwise provided, the above R group may be optionally substituted, in any of their free positions, by one or more groups, for instance 1 to 6 groups, independently selected from: halogen, nitro, oxo groups (=O), cyano, $C_1$-$C_6$ alkyl, polyfluorinated alkyl, polyfluorinated alkoxy, alkenyl, alkynyl, hydroxyalkyl, aryl, arylalkyl, heterocyclyl, cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cyclo alkyloxycarbonyl, heterocyclyloxycarbonyl, amino, ureido, alkylamino, dialkylamino, arylamino, diarylamino, heterocyclyamino, formylamino, alkylcarbonylamino, arylcarbonylamino, heterocyclcarbonylamino, aminocarbonyl, alkylamino carbonyl, dialkylaminocarbonyl, arylamino carbonyl, heterocyclylaminocarbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio phosphonate and alkylphosphonate. In their turn, whenever appropriate, each of the above substituent may be further substituted by one or more of the aforementioned groups.

In this respect, with the term halogen atom we intend a fluorine, chlorine, bromine or iodine atom.

With the term alkenyl or alkynyl we intend any of the aforementioned straight or branched $C_2$-$C_6$ alkyl groups further bearing a double or triple bond. Non limiting examples of alkenyl or alkynyl groups of the invention are, for instance, vinyl, allyl, 1-propenyl, isopropenyl, 1-butenyl, 2-butenyl, 3-butenyl, 2-pentenyl, 1-hexenyl, ethynyl, 2-propynyl, 4-pentynyl, and the like.

With the term polyfluorinated alkyl or alkoxy we intend any of the above straight or branched $C_1$-$C_6$ alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the term alkoxy, aryloxy, heterocyclyloxy and derivatives thereof we intend any of the above $C_1$-$C_6$ alkyl, aryl or heterocyclyl groups linked to the rest of the molecule through a oxygen atom (—O—).

From all of the above, it is clear to the skilled person that any group which name is a composite name such as, for instance, cycloalkylalkyl, arylalkyl, heterocyclylalkyl, alkoxy, alkylthio, aryloxy, arylalkyloxy, alkylcarbonyloxy and the like, have to be intended as conventionally construed by the parts from which they derive. As an example, a group such as heterocyclylalkyloxy is an alkoxy group, e.g. alkyloxy, wherein the alkyl moiety is further substituted by a heterocyclyl group, and wherein $C_1$-$C_6$ alkyl and heterocyclyl are as above defined.

Pharmaceutically acceptable salts of the compounds of formula (I) include the acid addition salts with inorganic or organic acids, e.g., nitric, hydrochloric, hydrobromic, sulfuric, perchloric, phosphoric, acetic, trifluoroacetic, propionic, glycolic, lactic, oxalic, malonic, malic, maleic, tartaric, citric, benzoic, cinnamic, mandelic, methanesulphonic, isethionic and salicylic acid. Preferably, the acid addition salt of the compounds of the invention is selected between the hydrochloride or mesylate salt.

Pharmaceutically acceptable salts of the compounds of formula (I) also include the salts with inorganic or organic bases, e.g., alkali or alkaline-earth metals, especially sodium, potassium, calcium or magnesium hydroxides, carbonates or bicarbonates, acyclic or cyclic amines, preferably methylamine, ethylamine, diethylamine, triethylamine, piperidine and the like.

A preferred class of compounds of formula (I) are the compounds wherein:

R is a $C_1$-$C_6$ alkyl substituted by heterocyclyl or aryl, or an optionally further substituted heterocyclyl or aryl.

Another preferred class of compounds of formula (I) are the compounds wherein:

R is heterocyclylmethyl, arylmethyl, or an optionally further substituted heterocyclyl or aryl;

Ar is an optionally substituted phenyl, thienyl or furyl.

A further preferred class of compounds of formula (I) are the compounds wherein:

R is an optionally further substituted heterocyclyl or aryl.

A particularly preferred class of compounds of formula (I) are the compounds wherein:

Ar is a group selected from:

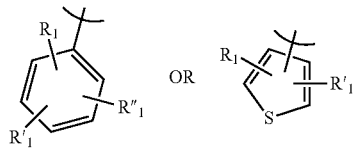

wherein $R_1$, $R'_1$ and $R''_1$ are independently hydrogen, halogen, nitro, oxo groups (=O), cyano, $C_1$-$C_6$ alkyl, polyfluorinated alkyl, polyfluorinated alkoxy, hydroxyalkyl, hydroxy, alkoxy, alkylcarbonyloxy, carboxy, alkoxycarbonyl, aryloxycarbonyl, amino, ureido, alkylamino, dialkylamino, alkylcarbonylamino, heterocyclylcarbonylamino, alkylsulfonylamino, alkylcarbonyl, aminocarbonyl, alkylaminocarbonyl, alkylsulfonyl, aminosulfonyl, and alkylthio.

A most preferred class of compounds of formula (I) are compounds wherein:

Ar is a group of formula

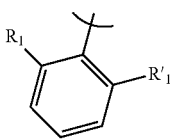

wherein $R_1$ and $R'_1$ are as defined above.

Another most preferred class of compounds of formula (I) are compounds wherein:

R is a group selected from:

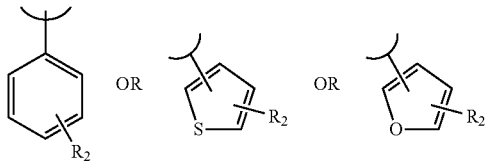

wherein $R_2$ is selected from: $C_1$-$C_6$ alkyl, halogen, nitro, oxo groups (=O), cyano, polyfluorinated alkyl, polyfluorinated alkoxy, alkenyl, alkynyl, hydroxyalkyl, aryl, arylalkyl, heterocyclyl, cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylamino carbonyl, dialkylaminocarbonyl, arylaminocarbonyl, heterocyclylaminocarbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio phosphonate and alkylphosphonate.

Ar is a group of formula:

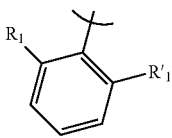

wherein $R_1$ and $R'_1$ are as defined above.

Specific compounds of the invention are listed below (for the meaning of the codes, see the Examples section):

N-(2,6-dichlorophenyl)-6,6-dimethyl-3-{[4-(4-methylpiperazin-1-yl)benzoyl]amino}-2,6-dihydropyrrolo[3,4-c]pyrazole-5(4H)-carboxamide (A1-Z-B1);

N-[6,6-dimethyl-5-(phenylacetyl)-2,4,5,6-tetrahydropyrrolo[3,4-c]pyrazol-3-yl]-4-(4-methylpiperazin-1-yl)benzamide (A1-Z-B2);

N-(2,6-difluorophenyl)-6,6-dimethyl-3-{[4-(4-methylpiperazin-1-yl)benzoyl]amino}-2,6-dihydropyrrolo[3,4-c]pyrazole-5(4H)-carboxamide (A1-Z-B3);

N-{5-[(3,5-difluorophenyl)acetyl]-6,6-dimethyl-2,4,5,6-tetrahydropyrrolo[3,4-c]pyrazol-3-yl}-4-(4-methylpiperazin-1-yl)benzamide (A1-Z-B4);

N-{5-[(2,6-difluorophenyl)acetyl]-6,6-dimethyl-2,4,5,6-tetrahydropyrrolo[3,4-c]pyrazol-3-yl}-4-(4-methylpiperazin-1-yl)benzamide (A1-Z-B5);

N-(2,6-dichlorophenyl)-6,6-dimethyl-3-{[3-(4-methylpiperazin-1-yl)benzoyl]amino}-2,6-dihydropyrrolo[3,4-c]pyrazole-5(4H)-carboxamide (A2-Z-B1);

N-{5-[(2,6-dichlorophenyl)acetyl]-6,6-dimethyl-1,4,5,6-tetrahydropyrrolo[3,4-c]pyrazol-3-yl}-4-(4-methylpiperazin-1-yl)benzamide (A1-Z-B7);

N-{6,6-dimethyl-5-[(2-nitrophenyl)acetyl]-1,4,5,6-tetrahydropyrrolo[3,4-c]pyrazol-3-yl}-4-(4-methylpiperazin-1-yl)benzamide (A1-Z-B9);

N-{5-[(2-methoxyphenyl)acetyl]-6,6-dimethyl-1,4,5,6-tetrahydropyrrolo[3,4-c]pyrazol-3-yl}-4-(4-methylpiperazin-1-yl)benzamide (A1-Z-B15);

N-{5-[(3-chlorophenyl)acetyl]-6,6-dimethyl-1,4,5,6-tetrahydropyrrolo[3,4-c]pyrazol-3-yl}-4-(4-methylpiperazin-1-yl)benzamide (A1-Z-B19);

N-{5-[(3-methoxyphenyl)acetyl]-6,6-dimethyl-1,4,5,6-tetrahydropyrrolo[3,4-c]pyrazol-3-yl}-4-(4-methylpiperazin-1-yl)benzamide (A1-Z-B20);

N-{5-[(3-bromophenyl)acetyl]-6,6-dimethyl-1,4,5,6-tetrahydropyrrolo[3,4-c]pyrazol-3-yl}-4-(4-methylpiperazin-1-yl)benzamide (A1-Z-B21);

N-{5-[(4-fluorophenyl)acetyl]-6,6-dimethyl-1,4,5,6-tetrahydropyrrolo[3,4-c]pyrazol-3-yl}-4-(4-methylpiperazin-1-yl)benzamide (A1-Z-B25);

N-{6,6-dimethyl-5-[(2-methylphenyl)acetyl]-1,4,5,6-tetrahydropyrrolo[3,4-c]pyrazol-3-yl}-4-(4-methylpiperazin-1-yl)benzamide (A1-Z-B27);

N-{5-[(3-fluorophenyl)acetyl]-6,6-dimethyl-1,4,5,6-tetrahydropyrrolo[3,4-c]pyrazol-3-yl}-4-(4-methylpiperazin-1-yl)benzamide (A1-Z-B28);

N-{6,6-dimethyl-5-[(3-methylphenyl)acetyl]-1,4,5,6-tetrahydropyrrolo[3,4-c]pyrazol-3-yl}-4-(4-methylpiperazin-1-yl)benzamide (A1-Z-B29);

N-{6,6-dimethyl-5-[(2,3,6-trifluorophenyl)acetyl]-1,4,5,6-tetrahydropyrrolo[3,4-c]pyrazol-3-yl}-4-(4-methylpiperazin-1-yl)benzamide (A1-Z-B33);

N-[5-(mesitylacetyl)-6,6-dimethyl-1,4,5,6-tetrahydropyrrolo[3,4-c]pyrazol-3-yl]-4-(4-methylpiperazin-1-yl)benzamide (A1-Z-B34);

N-{5-[(2,4-dichlorophenyl)acetyl]-6,6-dimethyl-1,4,5,6-tetrahydropyrrolo[3,4-c]pyrazol-3-yl}-4-(4-methylpiperazin-1-yl)benzamide (A1-Z-B36);

N-{5-[(2-fluorophenyl)acetyl]-6,6-dimethyl-1,4,5,6-tetrahydropyrrolo[3,4-c]pyrazol-3-yl}-4-(4-methylpiperazin-1-yl)benzamide (A1-Z-B37);

N-{5-[(2-chloro-6-fluorophenyl)acetyl]-6,6-dimethyl-1,4,5,6-tetrahydropyrrolo[3,4-c]pyrazol-3-yl}-4-(4-methylpiperazin-1-yl)benzamide (A1-Z-B38);

N-(6,6-dimethyl-5-{[2-(trifluoromethyl)phenyl]acetyl}-1,4,
5,6-tetrahydropyrrolo[3,4-c]pyrazol-3-yl)-4-(4-methylpiperazin-1-yl)benzamide (A1-Z-B42);
N-(6,6-dimethyl-5-{[2-nitro-4-(trifluoromethyl)phenyl]
acetyl}-1,4,5,6-tetrahydropyrrolo[3,4-c]pyrazol-3-yl)-4-
(4-methylpiperazin-1-yl)benzamide (A1-Z-B43);
N-{5-[(3,4-difluorophenyl)acetyl]-6,6-dimethyl-1,4,5,6-tetrahydropyrrolo[3,4-c]pyrazol-3-yl}-4-(4-methylpiperazin-1-yl)benzamide (A1-Z-B44);
N-{5-[(2,5-difluorophenyl)acetyl]-6,6-dimethyl-1,4,5,6-tetrahydropyrrolo[3,4-c]pyrazol-3-yl}-4-(4-methylpiperazin-1-yl)benzamide (A1-Z-B45);
N-{5-[(2,4-difluorophenyl)acetyl]-6,6-dimethyl-1,4,5,6-tetrahydropyrrolo[3,4-c]pyrazol-3-yl}-4-(4-methylpiperazin-1-yl)benzamide (A1-Z-B46);
N-{5-[(2-chlorophenyl)acetyl]-6,6-dimethyl-1,4,5,6-tetrahydropyrrolo[3,4-c]pyrazol-3-yl}-4-(4-methylpiperazin-1-yl)benzamide (A1-Z-B52);
N-{5-[(2-iodophenyl)acetyl]-6,6-dimethyl-1,4,5,6-tetrahydropyrrolo[3,4-c]pyrazol-3-yl}-4-(4-methylpiperazin-1-yl)benzamide (A1-Z-B53);
N-{5-[(2,3-difluorophenyl)acetyl]-6,6-dimethyl-1,4,5,6-tetrahydropyrrolo[3,4-c]pyrazol-3-yl}-4-(4-methylpiperazin-1-yl)benzamide (A1-Z-B54);
N-{6,6-dimethyl-5-[(2,4,6-trimethoxyphenyl)acetyl]-1,4,5,
6-tetrahydropyrrolo[3,4-c]pyrazol-3-yl}-4-(4-methylpiperazin-1-yl)benzamide (A1-Z-B55);
N-{5-[(2,6-difluorophenyl)acetyl]-6,6-dimethyl-1,4,5,6-tetrahydropyrrolo[3,4-c]pyrazol-3-yl}-3-(4-methylpiperazin-1-yl)benzamide (A2-Z-B5);
N-[6,6-dimethyl-5-(2-thienylacetyl)-1,4,5,6-tetrahydropyrrolo[3,4-c]pyrazol-3-yl]-4-(4-methylpiperazin-1-yl)benzamide (A1-Z-B56);
4-({5-[(2,6-difluorophenyl)acetyl]-6,6-dimethyl-2,4,5,6-tetrahydropyrrolo[3,4-c]pyrazol-3-yl}carbamoyl)benzoic acid (A6-Z-B5);
N-(2,6-dichlorophenyl)-6,6-dimethyl-3-[(4-methylbenzoyl)
amino]-4,6-dihydropyrrolo[3,4-c]pyrazole-5(1H)-carboxamide (A8-Z-B1);
3-[(4-chlorobenzoyl)amino]-N-(2,6-dichlorophenyl)-6,6-dimethyl-4,6-dihydropyrrolo[3,4-c]pyrazole-5(1H)-carboxamide (A11-Z-B1);
N-(2,6-dichlorophenyl)-3-[(3-fluorobenzoyl)amino]-6,6-dimethyl-4,6-dihydropyrrolo[3,4-c]pyrazole-5(1H)-carboxamide (A16-Z-B1);
3-(benzoylamino)-N-(2,6-dichlorophenyl)-6,6-dimethyl-4,
6-dihydropyrrolo[3,4-c]pyrazole-5(1H)-carboxamide (A17-Z-B1);
N-(2,6-dichlorophenyl)-6,6-dimethyl-3-{[(2E)-3-phenylprop-2-enoyl]amino}-4,6-dihydropyrrolo[3,4-c]pyrazole-5(1H)-carboxamide (A19-Z-B1);
N-(2,6-dichlorophenyl)-3-[(4-methoxybenzoyl)amino]-6,6-dimethyl-4,6-dihydropyrrolo[3,4-c]pyrazole-5(1H)-carboxamide (A24-Z-B1);
N-(2,6-dichlorophenyl)-3-(2-furoylamino)-6,6-dimethyl-4,
6-dihydropyrrolo[3,4-c]pyrazole-5(1H)-carboxamide (A26-Z-B1);
N-(2,6-dichlorophenyl)-6,6-dimethyl-3-[(2-thienylcarbonyl)amino]-4,6-dihydropyrrolo[3,4-c]pyrazole-5(1H)-carboxamide (A30-Z-B1);
N-(2,6-dichlorophenyl)-3-[(2,4-difluorobenzoyl)amino]-6,
6-dimethyl-4,6-dihydropyrrolo[3,4-c]pyrazole-5(1H)-carboxamide (A31-Z-B1);
N-(2,6-dichlorophenyl)-3-[(4-fluorobenzoyl)amino]-6,6-dimethyl-4,6-dihydropyrrolo[3,4-c]pyrazole-5(1H)-carboxamide (A32-Z-B1);
N-(2,6-dichlorophenyl)-3-[(3,4-dimethoxybenzoyl)amino]-6,6-dimethyl-4,6-dihydropyrrolo[3,4-c]pyrazole-5(1H)-carboxamide (A33-Z-B1);
N-{5-[(2,6-difluorophenyl)acetyl]-6,6-dimethyl-1,4,5,6-tetrahydropyrrolo[3,4-c]pyrazol-3-yl}-2-fluorobenzamide (A47-Z-B5);
N-{5-[(2,6-difluorophenyl)acetyl]-6,6-dimethyl-1,4,5,6-tetrahydropyrrolo[3,4-c]pyrazol-3-yl}-4-(dimethylamino)
benzamide (A65-Z-B5);
4-({5-[(2,6-dichlorophenyl)carbamoyl]-6,6-dimethyl-2,4,5,
6-tetrahydropyrrolo[3,4-c]pyrazol-3-yl}carbamoyl)benzoic acid (A6-Z-B1);
N-(2,5-dimethylphenyl)-6,6-dimethyl-3-{[4-(4-methylpiperazin-1-yl)benzoyl]amino}-4,6-dihydropyrrolo[3,4-c]
pyrazole-5(1H)-carboxamide (A1-Z-B59);
6,6-dimethyl-3-{[4-(4-methylpiperazin-1-yl)benzoyl]
amino}[2-(trifluoromethoxy)phenyl]-4,6-dihydropyrrolo
[3,4-c]pyrazole-5(1H)-carboxamide (A1-Z-B60);
N-(2,6-diisopropylphenyl)-6,6-dimethyl-3-{[4-(4-methylpiperazin-1-yl)benzoyl]amino}-4,6-dihydropyrrolo[3,
4-c]pyrazole-5(1H)-carboxamide (A1-Z-B73);
N-(2,6-dimethylphenyl)-6,6-dimethyl-3-{[4-(4-methylpiperazin-1-yl)benzoyl]amino}-4,6-dihydropyrrolo[3,4-c]
pyrazole-5(1H)-carboxamide (A1-Z-B74);
N-(2-methoxyphenyl)-6,6-dimethyl-3-{[4-(4-methylpiperazin-1-yl)benzoyl]amino}-4,6-dihydropyrrolo[3,4-c]
pyrazole-5(1H)-carboxamide (A1-Z-B77);
N-(2-chlorophenyl)-6,6-dimethyl-3-{[4-(4-methylpiperazin-1-yl)benzoyl]amino}-4,6-dihydropyrrolo[3,4-c]
pyrazole-5(1H)-carboxamide (A1-Z-B78);
N-(2-isopropylphenyl)-6,6-dimethyl-3-{[4-(4-methylpiperazin-1-yl)benzoyl]amino}-4,6-dihydropyrrolo[3,4-c]
pyrazole-5(1H)-carboxamide (A1-Z-B80);
N-(2,6-diethylphenyl)-6,6-dimethyl-3-{[4-(4-methylpiperazin-1-yl)benzoyl]amino}-4,6-dihydropyrrolo[3,4-c]
pyrazole-5(1H)-carboxamide (A1-Z-B85);
N-(2-chloro-6-methylphenyl)-6,6-dimethyl-3-{[4-(4-methylpiperazin-1-yl)benzoyl]amino}-4,6-dihydropyrrolo[3,
4-c]pyrazole-5(1H)-carboxamide (A1-Z-B89);
N-(2-fluorophenyl)-6,6-dimethyl-3-{[4-(4-methylpiperazin-1-yl)benzoyl]amino}-4,6-dihydropyrrolo[3,4-c]pyrazole-5(1H)-carboxamide (A1-Z-B92);
6,6-dimethyl-N-(2-methylphenyl)-3-[4-(4-methylpiperazin-1-yl)benzoyl]amino-4,6-dihydropyrrolo[3,4-c]pyrazole-5
(1H)-carboxamide (A1-Z-B94);
N-(2,6-dimethoxyphenyl)-6,6-dimethyl-3-{[4-(4-methylpiperazin-1-yl)benzoyl]amino}-4,6-dihydropyrrolo[3,
4-c]pyrazole-5(1H)-carboxamide (A1-Z-B95);
N-(2-tert-butylphenyl)-6,6-dimethyl-3-{[4-(4-methylpiperazin-1-yl)benzoyl]amino}-4,6-dihydropyrrolo[3,4-c]
pyrazole-5(1H)-carboxamide (A1-Z-B96);
6,6-dimethyl-3-{[4-(4-methylpiperazin-1-yl)benzoyl]
amino}-N-[2-(methylthio)phenyl]-4,6-dihydropyrrolo[3,
4-c]pyrazole-5(1H)-carboxamide (A1-Z-B102);
formic acid-N-[2-fluoro-6-(trifluoromethyl)phenyl]-6,6-dimethyl-3-{[4-(4-methylpiperazin-1-yl)benzoyl]
amino}-2,6-dihydropyrrolo[3,4-c]pyrazole-5(4H)-carboxamide (1:1) (A1-Z-B104);
N-(2-ethylphenyl)-6,6-dimethyl-3-{[4-(4-methylpiperazin-1-yl)benzoyl]amino}-4,6-dihydropyrrolo[3,4-c]pyrazole-5(1H)-carboxamide (A1-Z-B106);
6,6-dimethyl-3-{[4-(4-methylpiperazin-1-yl)benzoyl]
amino}-N-[2-(trifluoromethyl)phenyl]-4,6-dihydropyrrolo[3,4-c]pyrazole-5(1H)-carboxamide (A1-Z-B108);

N-[2-chloro-6-(trifluoromethyl)phenyl]-6,6-dimethyl-3-{[4-(4-methylpiperazin-1-yl)benzoyl]amino}-4,6-dihydropyrrolo[3,4-c]pyrazole-5(1H)-carboxamide (A1-Z-B111);

methyl 3-({5-[(2,6-dichlorophenyl)carbamoyl]-6,6-dimethyl-1,4,5,6-tetrahydropyrrolo[3,4-c]pyrazol-3-yl}carbamoyl)benzoate (A89-Z-B1);

N-(2,6-dichlorophenyl)-3-[(2,5-difluorobenzoyl)amino]-6,6-dimethyl-4,6-dihydropyrrolo[3,4-c]pyrazole-5(1H)-carboxamide (A51-Z-B1);

N-(2,6-dichlorophenyl)-6,6-dimethyl-3-[(3-methylbenzoyl)amino]-4,6-dihydropyrrolo[3,4-c]pyrazole-5(1H)-carboxamide (A52-Z-B1);

3-[(1-benzothien-2-ylcarbonyl)amino]-N-(2,6-dichlorophenyl)-6,6-dimethyl-4,6-dihydropyrrolo[3,4-c]pyrazole-5(1H)-carboxamide (A55-Z-B1);

N-(2,6-dichlorophenyl)-3-{[(1,3-dimethyl-1H-pyrazol-5-yl)carbonyl]amino}-6,6-dimethyl-4,6-dihydropyrrolo[3,4-c]pyrazole-5(1H)-carboxamide (A66-Z-B1);

3-{[(4-bromo-2-thienyl)carbonyl]amino}-N-(2,6-dichlorophenyl)-6,6-dimethyl-4,6-dihydropyrrolo[3,4-c]pyrazole-5(1H)-carboxamide (A68-Z-B1);

N-{5-[(2,6-difluorophenyl)acetyl]-6,6-dimethyl-1,4,5,6-tetrahydropyrrolo[3,4-c]pyrazol-3-yl}-3-fluorobenzamide (A16-Z-B5);

N-{5-[(2,6-difluorophenyl)acetyl]-6,6-dimethyl-1,4,5,6-tetrahydropyrrolo[3,4-c]pyrazol-3-yl}benzamide (A17-Z-B5);

N-{5-[(2,6-difluorophenyl)acetyl]-6,6-dimethyl-1,4,5,6-tetrahydropyrrolo[3,4-c]pyrazol-3-yl}-4-methoxybenzamide (A24-Z-B5);

N-{5-[(2,6-difluorophenyl)acetyl]-6,6-dimethyl-1,4,5,6-tetrahydropyrrolo[3,4-c]pyrazol-3-yl}-2-furamide (A26-Z-B5);

N-{5-[(2,6-difluorophenyl)acetyl]-6,6-dimethyl-1,4,5,6-tetrahydropyrrolo[3,4-c]pyrazol-3-yl}thiophene-2-carboxamide (A30-Z-B5);

N-{5-[(2,6-difluorophenyl)acetyl]-6,6-dimethyl-1,4,5,6-tetrahydropyrrolo[3,4-c]pyrazol-3-yl}-N'-(1-methylpiperidin-4-yl)terephthalamide (A72-Z-B5);

N-{5-[(2,6-dichlorophenyl)carbamoyl]-6,6-dimethyl-1,4,5,6-tetrahydropyrrolo[3,4-c]pyrazol-3-yl}-N'-[3-(dimethylamino)propyl]terephthalamide (A71-Z-B1);

N-{5-[(2,6-dichlorophenyl)carbamoyl]-6,6-dimethyl-1,4,5,6-tetrahydropyrrolo[3,4-c]pyrazol-3-yl}-N'-(1-methylpiperidin-4-yl)terephthalamide (A72-Z-B1);

N-{5-[(2,6-dichlorophenyl)carbamoyl]-6,6-dimethyl-2,4,5,6-tetrahydropyrrolo[3,4-c]pyrazol-3-yl}terephthalamide (A75-Z-B1);

N-{5-[(2,6-dichlorophenyl)carbamoyl]-6,6-dimethyl-2,4,5,6-tetrahydropyrrolo[3,4-c]pyrazol-3-yl}-N'-hydroxyterephthalamide (A76-Z-B1);

N-(2,6-dichlorophenyl)-6,6-dimethyl-3-[(4-{[(1-methylpiperidin-4-yl)carbonyl]amino}benzoyl)amino]-4,6-dihydropyrrolo[3,4-c]pyrazole-5(1H)-carboxamide (A77-Z-B1);

N-(2,6-dichlorophenyl)-6,6-dimethyl-3-{[4-(methylsulfonyl)benzoyl]amino}-4,6-dihydropyrrolo[3,4-c]pyrazole-5(1H)-carboxamide (A78-Z-B1);

3-({5-[(2,6-dichlorophenyl)carbamoyl]-6,6-dimethyl-1,4,5,6-tetrahydropyrrolo[3,4-c]pyrazol-3-yl}carbamoyl)benzoic acid (A79-Z-B1);

N-{5-[(2,6-dichlorophenyl)carbamoyl]-6,6-dimethyl-1,4,5,6-tetrahydropyrrolo[3,4-c]pyrazol-3-yl}isophthalamide (A80-Z-B1);

N-{5-[(2,6-dichlorophenyl)carbamoyl]-6,6-dimethyl-1,4,5,6-tetrahydropyrrolo[3,4-c]pyrazol-3-yl}-N'-(1-methylpiperidin-4-yl)isophthalamide (A81-Z-B1);

N-{5-[(2,6-dichlorophenyl)carbamoyl]-6,6-dimethyl-1,4,5,6-tetrahydropyrrolo[3,4-c]pyrazol-3-yl}-N'-hydroxyisophthalamide (A82-Z-B1);

N-(2,6-dichlorophenyl)-6,6-dimethyl-3-[(3-{[(1-methylpiperidin-4-yl)carbonyl]amino}benzoyl)amino]-4,6-dihydropyrrolo[3,4-c]pyrazole-5(1H)-carboxamide (A83-Z-B1);

3-[(3-aminobenzoyl)amino]-N-(2,6-dichlorophenyl)-6,6-dimethyl-4,6-dihydropyrrolo[3,4-c]pyrazole-5(1H)-carboxamide (A84-Z-B1);

3-[(4-aminobenzoyl)amino]-N-(2,6-dichlorophenyl)-6,6-dimethyl-4,6-dihydropyrrolo[3,4-c]pyrazole-5(1H)-carboxamide (A85-Z-B1);

N-(2,6-dichlorophenyl)-6,6-dimethyl-3-{[4-(4-methylpiperazin-1-yl)-3-nitrobenzoyl]amino}-4,6-dihydropyrrolo[3,4-c]pyrazole-5(1H)-carboxamide (A86-Z-B1);

N-(2,6-dichlorophenyl)-3-[(4-fluoro-3-nitrobenzoyl)amino]-6,6-dimethyl-4,6-dihydropyrrolo[3,4-c]pyrazole-5(1H)-carboxamide (A87-Z-B1);

diethyl[4-({5-[(2,6-dichlorophenyl)carbamoyl]-6,6-dimethyl-2,4,5,6-tetrahydropyrrolo[3,4-c]pyrazol-3-yl}carbamoyl)phenyl]phosphonate (A91-Z-B1);

N-(3,5-dimethylisoxazol-4-yl)-6,6-dimethyl-3-({[4-(4-methylpiperazin-1-yl)phenyl]carbonyl}amino)-4,6-dihydropyrrolo[3,4-c]pyrazole-5(1H)-carboxamide trifluoroacetate (A1-Z-B115);

N-(2-cyanophenyl)-6,6-dimethyl-3-({[4-(4-methylpiperazin-1-yl)phenyl]carbonyl}amino)-4,6-dihydropyrrolo[3,4-c]pyrazole-5(1H)-carboxamide trifluoroacetate (A1-Z-B116);

N-(2-chloropyridin-3-yl)-6,6-dimethyl-3-({[4-(4-methylpiperazin-1-yl)phenyl]carbonyl}amino)-4,6-dihydropyrrolo[3,4-c]pyrazole-5(1H)-carboxamide trifluoroacetate (A1-Z-B120);

N-(2-bromo-6-fluorophenyl)-6,6-dimethyl-3-({[4-(4-methylpiperazin-1-yl)phenyl]carbonyl}amino)-4,6-dihydropyrrolo[3,4-c]pyrazole-5(1H)-carboxamide trifluoroacetate (A1-Z-B122);

N-(2,6-dichloro-4-nitrophenyl)-6,6-dimethyl-3-({[4-(4-methylpiperazin-1-yl)phenyl]carbonyl}amino)-4,6-dihydropyrrolo[3,4-c]pyrazole-5(1H)-carboxamide trifluoroacetate (A1-Z-B124);

N-[2,6-dichloro-4-(trifluoromethoxy)phenyl]-6,6-dimethyl-3-({[4-(4-methylpiperazin-1-yl)phenyl]carbonyl}amino)-4,6-dihydropyrrolo[3,4-c]pyrazole-5(1H)-carboxamide trifluoroacetate (A1-Z-B128);

N-(2,6-dichlorophenyl)-3-[({2-[(2-methoxyethyl)amino]-4-(4-methylpiperazin-1-yl)phenyl}carbonyl)amino]-6,6-dimethyl-4,6-dihydropyrrolo[3,4-c]pyrazole-5(1H)-carboxamide (A95-Z-B1), and N-(2,6-dichlorophenyl)-3-({[2-{[(1S)-2-methoxy-1-methylethyl]amino}-4-(4-methylpiperazin-1-yl)phenyl]carbonyl}amino)-6,6-dimethyl-4,6-dihydropyrrolo[3,4-c]pyrazole-5(1H)-carboxamide (A96-Z-B1).

The present inventions also provides a process for the preparation of compounds of formula (I). Compounds of formula (I) and the pharmaceutically acceptable salts may be obtained by two independent ways: pathway A or pathway B.

Pathway A comprises:

a) reacting any of the two regioisomeric forms of the compound of formula (II)

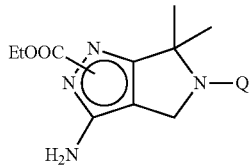 (II)

wherein Q is a suitable protecting group, preferably tert-butoxycarbonyl (t-boc), with a compound of formula (III)

R—CO—Y (III)

wherein R is as defined above and Y is an halogen atom, so as to obtain the compound of formula (IV)

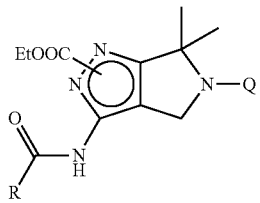 (IV)

wherein R and Q are defined as above;

b) deprotecting the amino group of the compound of formula (IV) so as to obtain the corresponding derivative of formula (V)

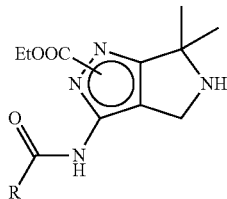 (V)

wherein R has the above reported meanings;

c) reacting the compound of formula (V) according to any one of the alternative steps c.1), c.2), c.3):

c1) with an acid of formula (VI),

Ar-A-COOH (VI)

wherein Ar is as defined above and A is $CH_2$, in the presence of a suitable condensing agent so as to obtain a compound of formula (VII)

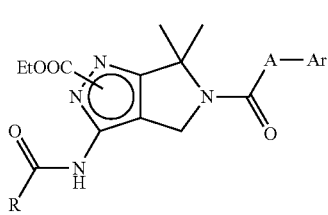 (VII)

wherein R and Ar are as defined above and A is $CH_2$;

c.2) with an isocyanate of formula (VIII)

Ar—NCO (VIII)

wherein Ar is as defined above, so as to obtain a compound of formula (VII) wherein R and Ar are as defined above and A is NH;

c.3) with an amine of formula (IX)

Ar—$NH_2$ (IX)

wherein Ar is as defined above, in the presence of triphosgene, di-tert-butyl dicarbonate or of a suitable cloroformate so as to obtain a compound of formula (VII) wherein R and Ar are as defined above and A is NH;

d) reacting the compound of formula (VII) prepared according to any one of steps from c.1) to c.3) under basic conditions, so as to obtain the corresponding derivative of formula (I) defined above; and, optionally, e) converting them into other compounds of formula (I) and/or into hydrates, solvates, complexes, metabolites, prodrugs, carriers, N-oxides and pharmaceutically acceptable salts thereof.

Pathway B comprises:

f) removing the amino protecting group Q from compound of formula (II) as defined above, so to obtain a compound of formula (X);

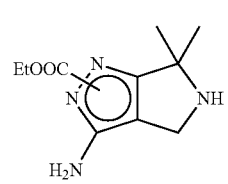 (X)

g) reacting compound of formula (X) accordingly to any one of the alternative steps c.1), c.2) or c.3), to obtain a compound of formula (XI)

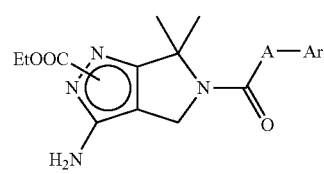 (XI)

wherein Ar and A are defined above;

h) reacting compounds of formula (XI) as defined above, with compounds of formula (III) as defined above, so to obtain compounds of formula (VII) as defined above;

i) reacting the resulting compound of formula (VII) under basic conditions, so as to obtain the corresponding derivative of formula (I) as defined above; and, optionally, j) converting them into other compounds of formula (I), and/or into hydrates, solvates, complexes, metabolites, prodrugs, carriers, N-oxides and pharmaceutically acceptable salts thereof.

It is to be noted that a compound of formula (II), (IV), (V), (VII), (X) and (XI) as defined above can be in any one of its isomeric forms a or b:

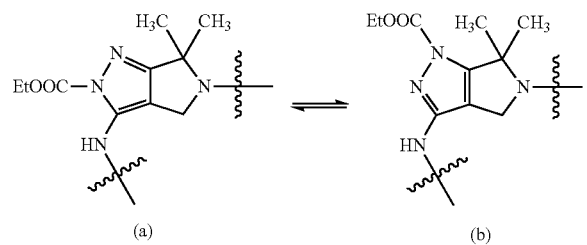 [SMILES: *Nc1c2c(nn1C(=O)OCC)C(C)(C)N(*)C2 ; *Nc1nn(C(=O)OCC)c2c1CN(*)C2(C)C]

(a)  (b)

The two isomers of formula (a) and (b) may be conveniently separated according to well-known methods, for instance under chromatographic conditions, and each isomer so isolated subsequently worked out. In the alternative, the mixture of isomers can be treated as such in the subsequent steps of the process, without providing any separation. In fact, as the ethoxycarbonyl group leading to two distinct isomers is finally removed at the end of the process, it is clear to the skilled person that both the above pathways can be carried out for preparing the compounds of formula (I) of the invention. Preferably, however, the process is carried out by first separating and isolating the two isomers of formula (a) and (b) from their mixture, as reported in the working examples, and by subsequently reacting them to the desired compounds.

The above process can be carried out according to methods well known in the art. From all of the above, it is clear to the person skilled in the art that if a compound of formula (I), prepared according to the above process, is obtained as a mixture of isomers, their separation into the single isomers of formula (I), carried out according to conventional techniques, is still within the scope of the present invention.

Likewise, the conversion into the free compound (I) of a corresponding salt thereof, according to well-known methods, is still within the scope of the invention.

According to step (a) or (h) of the process, the compound of formula (II) or (XI) is reacted with a suitable derivative of formula (III) wherein Y represents a halogen atom, preferably chlorine or bromine. Typically, the compound of formula (II) or (XI) is dissolved in a suitable solvent such as dichloromethane, dimethylformamide, tetrahydrofuran, dioxane or the like, and a suitable base such as triethylamine, diisopropylethylamine, sodium carbonate or the like is added. The compound of formula (III) is then added and the mixture stirred for a time of about 2 to about 15 hours, at a temperature ranging from about 20° C. to about 80° C. A suitable catalyst such as dimethylaminopyridine may be optionally used.

According to step (b) or (f) of the process, the protected amino group in formula (IV) or (II) is deprotected under well-known operative conditions, for instance under acidic conditions in the presence of trifluoroacetic or hydrochloric acid. The compound of formula (IV) or (II) is thus suspended in a suitable solvent such as dichloromethane or dioxane, and treated with a concentrated solution of the selected acid. Alternatively, commercially available solutions of gaseous hydrogen chloride dissolved in dioxane (4 M HCl) may be advantageously employed. The mixture is then stirred for a time of about 2 hours to about 15 hours at a temperature ranging from about 20° C. to about 40° C.

According to step (c.1) of the process, the compound of formula (V) or (X) is reacted with an acid derivative of formula (VI). The condensation is carried out in the presence of a suitable condensing agent such as, for instance, dicyclohexylcarbodiimide (DCC), 1-ethyl-3-(3'-dimethylaminopropyl)carbodiimide (EDC) or O-benzotriazolyl tetramethylisouronium tetrafluoroborate (TBTU), and by operating according to well-known methods for preparing carboxamido derivatives.

According to step (c.2) of the process, the compound of formula (V) or (X) is reacted with an isocyanate of formula (VIII). The reaction is carried out in tetrahydrofuran (THF) or in a suitable halogenated hydrocarbon, preferably dichloromethane (DCM), for a time of about 2 hours to about 15 hours at a temperature ranging from about –0° C. to 40° C.

According to step (c.3) of the process, the compound of formula (V) or (X) is reacted with an amine of formula (IX) in the presence of triphosgene, di-text-butyl dicarbonate or of a suitable chloroformate, for instance 4-nitrophenyl chloroformate, so as to get the corresponding ureido derivative. The reaction is carried out in tetrahydrofuran (THF) or in a suitable halogenated hydrocarbon, preferably dichloromethane (DCM), and in the presence of a suitable amine such as diisopropylethylamine or triethylamine at a temperature ranging from –20 to 150° C. irradiating if necessary the reaction with microwave.

According to step (d) or (i) of the process, the compound of formula (VII) being obtained in any one of steps from (c.1) to (c.3) is reacted with a suitable base, for instance triethylamine, piperidine, N-methylpiperazine or NaOH, and in the presence of a suitable solvent such as methanol or ethanol so as to obtain the desired compound of formula (I). The reaction is carried out at a temperature ranging from about 20° C. to 70° C.

Finally, according to steps (e) or (j) of the process, these latter compounds (I) may be optionally converted into hydrates, solvates, complexes, metabolites, prodrugs, carriers, N-oxides and pharmaceutically acceptable salts thereof by working according to conventional methods or, alternatively, may be converted into additional compounds of formula (I). Just as a non limiting example, compounds of formula (I) bearing a carboxyester function may be converted into a variety of derivatives according to methods well known in the art to convert carboxyester groups into carboxamides, N-substituted carboxamides, N,N-disubstituted carboxamides, carboxylic acids, and the like.

The operative conditions are those widely known in the art and may comprise, for instance in the conversion of a carboxyester group into a carboxamide group, the reaction with ammonia or ammonium hydroxide in the presence of a suitable solvent such as a lower alcohol, dimethylformamide or mixtures thereof; preferably the reaction is carried out with ammonium hydroxide in a methanol/dimethylformamide mixture, at a temperature ranging from about 50° C. to about 100° C. Analogous operative conditions apply in the preparation of N-substituted or N,N-disubstituted carboxamides wherein a suitable primary or secondary amine is used in place of ammonia or ammonium hydroxide. Likewise, carboxyester groups may be converted into carboxylic acid derivatives through basic or acidic hydrolysis conditions, widely known in the art and then coupled with a suitable primary or secondary amines in presence of a condensing agent to yield the corresponding carboxamido derivatives. As an additional example, compounds of formula (I) bearing an amino function may be easily converted into the corresponding carboxamido or ureido derivatives by reaction with suitable acylchlorides or with suitable acids in presence of a condensing agent or in the case of ureido derivatives with suitable amines and triphosgene as described above in the step (c.3).

From all of the above it is clear to the skilled person that according to step (e) or (j) of the process, any compound of formula (I) bearing a functional group which can be further derivatized to another functional group, by working according to methods well known in the art thus leading to other compounds of formula (I), has to be intended as comprised within the scope of the present invention.

According to any variant of the process for preparing the compounds of formula (I), the starting materials and any other reactants are known or easily prepared according to known methods.

The starting material of formula (II) can be prepared as described in the aforementioned WO04/56827.

The starting material of formula (III) are commercially available or can be prepared as described in WO07/68619 (Nerviano Medical Sciences Srl).

The starting materials of formula (VI), (VIII) and (IX) are commercially available.

As it will be readily appreciated, if the compounds of formula (I) prepared according to the process described above are obtained as an admixture of isomers, their separation into the single isomers of formula (I), according to conventional techniques, is within the scope of the present invention. Conventional techniques for racemate resolution include, for instance, partitioned crystallization of diastereoisomeric salt derivatives or preparative chiral HPLC.

In addition, it is clear from the above that a given compound of formula (I) may be prepared either by starting from the mixture of the regioisomers of formula (II) or, alternatively, from each one of the two regioisomers themselves.

When preparing the compounds of formula (I) according to any one of the aforementioned process variants, optional functional groups within the starting materials or the intermediates thereof and which could give rise to unwanted side reactions, need to be properly protected according to conventional techniques. Likewise, the conversion of these latter into the free deprotected compounds may be carried out according to known procedures.

Pharmacology

The compounds of formula (I) are active as protein kinase inhibitors and are therefore useful, for instance, to restrict the unregulated proliferation of tumor cells.

In therapy, they may be used in the treatment of various tumors, such as those formerly reported, as well as in the treatment of other cell proliferative disorders such as psoriasis, vascular smooth cell proliferation associated with atherosclerosis and post-surgical stenosis and restenosis.

The inhibiting activity of putative PLK-1 inhibitors and the potency of selected compounds was determined through the assay described below.

The short forms and abbreviations used herein have the following meaning:

| | |
|---|---|
| Ci | Curie |
| DMSO | dimethylsulfoxide |
| KDa | kiloDalton |
| microCi | microCurie |
| mg | milligram |
| microg | microgram |
| ng | nanogram |
| L | liter |
| mL | milliliter |
| microL | microliter |
| M | molar |

-continued

| | |
|---|---|
| mM | millimolar |
| microM | micromolar |
| nM | nanomolar |
| Et | Ethyl |

Cloning, Expression and Purification of Recombinant PLK1 Kinase Domain.

PLK1 kinase domain (corresponding to residues 2-345 of the full length sequence, see Swiss-Prot accession number P53350) was PCR amplified from the full-length human PLK1 gene purchased from imaGenes as clone IRATp970A078D.

Amplification was performed using the forward oligonucleotide:

[SEQ ID NO: 1]
5'GGGGACAAGTTTGTACAAAAAAGCAGGCTTATTCGAAAACCTGTATT

TTCAGGGCCCTAGTGCTGCAGTGACTGCAGGGAAG3' and the reverse oligonucleotide:

[SEQ ID NO: 2]
5'GGGGACCACTTTGTACAAGAAAGCTGGGTTTCACTATTTATTGAGGA

CTGTGAGGGGCTT -3'.

For cloning purposes, the oligonucleotides included attB sites in order to obtain an attB-flanked PCR product suitable for cloning using the Gateway® technology (Invitrogen). Furthermore, for purification purposes, forward primer included a TEV® cleavage site (Amersham Biosciences). The resulting PCR product was cloned in the pDONR221 plasmid and then transferred in the baculovirus expression vector pVL1393 (Invitrogen) Gateway®-modified. For expression and purification purposes, a His tag was added N-terminal to the PLK kinase domain. Cloning was performed according to the protocols described in the Gateway® manual.

Baculoviruses were generated by cotransfecting Sf9 insect cells with the expression vector and the viral DNA using the BaculoGold® transfection kit (Pharmingen). Viral supernatant was recovered after 5 days and subjected to 3 rounds of amplification to increase viral titer. Recombinant protein was produced by infecting High5 insect cells. After 48 hours of infection, cells were recovered, pelletted and freezed at −80° C. For purification of recombinant protein, pellet was thawed, resuspended in lysis buffer (PBS, NaCl 150 mM, CHAPS 0.1%, DTT 20 mM, glycerol 10%, protease inhibitors) and lysed by sonication. Lysate was cleared by centrifugation and loaded on a Nichel affinity column. After extensive wash, recombinant protein was cleaved and eluted by incubation with TEV® protease.

Biochemical Assay for Inhibitors of PLK-1 Kinase Activity

The inhibitory activity of putative kinase inhibitors and the potency of selected compounds were determined using a trans-phosphorylation assay.

Specific peptide or protein substrates are trans-phosphorylated by their specific serine-threonine or tyrosine kinase, in the presence of ATP traced with $^{33}P$-γ-ATP, and in the presence of their own optimal buffer and cofactors.

At the end of the phosphorylation reaction, more than 98% cold ATP and radioactive ATP is captured by an excess of the ion exchange dowex resin; the resin then settles down to the bottom of the reaction plate by gravity.

Supernatant, containing the phosphorylated substrate, is subsequently withdrawn and transferred into a counting plate, then evaluated by β-counting.

Reagents/Assay Conditions i. Dowex Resin Preparation 500 g of wet resin (SIGMA, custom prepared resin DOWEX 1×8 200-400 mesh, 2.5 Kg) are weighed out and diluted to 2 L in 150 mM sodium formate, pH 3.00.

The resin is allowed to settle down (some hours) and then the supernatant is discarded.

After three washes as above over a couple of days, the resin is allowed to settle, the supernatant is discarded and two volumes of 150 mM sodium formate buffer are added per volume of pellet. The pH is then measured and should be around 3.00. The washed resin is stable for more than one week; the stock resin is kept at 4° C. before use.

ii. Kinase Buffer (KB)

Kinase buffer was composed of 50 mM HEPES pH 7.9 containing 10 mM $MnCl_2$, 1 mM DTT, 3 microM $NaVO_3$, and 0.2 mg/mL BSA, 10 mM β-glycerophosphate.

iii. Assay Conditions

The kinase assay was run with a final enzyme concentration PLK-1 of 3 nM, in presence of 40 microM ATP, 3 nM $^{33}$P-γ-ATP and 85 microM substrate alpha-casein, SIGMA, # C-3240.

Robotized Dowex Assay 1) 3× Enzyme mix (done in Kinase Buffer 3×), 5 microL/well 2) 3× substrate and ATP mix (done in ddH2O), together with $^{33}$P-γ-ATP, 5 microL/well 3) 3× test compounds (diluted into ddH2O-3% DMSO)-5 microL/well Compound Dilution and Assay Scheme is Reported Below.

i. Dilution of Compounds 10 mM stock solutions of test compounds in 100% DMSO were distributed into 96 well 12×8 format microtiter plates.

For % inhibition studies, individual dilution plates at 1 mM, 100 microM and 10 microM are prepared in 100% DMSO, then diluted at a 3× concentration (30, 3 and 0.3 microM) in $ddH_2O$, 3% DMSO. A Multimek 96 (Beckman) is used for dilutions and compound pipetting into the test plates For IC50 determination, compounds are received as 1 mM, 100% DMSO solutions, plated into the first column of a microtiter plate (A1 to G1), 100 microL.

A Biomek 2000 (Beckman) is used for serial 1:3 dilutions in water, 3% DMSO, from column A1 to A10 and for all the seven compounds in the plate. In a standard experiment, the highest concentration of all compounds is 30 microM, then diluted in the final test mixture down to 10 microM.

ii. Assay Scheme 384-well plates, V bottom (test plates) are prepared with 5 microL of the compound dilution (3×) and then placed onto a PlateTrak 12 robotized station (Perkin Elmer; the robot has one 384-tips pipetting head for starting the assay plus one 96-tips head for dispensing the resin) together with one reservoir for the Enzyme mix (3×) and one for the ATP mix (3×). At the start of the run, the robot aspirates 5 microL of ATP mix, makes an air gap inside the tips (3 microL) and aspirates 5 microL of PLK1 mix. The following dispensation into the plates allows the kinase reaction to start upon 3 cycles of mixing, done by the robot itself.

At this point, the correct concentration is restored for all reagents.

The robot incubates the plates for 60 minutes at room temperature, and then stops the reaction by pipetting 70 microL of dowex resin suspension into the reaction mix.

Three cycles of mixing are done immediately after the addition of the resin.

Another mixing cycle is performed after all the plates are stopped, this time using normal tips: the plates are then allowed to rest for about one hour in order to maximize ATP capture. At this point, 20 microL of the supernatant are transferred into 384-Optiplates (Perkin-Elmer), with 70 microL of Microscint 40 (Perkin-Elmer); after 5 min of orbital shaking the plates are read on a Perkin-Elmer Top Count radioactivity counter.

iii. Data Analysis

Data are analysed by an internally customized version of the SW package "Assay Explorer" that provides either % inhibition for primary assays or sigmoidal fittings of the ten-dilutions curves for IC50 determination, for the secondary assays/hit confirmation routines.

Biochemical Assay for Inhibitors of Aurora-2 Kinase Activity

The in vitro kinase inhibition assay was conducted in the same way as described for PLK-1 enzyme.

i. Kinase Buffer (KB) for Aurora-2

The kinase buffer was composed of 50 mM HEPES, pH 7.0, 10 mM $MnCl_2$, 1 mM DTT, 3 microM $NaVO_3$, and 0.2 mg/mL BSA.

ii. Assay Conditions for Aurora-2 (Final Concentrations)

The kinase assay was run with an enzyme concentration of 2.5 nM, 10 microM ATP, 1 nM $^{33}$P-γ-ATP, and 8 microM substrate, composed of 4 LRRWSLG repeats.

Inhibition Assay of Cdk2/Cyclin A activity

Kinase reaction: 1.5 microM histone H1 substrate, 25 microM ATP (0.2 microCi P33γ-ATP), 30 ng of baculovirus co-expressed Cdk2/Cyclin A, 10 microM inhibitor in a final volume of 100 microL buffer (TRIS HCl 10 mM pH 7.5, $MgCl_2$ 10 mM, 7.5 mM DTT) were added to each well of a 96 U bottom well plate. After 10 min at 37° C. incubation, reaction was stopped by 20 microL EDTA 120 mM.

Capture: 100 microL were transferred from each well to MultiScreen plate, to allow substrate binding to phosphocellulose filter. Plates were then washed 3 times with 150 microL/well PBS $Ca^{++}/Mg^{++}$ free and filtered by MultiScreen filtration system.

In Vitro Cell Proliferation Assay

A2780 human ovarian and MCF7 human breast cancer cells (1250 cells/well) were seeded in white 384 well-plates in complete medium (RPMI1640 or EMEM plus 10% Fetal bovine serum) and treated with compounds dissolved in 0.1% DMSO, 24 h after seeding. The cells were incubated at 37° C. and 5% CO2 and after 72 hours the plates were processed using CellTiter-Glo assay (Promega) following the manufacturer's instruction.

CellTiter-Glo is a homogenous method based on the quantification of the ATP present, an indicator of metabolitically active cells. ATP is quantified using a system based on luciferase and D-luciferin resulting into light generation. The luminescent signal is proportional to the number of cells present in culture.

Briefly 25 microL/well reagent solution are added to each wells and after 5 minutes shacking microplates are red by a luminometer. The luminescent signal is proportional to the number of cells present in culture.

Given the above inhibition assays, the compounds of formula (I) of the invention resulted to possess a remarkable PLK inhibitory activity, typically with $IC_{50}$ lower than 0.6 microM. See, as an example, the following Table A reporting the experimental data of some representative compounds of the invention of formula (I) being tested in biochemical assay as PLK-1 inhibitors and in A2780 cell proliferation assay ($IC_{50}$ microM) in comparison with the closest compound of the prior art, described in the aforementioned WO 02/12242, page 75, compound 1126.

TABLE A

| Compd N° | Code | PLK-1 $IC_{50}$ (microM) Biochemical Assay | A2780 $IC_{50}$ (microM) Cell proliferation Assay |
|---|---|---|---|
| Reference Compound | — | >4.2 | 2.66 |
| 44 | A1-Z-B42 | 0.075 | 0.38 |
| 60 | A1-Z-B56 | 0.052 | 0.071 |
| 178 | A1-Z-B106 | 0.096 | 0.019 |
| 250 | A84-Z-B1 | 0.030 | 0.119 |
| 251 | A85-Z-B1 | 0.024 | 0.063 |
| 64 | A8-Z-B1 | 0.230 | 0.209 |

Surprisingly, the PLK-1 inhibitory activity of the compounds of the present invention resulted to be markedly superior to that of the reference compound.

So far, the novel compounds of the invention are unexpectedly endowed with a PLK-1 inhibitory activity significantly higher than that of the structurally closest prior art compounds of the aforementioned WO 02/12242 and are thus particularly advantageous, in therapy, against proliferative disorders associated with an altered cell cycle dependent kinase activity such as cancer.

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, conditions of the patient and administration route. For example, a suitable dosage adopted for oral administration of a compound of formula (I) may range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim of better illustrating the present invention, without posing any limitation to it, the following examples are now given.

EXAMPLES

Before describing the synthetic preparation of some compounds of formula (I) of the invention, as reported in the following examples, attention should be given to the fact that all the compounds are conveniently and unambiguously identified through a coding system (see following table III), some of them are herewith listed and indicated according to their chemical name whilst others have been listed with the coding system together with their $^1$H-NMR data and/or HPLC/Mass data (see following table IV).

Each code, in particular, identifies a single specific final compound of formula (I) and consists of three units A-Z-B.

Each specific A and B group is represented and consecutively numbered in the following table I and II respectively.

Z refers to the central core of the divalent moiety which is substituted by groups A and B:

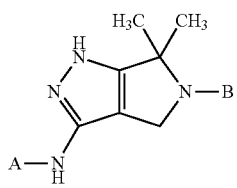

For ease of reference, all of the A and B groups of tables I and II have been identified with the proper chemical formula also indicating their respective point of attachment to the rest of the molecule Z.

Therefore, just as an example, the code A1-Z-B4 of table III represents the compound of formula (I) having the central Z core substituted by the group A1 and by the group B4, so identifying the structure reported below:

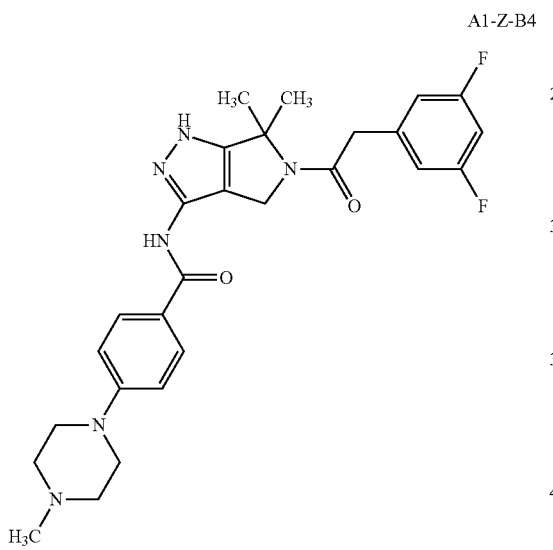

A1-Z-B4

TABLE I

| A | Code |
|---|---|
| 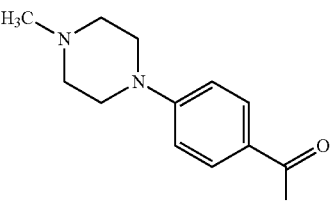 | A1 |
| 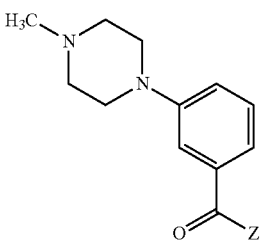 | A2 |

TABLE I-continued

| A | Code |
|---|---|
| 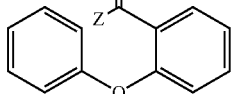 | A3 |
| 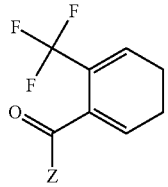 | A4 |
| 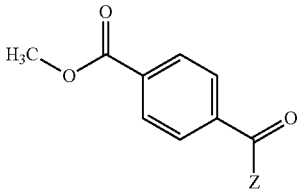 | A5 |
| 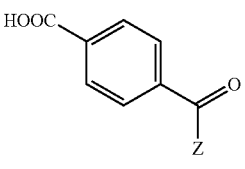 | A6 |
| 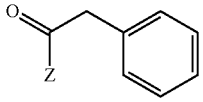 | A7 |
| 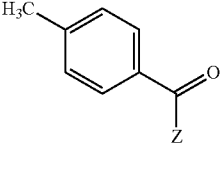 | A8 |
| 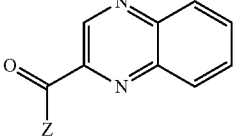 | A9 |
| 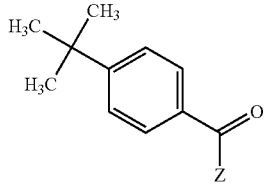 | A10 |
| 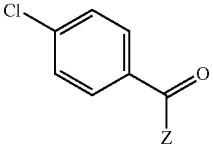 | A11 |

TABLE I-continued
| A | Code |
|---|---|
| 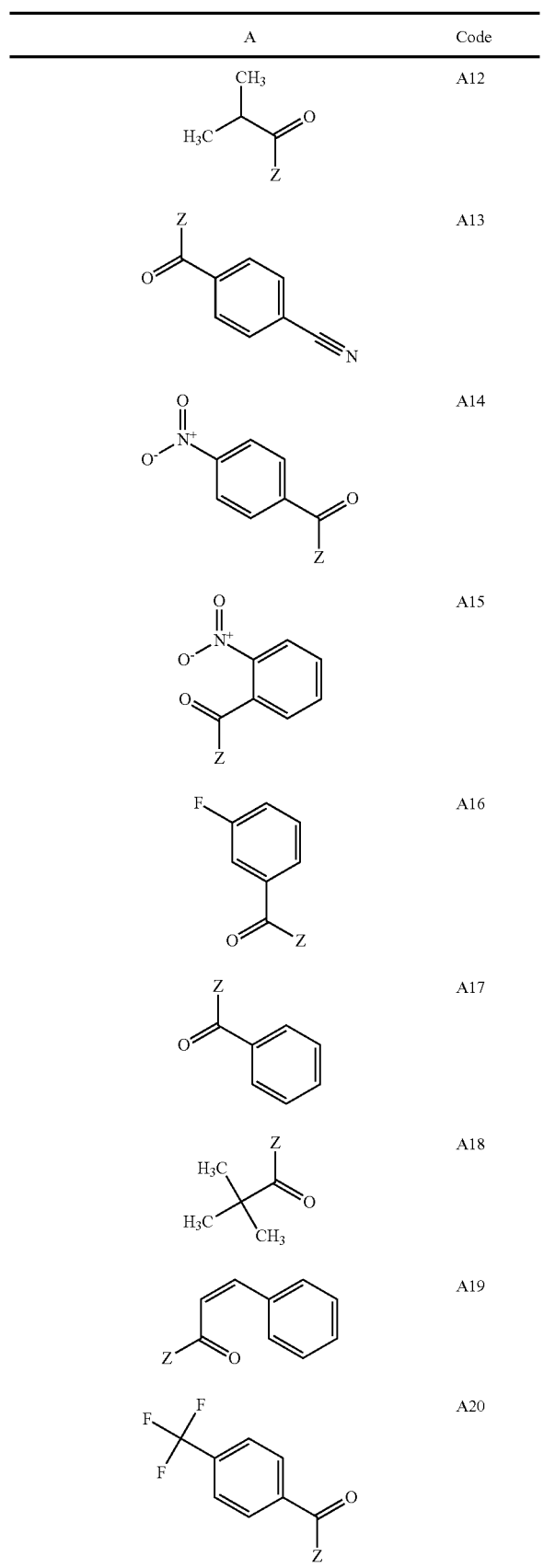 | A12 |
| | A13 |
| | A14 |
| | A15 |
| | A16 |
| | A17 |
| | A18 |
| | A19 |
| | A20 |
TABLE I-continued
| A | Code |
|---|---|
| 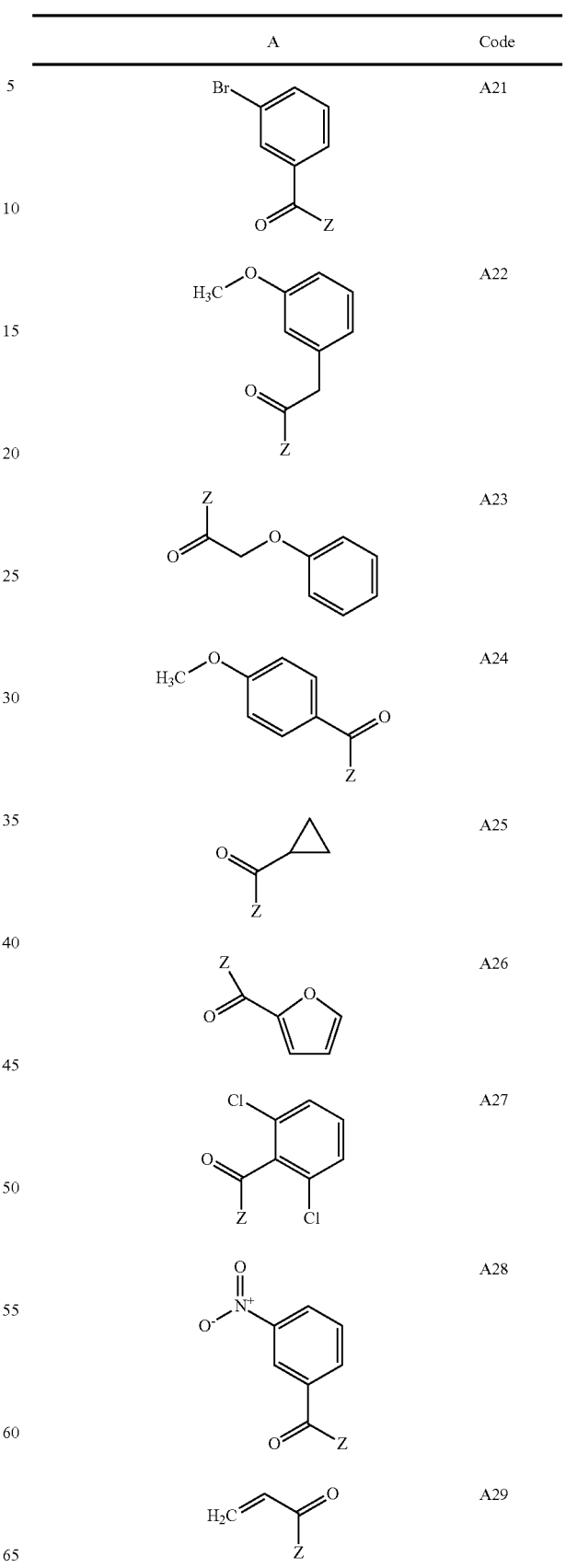 | A21 |
| | A22 |
| | A23 |
| | A24 |
| | A25 |
| | A26 |
| | A27 |
| | A28 |
| | A29 |

TABLE I-continued
| A | Code |
|---|---|
| 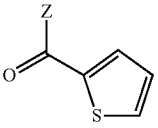 | A30 |
| 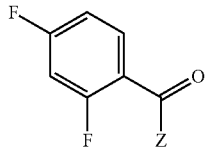 | A31 |
| 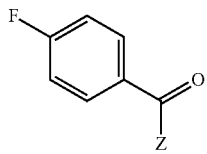 | A32 |
| 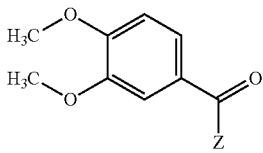 | A33 |
| 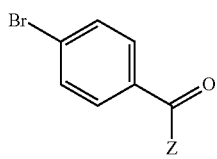 | A34 |
| 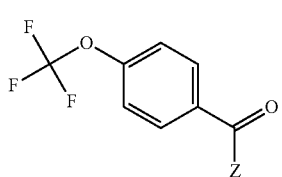 | A35 |
| 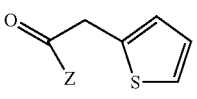 | A36 |
| 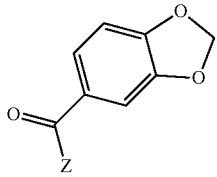 | A37 |
| 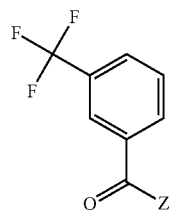 | A38 |
| 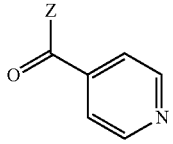 | A39 |
| 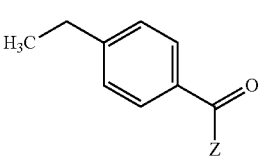 | A40 |
| 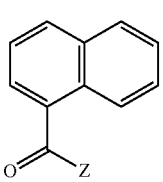 | A41 |
| 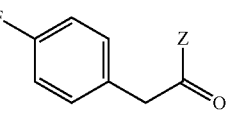 | A42 |
| 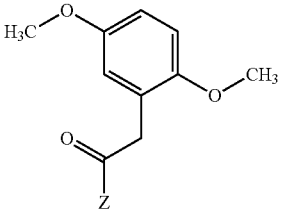 | A43 |
| 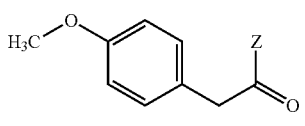 | A44 |
| 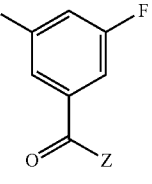 | A45 |
| 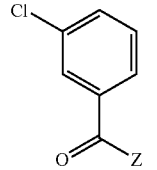 | A46 |
| 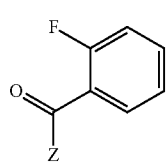 | A47 |

TABLE I-continued
| A | Code |
|---|---|
| 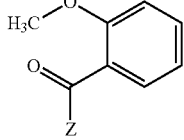 | A48 |
| 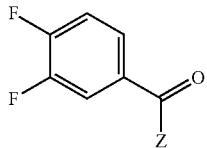 | A49 |
| 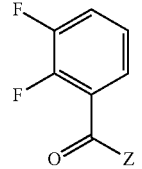 | A50 |
|  | A51 |
| 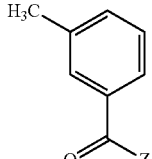 | A52 |
| 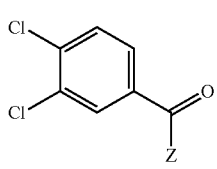 | A53 |
| 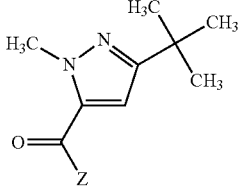 | A54 |
| 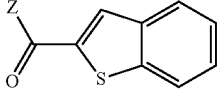 | A55 |
| 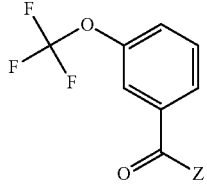 | A56 |
| 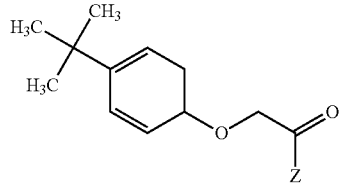 | A57 |
| 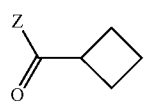 | A58 |
| 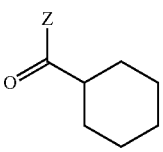 | A59 |
| 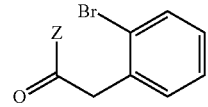 | A60 |
| 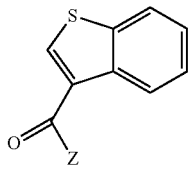 | A61 |
| 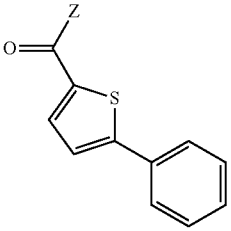 | A62 |
| 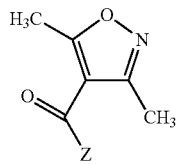 | A63 |
| 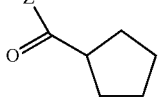 | A64 |
| 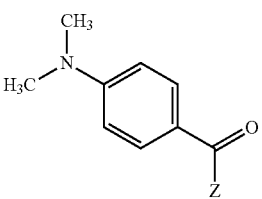 | A65 |

TABLE I-continued
| A | Code |
|---|---|
| 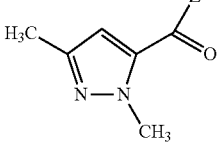 | A66 |
| 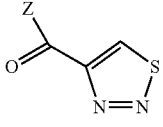 | A67 |
| 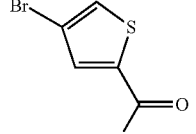 | A68 |
| 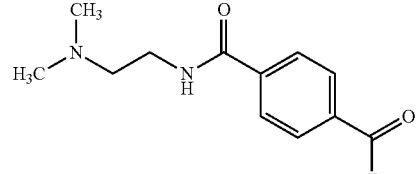 | A69 |
| 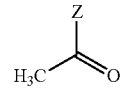 | A70 |
| 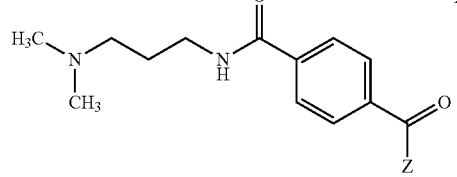 | A71 |
| 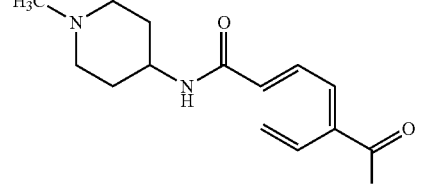 | A72 |
|  | A73 |
| 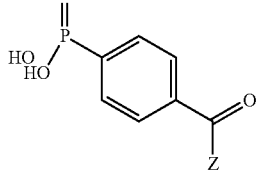 | A74 |
| 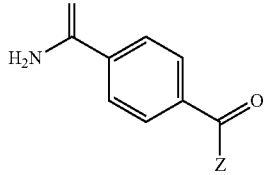 | A75 |
| 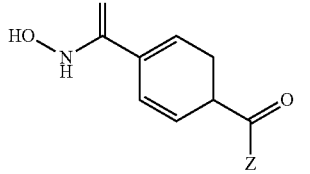 | A76 |
| 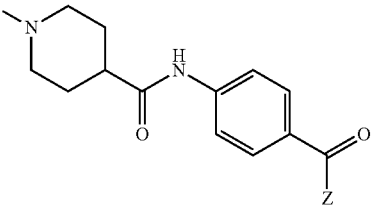 | A77 |
| 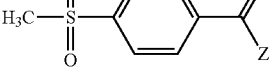 | A78 |
| 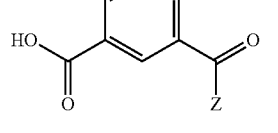 | A79 |
| 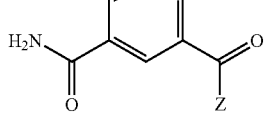 | A80 |
| 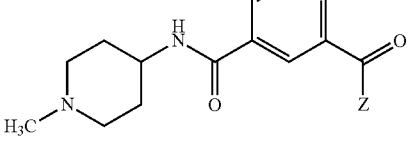 | A81 |
| 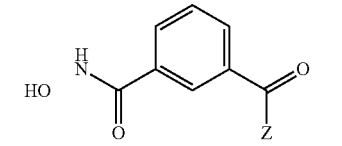 | A82 |
| 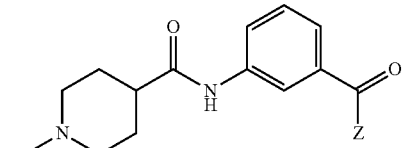 | A83 |

TABLE I-continued
| A | Code |
|---|---|
| 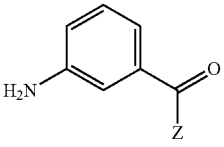 | A84 |
| 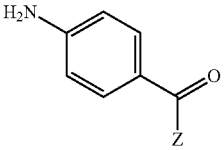 | A85 |
| 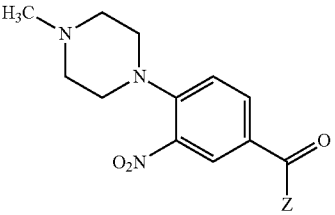 | A86 |
| 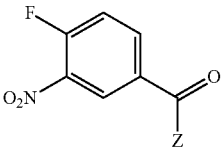 | A87 |
| 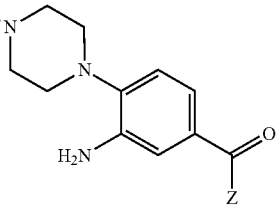 | A88 |
| 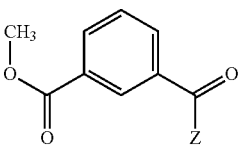 | A89 |
| 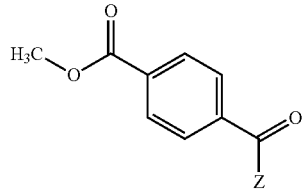 | A90 |
| 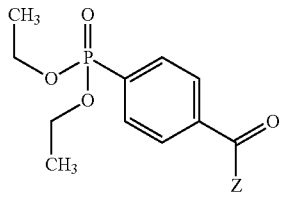 | A91 |
TABLE I-continued
| A | Code |
|---|---|
| 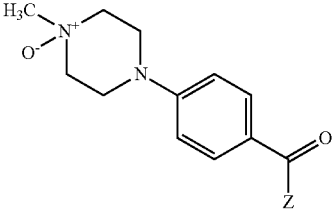 | A92 |
| 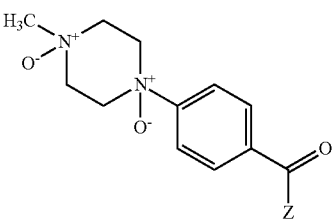 | A93 |
TABLE II
| B | Code |
|---|---|
| 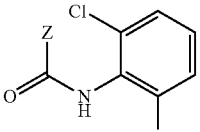 | B1 |
| 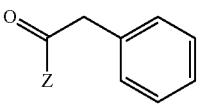 | B2 |
| 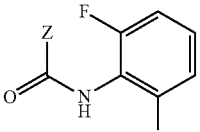 | B3 |
| 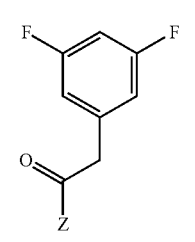 | B4 |
| 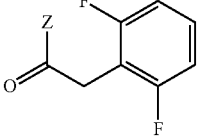 | B5 |
| 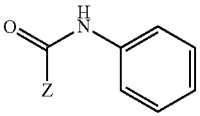 | B6 |

TABLE II-continued
| B | Code |
|---|---|
| 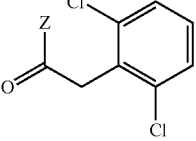 | B7 |
| 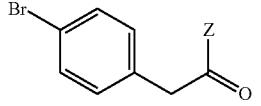 | B8 |
| 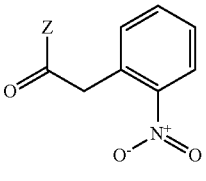 | B9 |
| 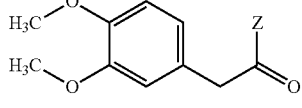 | B10 |
| 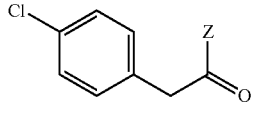 | B11 |
| 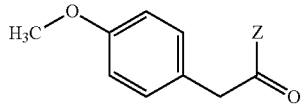 | B12 |
| 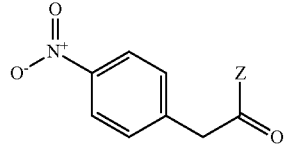 | B13 |
| 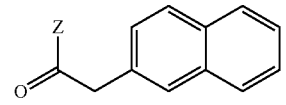 | B14 |
| 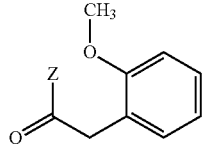 | B15 |
| 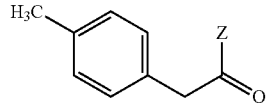 | B16 |
| 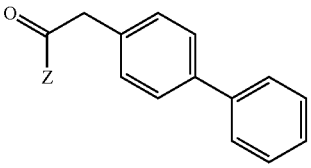 | B17 |
| 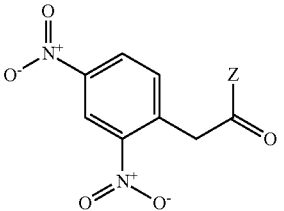 | B18 |
| 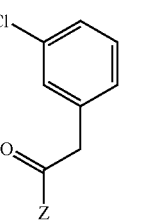 | B19 |
| 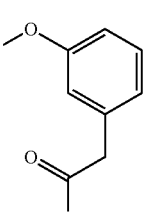 | B20 |
| 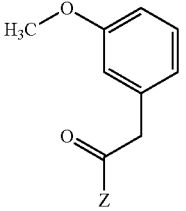 | B21 |
| 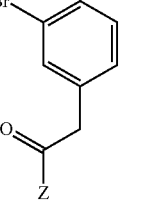 | B22 |
| 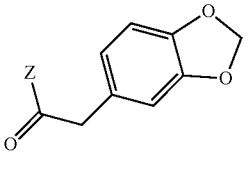 | B23 |
| 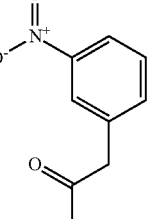 | B24 |

TABLE II-continued
| B | Code |
|---|---|
| 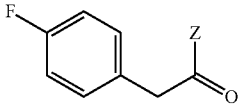 | B25 |
| 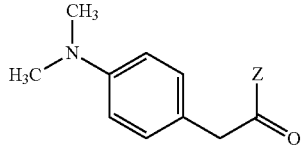 | B26 |
| 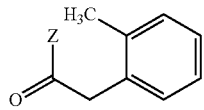 | B27 |
| 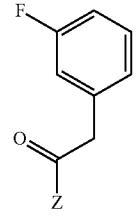 | B28 |
| 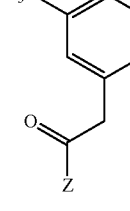 | B29 |
| 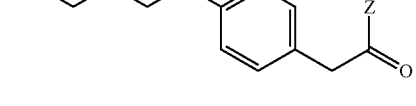 | B30 |
| 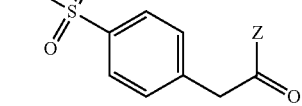 | B31 |
| 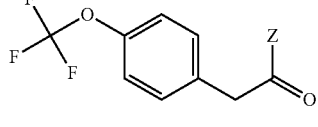 | B32 |
| 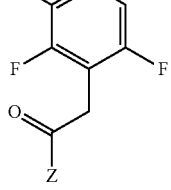 | B33 |
| 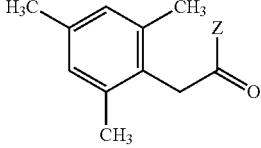 | B34 |
| 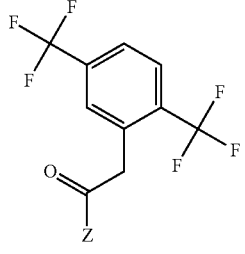 | B35 |
| 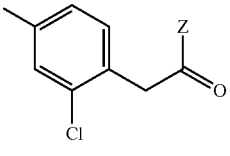 | B36 |
| 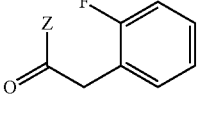 | B37 |
| 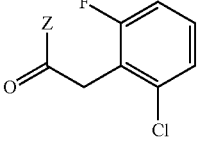 | B38 |
| 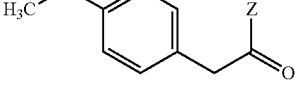 | B39 |
| 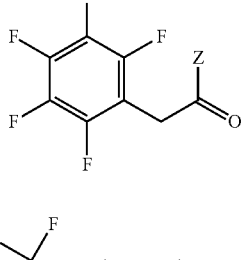 | B40 |
| 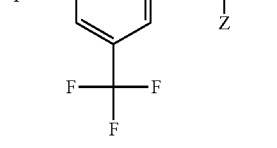 | B41 |

TABLE II-continued
| B | Code |
|---|---|
| 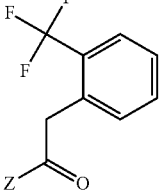 | B42 |
| 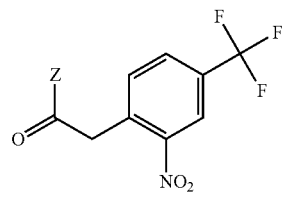 | B43 |
| 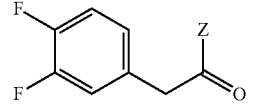 | B44 |
| 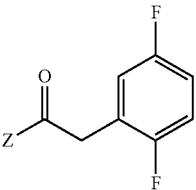 | B45 |
| 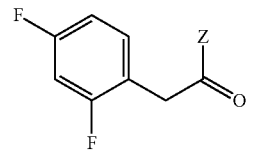 | B46 |
| 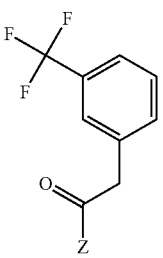 | B47 |
| 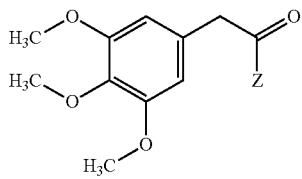 | B48 |
| 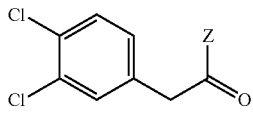 | B49 |
| 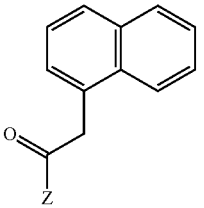 | B50 |
| 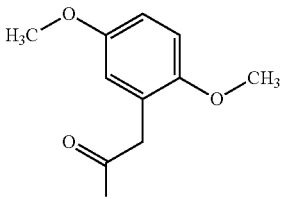 | B51 |
| 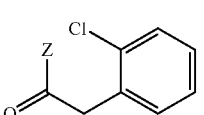 | B52 |
| 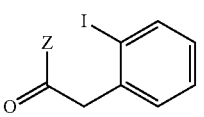 | B53 |
| 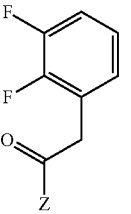 | B54 |
| 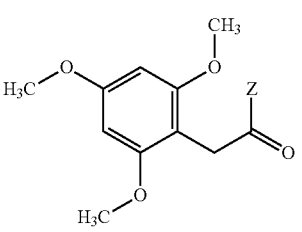 | B55 |
| 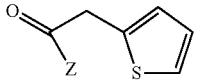 | B56 |
| 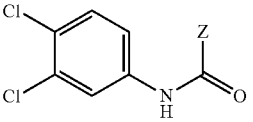 | B57 |
| 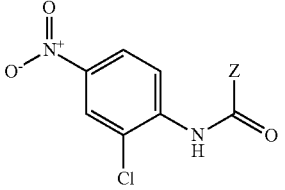 | B58 |

TABLE II-continued
| B | Code |
|---|---|
| 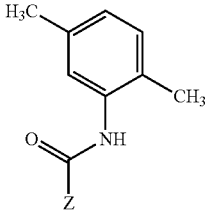 | B59 |
| 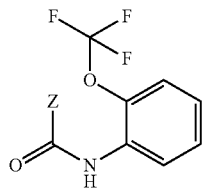 | B60 |
| 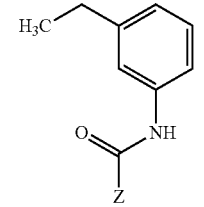 | B61 |
| 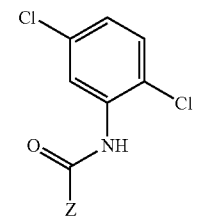 | B62 |
| 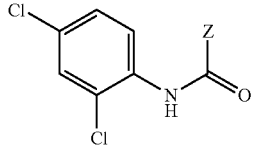 | B63 |
| 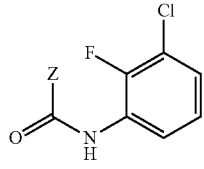 | B64 |
| 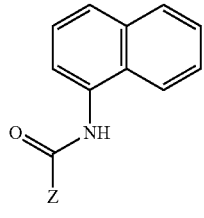 | B65 |
| 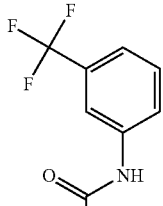 | B66 |
| 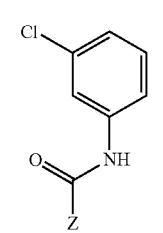 | B67 |
| 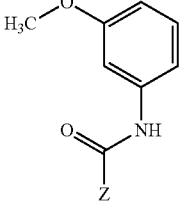 | B68 |
| 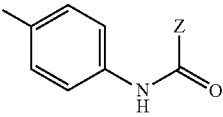 | B69 |
| 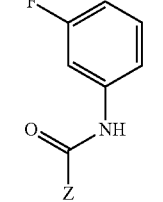 | B70 |
| 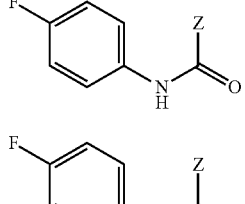 | B71 |
| 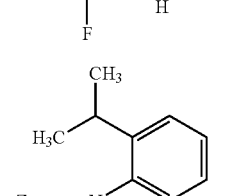 | B72 |
| 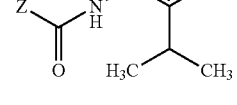 | B73 |

TABLE II-continued
| B | Code |
|---|---|
|  | B74 |
|  | B75 |
|  | B76 |
|  | B77 |
|  | B78 |
|  | B79 |
|  | B80 |
|  | B81 |
|  | B82 |
| 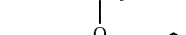 | B83 |
| | B84 |
| | B85 |
| | B86 |
| | B87 |
| | B88 |
| | B89 |
| | B90 |
| | B91 |

TABLE II-continued
| B | Code |
|---|---|
| 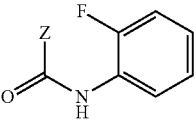 | B92 |
| 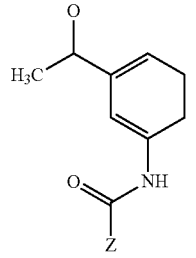 | B93 |
| 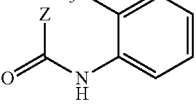 | B94 |
| 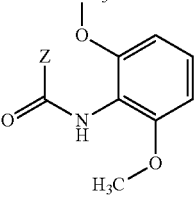 | B95 |
| 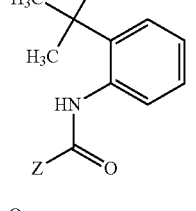 | B96 |
| 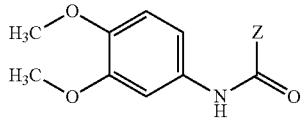 | B97 |
| 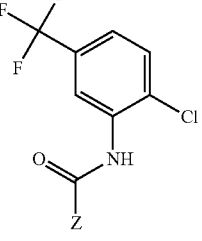 | B98 |
| 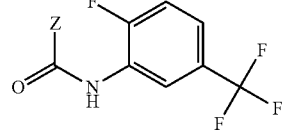 | B99 |
| 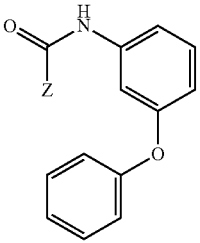 | B100 |
| 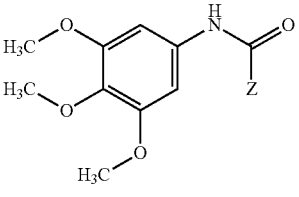 | B101 |
| 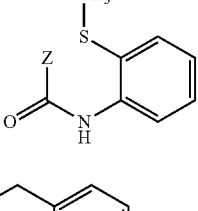 | B102 |
| 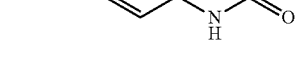 | B103 |
| 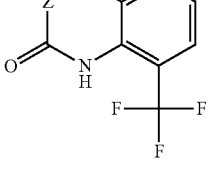 | B104 |
| 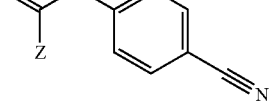 | B105 |
| 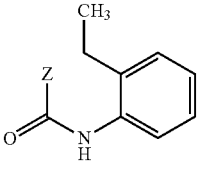 | B106 |
| 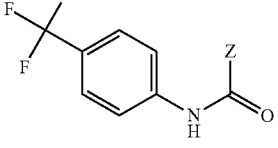 | B107 |

TABLE II-continued
| B | Code |
|---|---|
| 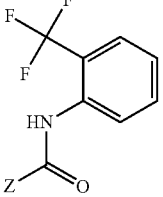 | B108 |
| 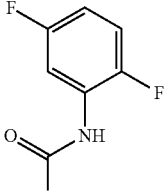 | B109 |
| 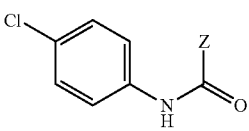 | B110 |
| 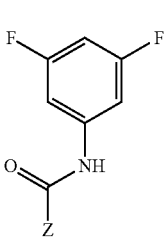 | B111 |
| 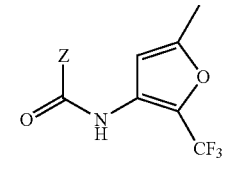 | B112 |
| 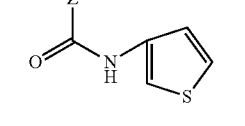 | B113 |
| 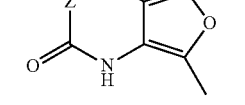 | B114 |
| 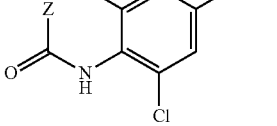 | B115 |
|  | B116 |
| 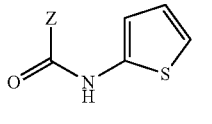 | B117 |
| 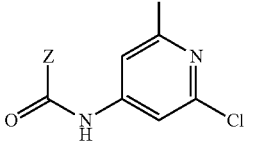 | B118 |
| 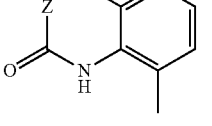 | B119 |
| 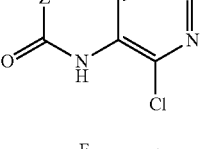 | B120 |
| 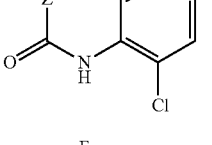 | B121 |
| 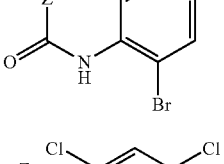 | B122 |
| 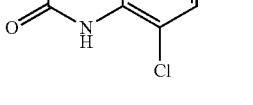 | B123 |
| 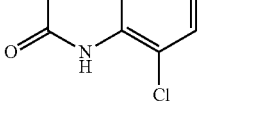 | B124 |
| 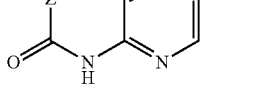 | B125 |

TABLE II-continued

| B | Code |
|---|---|
| (structure: Z-C(=O)-NH- attached to benzene ring with 2,6-diCl and 4-SO₂NH₂) | B126 |
| (structure: Z-C(=O)-NH- attached to pyridine ring with Cl, F, Cl, F substituents) | B127 |
| (structure: Z-C(=O)-NH- attached to benzene ring with 2,6-diCl and 4-OCF₃) | B128 |

As said above the following Table III shows all the compounds conveniently and unambiguously identified through a coding system.

TABLE III

| N° | CODE |
|---|---|
| 1 | A1-Z-B1 |
| 2 | A1-Z-B2 |
| 3 | A1-Z-B3 |
| 4 | A1-Z-B4 |
| 5 | A1-Z-B5 |
| 6 | A2-Z-B1 |
| 7 | A3-Z-B1 |
| 8 | A1-Z-B6 |
| 9 | A1-Z-B7 |
| 10 | A1-Z-B8 |
| 11 | A1-Z-B9 |
| 12 | A1-Z-B10 |
| 13 | A1-Z-B11 |
| 14 | A1-Z-B12 |
| 15 | A1-Z-B13 |
| 16 | A1-Z-B14 |
| 17 | A1-Z-B15 |
| 18 | A1-Z-B16 |
| 19 | A1-Z-B17 |
| 20 | A1-Z-B18 |
| 21 | A1-Z-B19 |
| 22 | A1-Z-B20 |
| 23 | A1-Z-B21 |
| 24 | A1-Z-B22 |
| 25 | A1-Z-B23 |
| 26 | A1-Z-B24 |
| 27 | A1-Z-B25 |
| 28 | A1-Z-B26 |
| 29 | A1-Z-B27 |
| 30 | A1-Z-B28 |
| 31 | A1-Z-B29 |
| 32 | A1-Z-B30 |
| 33 | A1-Z-B31 |
| 34 | A1-Z-B32 |
| 35 | A1-Z-B33 |
| 36 | A1-Z-B34 |
| 37 | A1-Z-B35 |
| 38 | A1-Z-B36 |
| 39 | A1-Z-B37 |
| 40 | A1-Z-B38 |
| 41 | A1-Z-B39 |
| 42 | A1-Z-B40 |
| 43 | A1-Z-B41 |
| 44 | A1-Z-B42 |
| 45 | A1-Z-B43 |
| 46 | A1-Z-B44 |
| 47 | A1-Z-B45 |
| 48 | A1-Z-B46 |
| 49 | A1-Z-B47 |
| 50 | A1-Z-B48 |
| 51 | A1-Z-B49 |
| 52 | A1-Z-B50 |
| 53 | A1-Z-B51 |
| 54 | A1-Z-B52 |
| 55 | A1-Z-B53 |
| 56 | A1-Z-B54 |
| 57 | A1-Z-B55 |
| 58 | A4-Z-B1 |
| 59 | A2-Z-B5 |
| 60 | A1-Z-B56 |
| 61 | A5-Z-B5 |
| 62 | A6-Z-B5 |
| 63 | A7-Z-B1 |
| 64 | A8-Z-B1 |
| 65 | A9-Z-B1 |
| 66 | A10-Z-B1 |
| 67 | A11-Z-B1 |
| 68 | A12-Z-B1 |
| 69 | A13-Z-B1 |
| 70 | A14-Z-B1 |
| 71 | A15-Z-B1 |
| 72 | A16-Z-B1 |
| 73 | A17-Z-B1 |
| 74 | A18-Z-B1 |
| 75 | A19-Z-B1 |
| 76 | A20-Z-B1 |
| 77 | A21-Z-B1 |
| 78 | A22-Z-B1 |
| 79 | A23-Z-B1 |
| 80 | A24-Z-B1 |
| 81 | A25-Z-B1 |
| 82 | A26-Z-B1 |
| 83 | A27-Z-B1 |
| 84 | A28-Z-B1 |
| 85 | A29-Z-B1 |
| 86 | A30-Z-B1 |
| 87 | A31-Z-B1 |
| 88 | A32-Z-B1 |
| 89 | A33-Z-B1 |
| 90 | A34-Z-B1 |
| 91 | A35-Z-B1 |
| 92 | A36-Z-B1 |
| 93 | A36-Z-B5 |
| 94 | A37-Z-B5 |
| 95 | A38-Z-B5 |
| 96 | A39-Z-B5 |
| 97 | A40-Z-B5 |
| 98 | A41-Z-B5 |
| 99 | A42-Z-B5 |
| 100 | A43-Z-B5 |
| 101 | A44-Z-B5 |
| 102 | A45-Z-B5 |
| 103 | A46-Z-B5 |
| 104 | A47-Z-B5 |
| 105 | A48-Z-B5 |
| 106 | A4-Z-B5 |
| 107 | A49-Z-B5 |
| 108 | A50-Z-B5 |
| 109 | A51-Z-B5 |
| 110 | A52-Z-B5 |
| 111 | A53-Z-B5 |
| 112 | A54-Z-B5 |
| 113 | A55-Z-B5 |
| 114 | A56-Z-B5 |
| 115 | A57-Z-B5 |
| 116 | A58-Z-B5 |
| 117 | A59-Z-B5 |
| 118 | A60-Z-B5 |
| 119 | A61-Z-B5 |
| 120 | A62-Z-B5 |

TABLE III-continued

| N° | CODE |
|---|---|
| 121 | A63-Z-B5 |
| 122 | A64-Z-B5 |
| 123 | A65-Z-B5 |
| 124 | A66-Z-B5 |
| 125 | A67-Z-B5 |
| 126 | A68-Z-B5 |
| 127 | A6-Z-B1 |
| 128 | A69-Z-B5 |
| 129 | A1-Z-B57 |
| 130 | A1-Z-B58 |
| 131 | A1-Z-B59 |
| 132 | A1-Z-B60 |
| 133 | A1-Z-B61 |
| 134 | A1-Z-B62 |
| 135 | A1-Z-B63 |
| 136 | A1-Z-B64 |
| 137 | A1-Z-B65 |
| 138 | A1-Z-B66 |
| 139 | A1-Z-B67 |
| 140 | A1-Z-B68 |
| 141 | A1-Z-B69 |
| 142 | A1-Z-B70 |
| 143 | A1-Z-B71 |
| 144 | A1-Z-B72 |
| 145 | A1-Z-B73 |
| 146 | A1-Z-B74 |
| 147 | A1-Z-B75 |
| 148 | A1-Z-B76 |
| 149 | A1-Z-B77 |
| 150 | A1-Z-B78 |
| 151 | A1-Z-B79 |
| 152 | A1-Z-B80 |
| 153 | A1-Z-B81 |
| 154 | A1-Z-B82 |
| 155 | A1-Z-B83 |
| 156 | A1-Z-B84 |
| 157 | A1-Z-B85 |
| 158 | A1-Z-B86 |
| 159 | A1-Z-B87 |
| 160 | A1-Z-B88 |
| 161 | A1-Z-B89 |
| 162 | A1-Z-B90 |
| 163 | A1-Z-B91 |
| 164 | A1-Z-B92 |
| 165 | A1-Z-B93 |
| 166 | A1-Z-B94 |
| 167 | A1-Z-B95 |
| 168 | A1-Z-B96 |
| 169 | A1-Z-B97 |
| 170 | A1-Z-B98 |
| 171 | A1-Z-B99 |
| 172 | A1-Z-B100 |
| 173 | A1-Z-B101 |
| 174 | A1-Z-B102 |
| 175 | A1-Z-B103 |
| 176 | A1-Z-B104 |
| 177 | A1-Z-B105 |
| 178 | A1-Z-B106 |
| 179 | A1-Z-B107 |
| 180 | A1-Z-B108 |
| 181 | A1-Z-B109 |
| 182 | A1-Z-B110 |
| 183 | A1-Z-B111 |
| 184 | A1-Z-B112 |
| 185 | A89-Z-B1 |
| 186 | A90-Z-B1 |
| 187 | A51-Z-B1 |
| 188 | A52-Z-B1 |
| 189 | A53-Z-B1 |
| 190 | A55-Z-B1 |
| 191 | A56-Z-B1 |
| 192 | A57-Z-B1 |
| 193 | A58-Z-B1 |
| 194 | A59-Z-B1 |
| 195 | A60-Z-B1 |
| 196 | A61-Z-B1 |
| 197 | A62-Z-B1 |
| 198 | A63-Z-B1 |
| 199 | A64-Z-B1 |
| 200 | A66-Z-B1 |
| 201 | A67-Z-B1 |
| 202 | A68-Z-B1 |
| 203 | A7-Z-B5 |
| 204 | A8-Z-B5 |
| 205 | A9-Z-B5 |
| 206 | A10-Z-B5 |
| 207 | A11-Z-B5 |
| 208 | A12-Z-B5 |
| 209 | A13-Z-B5 |
| 210 | A14-Z-B5 |
| 211 | A15-Z-B5 |
| 212 | A16-Z-B5 |
| 213 | A70-Z-B5 |
| 214 | A17-Z-B5 |
| 215 | A18-Z-B5 |
| 216 | A19-Z-B5 |
| 217 | A20-Z-B5 |
| 218 | A21-Z-B5 |
| 219 | A22-Z-B5 |
| 220 | A23-Z-B5 |
| 221 | A24-Z-B5 |
| 222 | A25-Z-B5 |
| 223 | A26-Z-B5 |
| 224 | A27-Z-B5 |
| 225 | A28-Z-B5 |
| 226 | A29-Z-B5 |
| 227 | A30-Z-B5 |
| 228 | A31-Z-B5 |
| 229 | A32-Z-B5 |
| 230 | A33-Z-B5 |
| 231 | A34-Z-B5 |
| 232 | A35-Z-B5 |
| 233 | A71-Z-B5 |
| 234 | A72-Z-B5 |
| 235 | A71-Z-B1 |
| 236 | A17-Z-B6 |
| 237 | A17-Z-B2 |
| 238 | A72-Z-B1 |
| 239 | A73-Z-B1 |
| 240 | A96-Z-B1 |
| 241 | A75-Z-B1 |
| 242 | A76-Z-B1 |
| 243 | A77-Z-B1 |
| 244 | A78-Z-B1 |
| 245 | A79-Z-B1 |
| 246 | A80-Z-B1 |
| 247 | A81-Z-B1 |
| 248 | A82-Z-B1 |
| 249 | A83-Z-B1 |
| 250 | A84-Z-B1 |
| 251 | A85-Z-B1 |
| 252 | A86-Z-B1 |
| 253 | A87-Z-B1 |
| 254 | A88-Z-B1 |
| 255 | A91-Z-B1 |
| 256 | A74-Z-B1 |
| 257 | A92-Z-B1 |
| 258 | A93-Z-B1 |
| 259 | A1-Z-B113 |
| 260 | A1-Z-B114 |
| 261 | A1-Z-B115 |
| 262 | A1-Z-B116 |
| 263 | A1-Z-B117 |
| 264 | A1-Z-B118 |
| 265 | A1-Z-B119 |
| 266 | A1-Z-B120 |
| 267 | A1-Z-B121 |
| 268 | A1-Z-B122 |
| 269 | A1-Z-B123 |
| 270 | A1-Z-B124 |
| 271 | A1-Z-B125 |
| 272 | A1-Z-B126 |

TABLE III-continued

| N° | CODE |
|---|---|
| 273 | A1-Z-B127 |
| 274 | A1-Z-B128 |
| 275 | A94-Z-B1 |
| 276 | A95-Z-B1 |

Example 1

6,6-Dimethyl-3-[4-(4-methyl-piperazin-1-yl)-benzoylamino]-4,6-dihydro-1H-pyrrolo[3,4-c]pyrazole-2,5-dicarboxylic acid 5-tert-butyl ester 2-ethyl ester Formula (IV), R=4-(4-methyl-piperazin)-phenyl To a solution of 3-Amino-6,6-dimethyl-4H,6H-pyrrolo[3,4-c]pyrazole-2,5-dicarboxylic acid 5-tert-butyl ester 2-ethyl ester (2.50 g, 7.70 mmol) prepared as reported in WO2004/056827, N,N-diisopropylethylamine (14.6 ml, 33.6 mmol) in anhydrous Dioxane (100 ml), 4-(4-Methyl-piperazin-1-yl)-benzoyl chloride (0.24 g, 1.00 mmol) was added. The reaction was heated to reflux and stirred for 6 h. The solvent was removed under vacuum, the residue dissolved in $CH_2Cl_2$ (150 mL) and washed with brine (1×100 mL). The organic phase was dried over sodium sulphate, the solvent evaporated in vacuo and the residue purified by flash chromatography (Acetone/DCM 80/20) affording 2.10 g (yield 52%) of the title compound.

ESI MS: m/z 527 ($MH^+$);
$^1$H NMR (400 MHz, DMSO-$d_6$): δ 10.69 (s, 1H), 7.76 (m, 2H), 7.09 (m, 2H), 4.55 (d, 2H, J=9.8 Hz), 4.48 (q, 2H, J=7.1 Hz), 3.34 (m, 4H), 2.52 (m, 4H), 2.27 (s, 3H), 1.64 (s, 3H), 1.62 (s, 3H), 1.47 (s, 9H), 1.38 (t, 3H, J=7.1 Hz).

By working in an analogous manner the following compounds were prepared:

3-[2-[(2-Methoxy-ethyl)-(2,2,2-trifluoro-acetyl)-amino]-4-(4-methyl-piperazin-1-yl)-benzoylamino]-6,6-dimethyl-4,6-dihydro-pyrrolo[3,4-c]pyrazole-1,5-dicarboxylic acid 5-tert-butyl ester 1-ethyl ester Formula (IV), R=2-[(2-Methoxy-ethyl)-(2,2,2-trifluoro-acetyl)-amino]-4-(4-methyl-piperazin)-phenyl, Q=carboxyethyl ESI MS: m/z 696 ($MH^+$);
$^1$H NMR (400 MHz, DMSO-$d_6$) δ ppm 1.35 (t, J=7.07 Hz, 3H) 1.42-1.45 (m, 9H) 1.71-1.78 (m, 6H) 2.23 (s, 3H) 2.41-2.48 (m, 4H) 3.16 (s, 3H) 3.28-3.35 (m, 4 H) 3.37-3.54 (m, 4H) 4.28-4.38 (m, 2H) 4.43 (q, J=6.99 Hz, 2H) 6.92-6.94 (m, 1H) 6.98-7.04 (m, 1H) 7.77 (dd, J=8.90, 3.90 Hz, 1H) 11.21 (s, 1H)

6,6-Dimethyl-3-[4-(4-methyl-piperazin-1-yl)-2-nitro-benzoylamino]-4,6-dihydro-pyrrolo[3,4-c]pyrazole-1,5-dicarboxylic acid 5-tert-butyl ester 1-ethyl ester Formula (IV),
R=2-nitro-4-(4-methyl-piperazin)-phenyl,
Q=carboxyethyl ESI MS: m/z 696 ($MH^+$);
$^1$H NMR (400 MHz, DMSO-$d_6$) δ ppm 1.35 (t, J=7.13 Hz, 3H) 1.44 (s, 9H) 1.77 (s, 6H) 2.24 (s, 3H) 2.42-2.48 (m, 4H) 3.34-3.39 (m, 4H) 4.40 (d, J=8.66 Hz, 2H) 4.42-4.47 (m, 2H) 7.22 (dd, J=8.90, 2.19 Hz, 1H) 7.41-7.43 (m, 1H) 7.60 (d, J=8.78 Hz, 1H) 11.57 (s, 1H).

3-[2-K(S)-2-Methoxy-1-methyl-ethyl)-(2,2,2-trifluoro-acetyl)-amino]-4-(4-methyl-piperazin-1-yl)-benzoylamino]-6,6-dimethyl-4,6-dihydro-pyrrolo[3,4-c]pyrazole-1,5-dicarboxylic acid 5-tert-butyl ester 1-ethyl ester Formula (IV), R=2-[((S)-2-Methoxy-1-methyl-ethyl)-(2,2,2-trifluoro-acetyl)-amino]-4-(4-methyl-piperazin)-phenyl, Q=carboxyethyl ESI MS: m/z 710 ($MH^+$);

Example 2

6,6-Dimethyl-3-[4-(4-methyl-piperazin-1-yl)-benzoylamino]-5,6-dihydro-4H-pyrrolo[3,4-c]pyrazole-2-carboxylic acid ethyl ester dihydrochloride Formula (V), R=4-(4-methyl-piperazin-1-yl)-phenyl A suspension of 6,6-Dimethyl-3-[4-(4-methyl-piperazin-1-yl)-benzoylamino]-4,6-dihydro-1H-pyrrolo[3,4-c]pyrazole-2,5-dicarboxylic acid 5-tert-butyl ester 2-ethyl ester (1.5 g, 2.84 mmol) in 5M HCl in dioxane (20 mL) was stirred at room temperature for 6 h, the solvent was removed in vacuo and the residue treated with ether (30 mL). The suspension was stirred for 30' then the organic solvent was allowed by filtration yielding 1.27 g (yield 90%) of the title compound as white solid ESI MS: m/z 427 ($MH^+$);
$^1$H NMR (400 MHz, DMSO-$d_6$): δ 11.39 (s, 1H), 10.68 (bs, 1H), 10.22 (bs, 2H), 8.00 (m, 2H), 7.10 (m, 2H), 4.51 (m, 2H), 4.46 (q, 2H, J=7.1 Hz), 3.42-3.35 (m, 8H), 2.84 (m, 3H), 1.80 (s, 6H), 1.37 (t, 3H, J=7.1 Hz).

By working in an analogous manner the following compounds were prepared:

3-Amino-6,6-dimethyl-5,6-dihydro-4H-pyrrolo[3,4-c]pyrazole-2-carboxylic acid ethyl ester dihydrochloride Formula (X)

ESI MS: m/z 225 ($MH^+$);
$^1$H NMR (400 MHz, DMSO-$d_6$): δ 9.75 (s, 3H), 6.77 (bs, 2H), 4.38 (q, 2H, J=7.1 Hz), 4.12 (t, 2H, J=5.0 Hz), 1.60 (s, 6H), 1.33 (t, 3H, J=7.1 Hz).

6,6-Dimethyl-3-[4-(4-methyl-piperazin-1-yl)-2-nitro-benzoylamino]-5,6-dihydro-4H-pyrrolo[3,4-c]pyrazole-1-carboxylic acid ethyl ester dihydrochloride Formula (V),
R=2-nitro-4-(4-methyl-piperazin)-phenyl ESI MS: m/z 472 ($MH^+$);
$^1$H NMR (400 MHz, DMSO-$d_6$) δ ppm 1.35 (t, J=7.13 Hz, 3H) 1.79 (s, 6H) 2.83 (d, J=4.27 Hz, 3H) 3.07-3.19 (m, 2H) 3.29 (t, J=12.56 Hz, 2H) 3.45-3.55 (m, 4H) 4.12 (d, J=13.78 Hz, 2H) 4.41-4.43 (m, 2H) 4.45 (q, J=7.07 Hz, 1H) 7.31 (dd, J=8.90, 2.56 Hz, 1H) 7.55 (d, J=2.56 Hz, 1H) 7.70 (d, J=8.78 Hz, 1H) 10.17 (br. s., 1H) 10.70 (br. s., 1H) 11.85 (s, 1H).

3-[2-[(2-Methoxy-ethyl)-(2,2,2-trifluoro-acetyl)-amino]-4-(4-methyl-piperazin-1-yl)-benzoylamino]-6,6-dimethyl-5,6-dihydro-4H-pyrrolo[3,4-c]pyrazole-1-carboxylic acid ethyl ester dihydrochloride Formula (V), R=2-[(2-Methoxy-ethyl)-(2,2,2-trifluoro-acetyl)-amino]-4-(4-methyl-piperazin)-phenyl ESI MS: m/z 596 (MH+);

3-[2-[((S)-2-Methoxy-1-methyl-ethyl)-(2,2,2-trifluoro-acetyl)-amino]-4-(4-methyl-piperazin-1-yl)-benzoylamino]-6,6-dimethyl-5,6-dihydro-4H-pyrrolo[3,4-c]pyrazole-1-carboxylic acid ethyl ester dihydrochloride Formula (V), R=2-[((S)-2-Methoxy-1-methyl-ethyl)-(2,2,2-trifluoro-acetyl)-amino]-4-(4-methyl-piperazin)-phenyl ESI MS: m/z 609 (MH+).

Example 3

5-(2,6-Dichloro-phenylcarbamoyl)-6,6-dimethyl-3-[4-(4-methyl-piperazin-1-yl)-benzoylamino]-5,6-dihydro-4H-pyrrolo[3,4-c]pyrazole-2-carboxylic acid ethyl ester Formula (VII), R=4-(4-methyl-piperazin)-phenyl, Ar=2,6-dichlorophenyl, A=NH To a solution of 6,6-Dimethyl-3-[4-(4-methyl-piperazin-1-yl)-benzoylamino]-5,6-dihydro-4H-pyrrolo[3,4-c]pyrazole-2-carboxylic acid ethyl ester dihydrochloride (0.60 g, 1.20 mmol) N,N-diispropylethylamine (0.41 ml, 2.40 mmol) in dry $CH_2Cl_2$ (100 mL), a solution of 1,3-dichlorophenyl isocyanate (0.14 g, 0.75 mmol) in dry $CH_2Cl_2$ (10 mL) was slowly added. The reaction was stirred at room temperature over night, then the solvent removed under reduced pressure, the residue dissolved in DCM (40 mL) and washed with water (1×20 mL). The organic phase was dried over sodium sulphate, the solvent evaporated in vacuo, the residue suspended in ethyl ether (50 ml) and stirred for 30'. The organic phase was removed under filtration yielding 0.6 g (yield 81%) of the title compound.

ESI MS: m/z 614 (MH+);
$^1$H NMR (400 MHz, DMSO-$d_6$): δ 10.74 (s, 1H), 8.30 (s, 1H), 7.84 (m, 2H), 7.52 (m, 2H), 7.31 (m, 1H), 7.15 (m, 2H), 4.83 (s, 2H), 4.49 (q, 2H, J=7.0 Hz), 3.32 (m, 4H), 2.53 (s, 3H), 250 (m, 4H), 1.69 (s, 6H), 1.40 (t, 3H, J=7.0 Hz).

By working in an analogous manner the following compounds were prepared:

5-(2,6-Dichloro-phenylcarbamoyl)-6,6-dimethyl-3-[4-(4-methyl-piperazin-1-yl)-2-nitro-benzoylamino]-5,6-dihydro-4H-pyrrolo[3,4-c]pyrazole-1-carboxylic acid ethyl ester Formula (VII), R=2-nitro-4-(4-methyl-piperazin)-phenyl, Ar=2,6-dichlorophenyl, A=NH ESI MS: m/z 659 (MH+)
$^1$H NMR (400 MHz, DMSO-$d_6$) δ ppm 1.35 (t, J=7.13 Hz, 3H), 1.82 (s, 6H), 2.22 (s, 3H), 2.39-3.47 (m, 4H), 3.33-3.40 (m, 4H), 4.44 (q, J=7.13 Hz, 2H), 4.69 (s, 2H), 7.21 (dd, J=8.90 and 2.56 Hz, 1H), 7.28 (t, J=7.98 Hz, 1H), 7.41 (d, J=2.56 Hz, 1H), 7.48 (d, J=7.98 Hz, 2H), 7.62 (d, J=8.90 Hz, 1H), 8.24 (s, 1H), 11.62 (s, 1H).

5-(2,6-Dichloro-phenylcarbamoyl)-3-[2-[(2-methoxy-ethyl)-(2,2,2-trifluoro-acetyl)-amino]-4-(4-methyl-piperazin-1-yl)-benzoylamino]-6,6-dimethyl-5,6-dihydro-4H-pyrrolo[3,4-c]pyrazole-1-carboxylic acid ethyl ester Formula (VII), [formula (IV), R=2-[(2-Methoxy-ethyl)-(2,2,2-trifluoro-acetyl)-amino]-4-(4-methyl-piperazin)-phenyl, Ar=2,6-dichlorophenyl, A=NH]

ESI MS: m/z 783 (MH+).

5-(2,6-Dichloro-phenylcarbamoyl)-3-[2-[((S)-2-methoxy-1-methyl-ethyl)-(2,2,2-trifluoro-acetyl)-amino]-4-(4-methyl-piperazin-1-yl)-benzoylamino]-6,6-dimethyl-5,6-dihydro-4H-pyrrolo[3,4-c]pyrazole-1-carboxylic acid ethyl ester Formula (VII), R=2-[((S)-2-Methoxy-1-methyl-ethyl)-(2,2,2-trifluoro-acetyl)-amino]-4-(4-methyl-piperazin)-phenyl, Ar=2,6-dichlorophenyl, A=NH ESI MS: m/z 797 (MH+).

Example 4

5-[2-(2,6-Difluoro-phenyl)-acetyl]-6,6-dimethyl-3-[4-(4-methyl-piperazin-1-yl)-benzoylamino]-5,6-dihydro-4H-pyrrolo[3,4-c]pyrazole-2-carboxylic acid ethyl ester Formula (VII), R=4-(4-methyl-piperazin)-phenyl, Ar=2,6-difluorophenyl, A=$CH_2$ To a solution of 6,6-Dimethyl-3-[4-(4-methyl-piperazin-1-yl)-benzoylamino]-5,6-dihydro-4H-pyrrolo[3,4-c]pyrazole-2-carboxylic acid ethyl ester dihydrochloride (0.50 g, 1.00 mmol) N,N-diispropylethylamine (0.68 mL, 4.00 mmol) (2,6-Difluoro-phenyl)-acetic acid (0.26 g, 1.50 mmol) in dry $CH_2Cl_2$ (30 ml), O-(1H-benzotriazol-1-yl)-N,N,N',N'-tetramethyluronium tetrafluoroborate (0.48 g, 1.50 mmol) was added. The reaction was stirred at room temperature over night, the solvent removed under reduced pressure, the residue dissolved in $CH_2Cl_2$ (40 mL) and washed with water (1×20 mL) then with saturated sodium hydrogencarbonate aqueous solution (1×20 mL). The organic phase was dried over sodium sulphate, the solvent evaporated in vacuo and the crude product purified by flash chromatography ($CH_2Cl_2$/MeOH 95/5) to afford 0.40 g (yield 69%) of the title compound.

ESI MS: m/z 581 (MH+);
$^1$H NMR (400 MHz, DMSO-$d_6$): δ 10.72 (s, 1H), 7.67 (s, 2H), 7.37 (m, 1H), 7.15-7.05 (m, 4H), 4.98 (s, 2H), 4.48 (q, 2H, J=7.1 Hz), 3.79 (s, 2H), 3.32 (m, 4H), 2.50 (m, 4H), 2.26 (s, 3H), 1.66 (s, 6H), 1.38 (t, 3H, J=7.1 Hz).

Example 5

6,6-Dimethyl-3-[4-(4-methyl-piperazin-1-yl)-benzoylamino]-2,6-dihydro-4H-pyrrolo[3,4-c]pyrazole-5-carboxylic acid (2,6-difluoro-phenyl)-amide
(Comp. 3, A1-Z-B3)

To a solution of triphosgene (195 mg, 0.65 mmol, 0.56 eq) in DCM (15 mL) was added a solution of 6,6- Dimethyl-3-[4-

(4-methyl-piperazin-1-yl)-benzoylamino]-5,6-dihydro-4H-pyrrolo[3,4-c]pyrazole-2-carboxylic acid ethyl ester dihydrochloride (0.60 g, 1.15 mmol) in DCM (30 mL) followed by N,N-diisopropylethylamine (760 microL, 4.31 mmol, 3.75 eq). After 3 hours, a solution of 2,6-Difluoro-phenylamine (0.22, 1.72 mmol, 1.5 eq) and diisopropylethylamine (300 microL, 1.72 mmol, 1.5 eq) in DCM (8 mL) was added. The reaction was stirred overnight at room temperature. The solution was washed with brine, the organic phase was dried over sodium sulphate and concentrated. The residue was dissolved in methanol (16 mL), treated with TEA (1.6 mL, 11.5 mmol, 10 eq) and stirred overnight at room temperature. After evaporation of the solvent, the solid was purified by flash chromatography ($CH_2Cl_2$/MeOH/$NH_3$ 95/5/01). The solid was treated with diisopropylether and filtered to afford 0.37 g of the title compound in 64% yield.

ESI MS: m/z 510 ($MH^+$);

$^1$H NMR (400 MHz, DMSO-$d_6$): δ 12.41 (s, 1H), 10.57 (s, 1H), 8.35 (s, 1H), 7.93 (m, 2H), 7.20-7.05 (m, 3H), 7.00 (m, 2H), 4.70 (s, 2H), 3.33 (m, 4H), 2.46 (m, 4H), 2.24 (s, 3H), 1.68 (s, 6H).

Example 6

6,6-Dimethyl-3-[4-(4-methyl-piperazin-1-yl)-benzoylamino]-2,6-dihydro-4H-pyrrolo[3,4-c]pyrazole-5-carboxylic acid (2,6-dichloro-phenyl)-amide (Comp. 1, A1-Z-B1)

5-(2,6-Dichloro-phenylcarbamoyl)-6,6-dimethyl-3-[4-(4-methyl-piperazin-1-yl)-benzoylamino]-5,6-dihydro-4H-pyrrolo[3,4-c]pyrazole-2-carboxylic acid ethyl ester (0.6 g, 0.97 mmol) was dissolved in methanol (20 mL), treated with TEA (0.67 mL, 4.85 mmol, 5 eq) and stirred overnight at room temperature. After evaporation of the solvent, the solid was treated with diethyl ether and filtered to afford 0.28 g (yield 76%) of the title compound.

ESI MS: m/z 542 ($MH^+$);

$^1$H NMR (400 MHz, DMSO-$d_6$): δ 12.42 (s, 1H), 10.57 (s, 1H), 8.15 (s, 1H), 7.93 (m, 2H), 7.50 (m, 2H), 7.29 (m, 1H), 7.01 (m, 2H), 4.72 (s, 2H), 3.35 (m, 4H), 2.52 (m, 4H), 2.32 (s, 3H), 1.68 (s, 6H).

By working in an analogous manner the following compounds were prepared:

| N° | Code | ESI MS: m/z ($MH^+$) | NMR data |
|---|---|---|---|
| 2 | A1-Z-B2 | 473 | (400 MHz, DMSO-$d_6$): δ 12.39 (s, 1H), 10.58 (s, 1H), 7.89 (m, 2H), 7.31 (m, 2H), 7.28-7.22 (m, 3H), 6.99 (m, 2H), 4.74 (s, 2H), 3.70 (s, 2H), 3.33 (m, 4H), 2.51 (m, 4H), 2.26 (s, 3H), 1.70 (s, 6H). |
| 4 | A1-Z-B4 | 509 | (400 MHz, DMSO-$d_6$): δ 12.39 (s, 1H), 10.57 (s, 1H), 7.90 (m, 2H), 7.12-6.93 (m, 5H), 4.77 (s, 2H), 3.78 (s, 2H), 3.29 (m, 4H), 2.44 (m, 4H), 2.22 (s, 3H), 1.68 (s, 6H). |
| 5 | A1-Z-B5 | 509 | (400 MHz, DMSO-$d_6$): δ 12.40 (s, 1H), 10.59 (s, 1H), 7.91 (m, 2H), 7.36 (m, 1H), 7.07 (m, 2H), 6.98 (m, 2H), 4.82 (s, 2H), 3.75 (s, 2H), ), 3.32 (m, 4H), 2.45 (m, 4H), 2.23 (s, 3H), 1.65 (s, 6H). |
| 6 | A2-Z-B1 | 542 | (400 MHz, DMSO-$d_6$): δ 12.48 (s, 1H), 10.86 (s, 1H), 8.16 (s, 1H) 7.59 (s, 1H), 7.49 (m, 2H), 7.43 (m, 1H) 7.34 (m, 1H) 7.29 (m, 1H), 7.15 (m, 1H), 4.74 (s, 2H), 3.23 (m, 4H), 2.51 (m, 4H), 2.24 (s, 3H), 1.69 (s, 6H). |
| 7 | A3-Z-B1 | 536 | (400 MHz, DMSO-$d_6$): δ 12.44 (s, 1H), 10.58 (s, 1H), 8.15 (s, 1H) 7.74 (m, 1H), 7.49 (m, 3H), 7.43 (m, 2H), 7.28 (m, 2H) 7.20 (m, 1H), 7.13 (m, 2H), 6.91 (m, 1H), 4.72 (s, 2H), 1.67 (s, 6H). |
| 8 | A1-Z-B6 | 474 | (400 MHz, DMSO-$d_6$): δ 12.40 (s, 1H), 10.56 (s, 1H), 8.10 (s, 1H), 7.93 (bs, 2H), 7.54 (m, 2H), 7.24 (m, 2H), 7.00 (m, 2H) 6.94 (m, 1H), 4.72 (s, 2H), 3.33 (m, 4H), 2.46 (m, 4H), 2.24 (s, 3H), 1.72 (s, 6H). |
| 9 | A1-Z-B7 | 541 | (400 MHz, DMSO-$d_6$): δ 12.43 (s, 1H), 10.62 (s, 1H), 7.93 (bs, 2H), 7.49 (m, 2H), 7.33 (m, 1H), 7.00 (bs, 2H) 4.90 (s, 2H), 4.00 (s, 2H), 3.32 (m, 4H), 2.51 (m, 4H), 2.25 (s, 3H), 1.68 (s, 6H). |
| 58 | A4-Z-B1 | 512 | (400 MHz, DMSO-$d_6$): δ 12.47 (s, 1H), 11.05 (s, 1H), 8.19 (s, 1H), 7.98-7.60 (m, 4H), 7.49 (m, 2H), 7.29 (m, 1H), 4.73 (s, 2H), 1.70 (s, 6H). |
| 59 | A2-Z-B5 | 509 | (400 MHz, DMSO-$d_6$): δ 12.49 (bs, 1H), 10.91 (s, 1H), 7.57 (s, 1H), 7.42 (s, 1H), 7.38 (m, 1H), 7.17 (m, 1H) 7.09 (m, 2H) 4.88 (s, 2H), 3.77 (s, 2H), 3.25 (m, 4H), 2.51 (m, 4H), 2.25 (s, 3H), 1.68 (s, 6H). |
| 60 | A1-Z-B56 | 479 | (400 MHz, DMSO-$d_6$): δ 12.40 (bs, 1H), 10.59 (s, 1H), 7.90 (m, 2H), 7.38 (m, 1H), 7.05-6.90 (m, 4H), 4.76 (s, 2H), 3.92 (s, 2H), 3.07 (m, 4H), 2.50 (m, 4H), 2.30 (s, 3H), 1.68 (s, 6H). |
| 61 | A5-Z-B5 | 469 | (400 MHz, DMSO-$d_6$): δ 12.55 (s, 1H), 11.17 (s, 1H), 8.20-8.00 (m, 4H) 7.36 (s, 1H), 7.07 (m, 2H), 4.88 (s, 2H), 3.90 (s, 3H), 3.75 (s, 2H), 1.67 (s, 6H). |
| 104 | A47-Z-B5 | 429 | (400 MHz, DMSO-$d_6$): δ 12.89 (s, 1H), 10.46 (s, 1H), 7.86 (m, 1H) 7.57 (s, 1H), 7.34 (m, 3H), 7.07 (m, 2H), 4.89 (s, 2H), 3.75 (s, 2H), 1.67 (s, 6H). |
| 106 | A4-Z-B5 | 479 | $^1$H NMR (400 MHz, DMSO-$d_6$): δ 12.48 (s, 1H), 11.08 (s, 1H), 7.85-7.60 (m, 4H), 7.36 (m, 1H), 7.08 (m, 2H), 4.84 (s, 2H), 3.74 (s, 2H), 1.67 (s, 6H). |

| N° | Code | ESI MS: m/z (MH+) | NMR data |
|---|---|---|---|
| 185 | A89-Z-B1 | 502 | (400 MHz, DMSO-d$_6$) δ ppm 1.68 (s, 6 H) 3.90 (s, 3 H) 4.74 (s, 2 H) 7.28 (dd, J = 8.41, 7.80 Hz, 1 H) 7.47-7.51 (m, 2 H) 7.68 (t, J = 7.56 Hz, 1 H) 8.07-8.20 (m, 1 H) 8.29 (d, J = 7.80 Hz, 1 H) 8.60-8.63 (m, 1 H) 11.19 (br. s., 1 H) 12.53 (br. s., 1 H) |
| 186 | A90-Z-B1 | 502 | (40 MHz, DMSO-d$_6$) δ ppm 1.69 (s, 6 H) 3.90 (s, 3 H) 4.74 (br. s., 2 H) 7.29 (dd, J = 8.41, 7.80 Hz, 1 H) 7.50 (d, J = 8.05 Hz, 2 H) 7.99-8.27 (m, 5 H) 11.13 (s, 1 H) 12.54 (br. s., 1 H) |
| 236 | A17-Z-B6 | 376 | (400 MHz, DMSO-d$_6$): δ 12.49 (bs, 1H), 10.90 (s, 1H), 8.11 (s, 1H), 8.03 (m, 2H), 7.61 (m, 1H), 7.55 (m, 2H), 7.52 (m, 2H), 7.24 (m, 2H), 6.94 (m, 1H), 4.75 (s, 2H), 1.73 (s, 6H). |
| 237 | A17-Z-B2 | 375 | (400 MHz, DMSO-d$_6$): δ 12.48 (bs, 1H), 10.02 (s, 1H), 7.99 (m, 2H), 7.60 (m, 1H), 7.51 (m, 2H), 7.31 (m, 2H), 7.26 (m, 3H), 4.76 (s, 2H), 3.71 (s, 2H), 1.71 (s, 6H). |
| 239 | A73-Z-B1 | 480 | (400 MHz, DMSO-d$_6$): δ 12.54 (s, 1H), 11.28 (s, 1H), 8.20 (s, 1H), 7.57 (m, 1H), 7.49 (m, 2H), 7.29 (m, 1H), 7.22 (m, 2H), 4.75 (m, 2H), 1.70 (s, 6H). |
| 241 | A75-Z-B1 | 487 | (400 MHz, DMSO-d$_6$) δ ppm 1.68 (s, 6 H) 4.74 (br. s., 2 H) 7.28 (dd, J = 8.35, 7.87 Hz, 1 H) 7.46-7.52 (m, 3 H) 7.92-8.19 (m, 6 H) 11.02 (br. s., 1 H) 12.51 (br. s., 1 H) |
| 244 | A78-Z-B1 | 522 | (400 MHz, DMSO-d$_6$): δ 12.53 (s, 1H), 11.22 (s, 1H), 8.23 (m, 2H) 8.16 (s, 1H), 8.05 (m, 2H), 7.49 (m, 2H) 7.28 (m, 1H), 4.75 (s, 2H), 3.30 (s, 3H), 1.69 (s, 6H). |
| 249 | A83-Z-B1 | 584 | (400 MHz, DMSO-d$_6$): δ 12.50 (s, 1H), 10.87 (s, 1H), 10.16 (s, 1H), 8.31 (m, 1H), 8.15 (bs. s., 1H), 7-66-7-77 (m, 2H), 7.51 (m, 2H), 7.39-7.47 (m, 1H) 7.26-7.34 (m, 1H), 4.74 (s, 2H), 3.25-3.43 (m, 2H), 3.18 (m, 1H), 2.42-2.62 (m, 2H), 2.52 (s, 3H), 1.88-1.98 (m, 2H), 1.75-1.97 (m, 2H), 1.69 (s, 6H). |
| 250 | A84-Z-B1 | 459 | (400 MHz, DMSO-d$_6$) δ ppm 1.66 (s, 6 H) 4.68 (s, 2 H) 5.26 (br. s., 2 H) 6.69-6.77 (m, 1 H) 7.07-7.15 (m, 3 H) 7.22-7.30 (m, 1 H) 7.44-7.51 (m, 2 H) 8.10 (br. s., 1 H) 10.59 (br. s., 1 H) 12.41 (br. s., 1 H) |
| 251 | A85-Z-B1 | 459 | 1H NMR (400 MHz, DMSO-d$_6$) δ ppm 1.66 (br. s., 6 H) 4.68 (br. s., 2 H) 5.72 (bs. s., 2H), 6.51-6.64 (m, 2H), 7.27 (t, J = 8.05 Hz, 1 H) 7.48 (d, J = 7.80 Hz, 2 H) 7.65-7.81 (m, 2H), 8.12 (s, 1H), 10.32 (s, 1H), 12.33 (s, 1H), |
| 253 | A87-Z-B1 | 507 | (400 MHz, DMSO-d$_6$) δ ppm 1.68 (s, 6 H) 4.74 (s, 2 H) 7.24-7.31 (m, 1 H) 7.46-7.52 (m, 2 H) 7.71-7.79 (m, 1 H) 8.15 (br. s., 1 H) 8.44 (d, J = 7.19 Hz, 1 H) 8.82 (d, J = 7.56 Hz, 1 H) 11.34 (s, 1 H) 12.58 (s, 1 H) |
| 255 | A91-Z-B1 | 580 | — |
| 259 | A1-Z-B113 | 546 | (400 MHz, DMSO-d6): δ 1.68 (s, 6 H) 2.30 (s, 3 H) 2.87 (s, 3 H) 3.00-3.22 (m, 4 H) 3.53 (d, J = 9.02 Hz, 2 H) 4.06 (d, J = 10.24 Hz, 2 H) 4.65 (s, 2 H) 6.51 (s, 1 H) 7.09 (d, J = 8.90 Hz, 2 H) 7.89 (s, 1 H) 7.97 (d, J = 8.90 Hz, 2 H) 9.70 (br. s., 1 H) 10.67 (s, 1 H) 12.43 (br. s., 1 H) |
| 260 | A1-Z-B114 | 480 | (400 MHz, DMSO-d6): δ 1.70 (s, 6 H) 2.87 (s, 3 H) 3.01-3.20 (m, 4 H) 3.53 (d, J = 9.15 Hz, 2 H) 4.06 (d, J = 12.56 Hz, 2 H) 4.65 (s, 2 H) 7.06-7.11 (m, 2 H) 7.21-7.24 (m, 1 H) 7.31-7.36 (m, 2 H) 7.97 (d, J = 9.02 Hz, 2 H) 8.53 (s, 1 H) 9.69 (br. s., 1 H) 10.64 (s, 1 H) |
| 261 | A1-Z-B115 | 493 | (400 MHz, DMSO-d6): δ 1.67 (s, 6 H) 2.09 (s, 3 H) 2.26 (s, 3 H) 2.88 (s, 3 H) 3.01-3.22 (m, 4 H) 3.54 (d, J = 11.10 Hz, 2 H) 4.06 (d, J = 11.95 Hz, 2 H) 4.65 (s, 2 H) 7.09 (d, J = 9.02 Hz, 2 H) 7.59 (s, 1 H) 7.97 (d, J = 8.90 Hz, 2 H) 9.69 (br. s., 1 H) 10.65 (s, 1 H) |
| 262 | A1-Z-B116 | 499 | (400 MHz, DMSO-d6): δ 1.70 (s, 6 H) 2.87 (s, 3 H) 3.01-3.21 (m, 4 H) 3.49-3.56 (m, 2 H) 4.06 (d, J = 11.95 Hz, 2 H) 4.75 (s, 2 H) 7.08 (d, J = 9.02 Hz, 2 H) 7.22-7.27 (m, 1 H) 7.52 (d, J = 7.56 Hz, 1 H) 7.59-7.65 (m, 1 H) 7.73 (dd, J = 7.80, 1.34 Hz, 1 H) 7.97 (d, J = 9.02 Hz, 2 H) 8.51 (s, 1 H) 9.68 (br. s., 1 H) 10.68 (s, 1 H) |
| 263 | A1-Z-B117 | 480 | (400 MHz, DMSO-d6): δ 1.70 (s, 6 H) 2.87 (s, 3 H) 3.00-3.22 (m, 4 H) 3.53 (d, J = 10.61 Hz, 2 H) 4.06 (d, J = 13.17 Hz, 2 H) 4.66 (s, 2 H) 6.71 (dd, J = 3.05, 2.07 Hz, 1 H) 6.75-6.79 (m, 2 H) 7.05-7.12 (m, 2 H) 7.98 (d, J = 9.02 Hz, 2 H) 9.37 (s, 1 H) 9.69 (br. s., 1 H) 10.66 (s, 1 H). |
| 264 | A1-Z-B118 | 543 | (400 MHz, DMSO-d6): δ 1.71 (s, 6 H) 2.87 (s, 3 H) 2.99-3.27 (m, 4 H) 3.50-3.55 (m, 2 H) 4.06 (d, J = 13.17 Hz, 2 H) 4.75 (s, 2 H) 7.05-7.10 (m, 2 H) 7.77 (s, 2 H) 7.97 (d, J = 9.02 Hz, 2 H) 9.03 (s, 1 H) 9.69 (br. s., 1 H) 10.69 (s, 1 H). |
| 265 | A1-Z-B119 | 568 | (400 MHz, DMSO-d6): δ 1.69 (s, 6H), 2.26 (s, 3H), 2.88 (b.s., 3H), 3.00-3.25 (m, 4H), 3.48-3.59 (m, 2H), 4.06 (d, J = 13.29 Hz, 2H), 4.71 (s, 2H), 7.05-7.13 (m, 3H), 7.25 (d, J = 6.83 Hz, 1H), 7.48 (d, J = 7.93 Hz, 1H), 7.80 (s, 1H), 7.98 (d, J = 9.02 Hz, 2H), 9.70 (b.s., 1H), 10.65 (s, 1H). |

-continued

| N° | Code | ESI MS: m/z (MH+) | NMR data |
|---|---|---|---|
| 266 | A1-Z-B120 | 509 | (400 MHz, DMSO-d6): δ 1.72 (s, 6H), 2.88 (b.s., 3H), 3.04-3.21 (m, 4H), 3.49-3.60 (m, 2H), 4.07 (d, J = 7.32 Hz, 2H), 4.77 (s, 2H), 7.05-7.13 (m, 2H), 7.41 (dd, J = 7.99 and 4.69 Hz, 1H), 7.78 (s, 1H), 7.98 (d, J = 9.02 Hz, 2H), 8.13 (dd, J = 4.69 and 1.83 Hz, 1H), 8.18 (dd, J = 7.99 and 1.83 Hz, 1H), 9.68 (b.s., 1H), 10.71 (s, 1H). |
| 267 | A1-Z-B121 | 526 | (400 MHz, DMSO-d6): δ 1.68 (s, 6H), 2.88 (b.s., 3H), 2.97-3.21 (m, 4H), 3.48-3.68 (m, 2H), 3.99-4.16 (m, 2H), 4.71 (s, 2H), 7.09 (d, J = 9.02 Hz, 2H), 7.20-7.41 (m, 3H), 7.97 (d, J = 8.01 Hz, 2H), 9.72 (b.s., 1H), 10.66 (s, 1H). |
| 268 | A1-Z-B122 | 571 | (400 MHz, DMSO-d6): δ 1.68 (s, 6H), 2.88 (b.s., 3H), 2.98-3.24 (m, 4H), 3.47-3.61 (m, 2H), 3.99-4.13 (m, 2H), 4.71 (s, 2H), 7.05-7.14 (m, 2H), 7.20-7.32 (m, 2H), 7.48-7.53 (m, 1H), 7.93-8.03 (m, 3H), 9.70 (b.s., 1H), 10.66 (s, 1H). |
| 275 | A94-Z-B1 | 587 | (400 MHz, DMSO-d6) δ ppm 1.67 (s, 6 H) 2.23 (s, 3 H) 2.41-2.46 (m, 4 H) 3.30-3.38 (m, 4 H) 4.65 (br. s., 2 H) 7.21 (d, J = 7.93 Hz, 1 H) 7.24-7.30 (m, 1 H) 7.39 (br. s., 1 H) 7.44-7.51 (m, 2 H) 7.60 (d, J = 8.41 Hz, 1 H) 8.15 (br. s., 1 H) 11.01 (br. s., 1 H) 12.44 (s, 1 H) |
| 240 | A95-Z-B1 | 615 | (400 MHz, DMSO-d6) δ ppm 1.68 (br. s., 6 H) 2.22 (s, 3 H) 2.40-2.45 (m, 4 H) 3.25-3.28 (m, 4H) 3.29 (s, 3 H) 3.32 (br. s., 6 H) 3.53 (t, J = 5.30 Hz, 2 H) 4.63 (br. s., 2 H) 6.08 (s, 1 H) 6.20 (br. s., 1 H) 7.25-7.32 (m, 1 H) 7.48-7.52 (m, 2 H) 10.20 (br. s., 1 H) |

Example 7

3-Amino-5-(2,6-dichloro-phenylcarbamoyl)-6,6-dimethyl-5,6-dihydro-4H-pyrrolo[3,4-c]pyrazole-2-carboxylic acid ethyl ester Formula (XI), Ar=2,6-dichlorophenyl, A=NH To a solution of 3-amino-6,6-dimethyl-5,6-dihydro-4H-pyrrolo[3,4-c]pyrazole-2-carboxylic acid ethyl ester dihydrochloride (4.0 g, 15.30 mmol) N,N-diispropylethylamine (10.6 ml, 61.00 mmol) in dry THF (50 mL) cooled at 0° C., a solution of 1,3-dichlorophenyl isocyanate (3.16 g, 16.80 mmol) in dry THF (10 mL) was slowly added. The reaction was stirred at room temperature for 4 h, then the solvent removed under reduced pressure, the residue dissolved in DCM (100 mL) and washed with 0.1N hydrochloric acid solution water (1×20 mL) and with brine (1×20 mL). The organic phase was dried over sodium sulphate, the solvent evaporated in vacuo, the residue suspended in ethyl ether (50 mL) and stirred for 30'. The organic phase was removed under filtration yielding 4.5 g (yield 71%) of the title compound as white solid.

ESI MS: m/z 412 (MH+);
$^1$H NMR (400 MHz, DMSO-d$_6$): δ 7.99 (s, 1H), 7.52 (m, 2H), 7.31 (m, 1H), 6.61 (bs, 2H), 4.39 (s, 2H), 4.37 (q, 2H, J=7.0 Hz), 1.62 (s, 6H), 1.35 (t, 3H, J=7.0 Hz).

Example 8

3-Amino-5-[2-(2,6-difluoro-phenyl)-acetyl]-6,6-dimethyl-5,6-dihydro-4H-pyrrolo[3,4-c]pyrazole-2-carboxylic acid ethyl ester Formula (XI), Ar=2,6-difluorophenyl, A=CH$_2$ To a solution of 3-amino-6,6-dimethyl-5,6-dihydro-4H-pyrrolo[3,4-c]pyrazole-2-carboxylic acid ethyl ester dihydrochloride (4.5 g, 17.20 mmol) N,N-diispropylethylamine (12.00 mL, 68.80 mmol) (2,6-Difluoro-phenyl)-acetic acid (4.45 g, 28.50 mmol) in dry CH$_2$Cl$_2$ (30 ml) cooled in an ice bath, O-(1H-benzotriazol-1-yl)-N,N,N',N'-tetramethyluronium tetrafluoroborate (9.15 g, 28.50 mmol) was added. At the end of the addition the reaction was allowed to reach room temperature and stirred over night. The solvent was removed under reduced pressure, the residue dissolved in CH$_2$Cl$_2$ (40 mL) and washed with water (1×50 mL), 0.1N hydrochloric acid solution water (1×50 mL), sodium hydrogencarbonate aqueous solution (1×50 mL) and finally with brine (1×50 mL). The organic phase was dried over sodium sulphate, the solvent evaporated in vacuo and the residue suspended in ethyl ether (50 mL) and stirred for 30'. The organic phase was removed under filtration yielding 4.5 g (yield 69%) of the title compound as white solid.

ESI MS: m/z 379 (MH+);
$^1$H NMR (400 MHz, DMSO-d$_6$): δ 7.36 (m, 1H), 7.07 (m, 2H), 6.63 (s, 2H), 4.53 (s, 2H), 4.36 (q, 2H, J=7.2 Hz), 3.72 (s, 2H), 1.59 (s, 6H), 1.33 (t, 3H, J=7.2 Hz).

Example 9

5-(2,6-Dichloro-phenylcarbamoyl)-6,6-dimethyl-3-(2-trifluoromethyl-benzoylamino)-5,6-dihydro-4H-pyrrolo[3,4-c]pyrazole-2-carboxylic acid ethyl ester Formula (VII), R=2-trifluorophenyl, Ar=2,6-dichlorophenyl, A=NH To a solution of 3-Amino-5-(2,6-dichloro-phenylcarbamoyl)-6,6-dimethyl-5,6-dihydro-4H-pyrrolo[3,4-c]pyrazole-2-carboxylic acid ethyl ester (0.20 g, 0.53 mmol), N,N-diispropylethylamine (0.40 mL, 2.30 mmol) in anhydrous THF (20 mL), 2-trifluoromethyl-benzoyl chloride (0.88 mL, 0.60 mmol) was added. The reaction was heated to reflux and stirred for 6 h. The solvent was removed under vacuum and the crude residue purified by flash chromatography affording 0.22 g (yield 71%) of the title compound.

ESI MS: m/z 584 (MH+);
$^1$H NMR (400 MHz, DMSO-d$_6$): δ 11.03 (s, 1H), 8.20 (s, 1H), 7.95-7.60 (m, 4H), 7.47 (m, 2H), 7.31 (m, 1H), 4.73 (s, 2H), 4.47 (q, 2H, J=7.1 Hz), 1.70 (s, 6H), 1.35 (t, 3H, J=7.1 Hz).

By working in an analogous manner the following compounds were prepared:

5-[2-(2,6-Difluoro-phenyl)-acetyl]-6,6-dimethyl-3-(2-trifluoromethyl-benzoylamino)-5,6-dihydro-4H-pyrrolo[3,4-c]pyrazole-2-carboxylic acid ethyl ester Formula (VII), R=2-trifluorophenyl,
Ar=2,6-difluorophenyl, A=CH$_2$ ESI MS: m/z 551 (MH$^+$);
$^1$H NMR (400 MHz, DMSO-d$_6$): δ 11.05 (s, 1H), 7.80-7.60 (m, 4H), 7.36 (m, 1H), 7.10 (m, 2H), 4.46 (q, 2H, J=7.1 Hz), 4.84 (s, 2H), 3.74 (s, 2H), 1.65 (s, 6H), 1.36 (t, 3H, J=7.1 Hz).

5-(2,6-Dichloro-phenylcarbamoyl)-3-(4-methoxycarbonyl-benzoylamino)-6,6-dimethyl-5,6-dihydro-4H-pyrrolo[3,4-c]pyrazole-2-carboxylic acid ethyl ester Formula (VII), R=4-methoxycarbonylphenyl,
Ar=2,6-dichlorophenyl, A=NH ESI MS: m/z 574 (MH$^+$);
$^1$H NMR (400 MHz, DMSO-d$_6$): δ 10.97 (s, 1H), 8.29 (s, 1H), 8.18 (m, 2H), 8.06 (m, 2H), 7.50 (m, 2H), 7.30 (m, 1H), 4.81 (s, 2H), 4.48 (q, 2H, J=7.1 Hz), 3.91 (s, 3H), 1.69 (s, 6H), 1.38 (t, 3H, J=7.1 Hz).

3-(4-Nitro-benzoylamino)-5-(2,6-dichloro-phenylcarbamoyl)-6,6-dimethyl-5,6-dihydro-4H-pyrrolo[3,4-c]pyrazole-2-carboxylic acid ethyl ester Formula (VII), R=4-nitrophenyl,
Ar=2,6-dichlorophenyl, A=NH ESI MS: m/z 561 (MH$^+$)731

3-(3-Nitro-4-fluoro-benzoylamino)-5-(2,6-dichloro-phenylcarbamoyl)-6,6-dimethyl-5,6-dihydro-4H-pyrrolo[3,4-c]pyrazole-2-carboxylic acid ethyl ester Formula (VII), R=3-nitro,4-fluorophenyl,
Ar=2,6-dichlorophenyl, A=NH ESI MS: m/z 579 (MH$^+$)

Example 10

N-[5-(2,6-Dichloro-phenylcarbamoyl)-6,6-dimethyl-2,4,5,6-tetrahydro-pyrrolo[3,4-c]pyrazol-3-yl]-terephthalamic acid (Comp. 127, A6-Z-B1)

To a solution of 5-(2,6-Dichloro-phenylcarbamoyl)-3-(4-methoxycarbonyl-benzoylamino)-6,6-dimethyl-5,6-dihydro-4H-pyrrolo[3,4-c]pyrazole-2-carboxylic acid ethyl ester (0.4 g, 0.74 mmol) in methanol (5 mL), 2N NaOH aqueous solution (1.00 mL, 2.00 mmol) was added and warmed to 70° C. After 4 hours stirring, water was added (20 mL) and the aqueous solution extracted with ethyl acetate (1×20 mL). The aqueous phase was acidified with 1N HCl solution and extracted with ethyl acetate (2×20 mL). The combined organic phases were dried over sodium sulphate, the solvent evaporated in vacuo yielding 0.33 g (yield 91%) of the title compound as white solid.

ESI MS: m/z 488 (MH$^+$);
$^1$H NMR (400 MHz, DMSO-d$_6$): δ 13.4-12.4 (bs, 2H), 11.09 (s, 1H), 8.13 (bs, 1H), 8.11-8.03 (m, 4H), 7.49 (m, 2H), 7.28 (m, 1H), 4.73 (s, 2H), 1.68 (s, 6H).

By working in an analogous manner the following compounds were prepared:

| N° | Code | ESI MS: m/z (MH$^+$) | NMR data |
|---|---|---|---|
| 62 | A6-Z-B5 | 455 | (400 MHz, DMSO-d$_6$): δ 13.50-12.00 (bs, 1H), 11.14 (s, 1H), 8.11 (m, 2H), 8.03 (m, 2H), 7.35 (m, 1H), 7.07 (m, 2H), 4.88 (s, 2H), 3.76 (s, 2H), 1.67 (s, 6H). |
| 245 | A79-Z-B1 | 488 | (400 MHz, DMSO-d$_6$) δ ppm 1.70 (s, 6 H) 4.74 (s, 2 H) 7.26-7.33 (m, 1 H) 7.48-7.53 (m, 2 H) 7.67 (t, J = 7.80 Hz, 1 H) 8.12-8.17 (m, 2 H) 8.26 (d, J = 7.80 Hz, 1 H) 8.60 (t, J = 1.52 Hz, 1 H) 11.14 (s, 1 H) 12.66 (br. s., 1 H) |
| 256 | A74-Z-B1 | 524 | |

Example 11

N-[5-(2,6-Dichloro-phenylcarbamoyl)-6,6-dimethyl-1,4,5,6-tetrahydro-pyrrolo[3,4-c]pyrazol-3-yl]-N'-(1-methyl-piperidin-4-yl)-terephthalamide (Comp. 238, A72-Z-B1)

To a solution of N-[5-(2,6-Dichloro-phenylcarbamoyl)-6,6-dimethyl-2,4,5,6-tetrahydro-pyrrolo[3,4-c]pyrazol-3-yl]-terephthalamic acid (0.11 g, 0.22 mmol) N,N-diisopropylethylamine (0.12 mL, 0.66 mmol) 1-Methyl-piperidin-4-ylamine (0.04 g, 0.34 mmol) in dry CH$_2$Cl$_2$ (20 mL), O-(1H-benzotriazol-1-yl)-N,N,N',N'-tetramethyluronium tetrafluoroborate (0.11 g, 0.34 mmol) was added. The reaction was stirred at room temperature over night, the solvent removed under reduced pressure, the residue dissolved in CH$_2$Cl$_2$ (40 mL) and washed with water (1×20 mL) then with saturated sodium hydrogencarbonate aqueous solution (1×20 mL). The organic phase was dried over sodium sulphate, the solvent evaporated in vacuo and the crude product purified by flash chromatography (CH$_2$Cl$_2$/MeOH/NH$_3$ 90/10/1) to afford 0.07 g (yield 55%) of the title compound.

ESI MS: m/z 584 (MH$^+$);
$^1$H NMR (400 MHz, DMSO-d$_6$): δ 12.53 (s, 1H), 11.04 (s, 1H), 8.38 (d, 1H, J=7.6 Hz), 8.14 (s, 1H), 8.10-7.90 (m, 4H), 7.49 (m, 2H), 7.28 (m, 1H), 4.73 (s, 2H), 3.75 (m, 1H), 3.78 (m, 2H), 2.17 (s, 3H), 1.97 (m, 2H), 1.77 (m, 2H), 1.68 (s, 6H), 1.58 (m, 2H).

By working in an analogous manner the following compounds were prepared:

| N° | Code | ESI MS: m/z (MH$^+$) | NMR data |
|---|---|---|---|
| 128 | A69-Z-B5 | 525 | (400 MHz, DMSO-d$_6$): δ 12.53 (s, 1H), 11.07 (s, 1H), 8.54 (m, 1H), 8.08 (m, 2H), 7.93 (m, 2H), 7.34 (m, 1H), 7.07 (m, 2H), 4.89 (s, 2H), 3.76 (s, 2H), 3.39 (m, 2H), 2.50 (m, 2H), 2.33 (s, 6H), 1.67 (s, 6H). |

-continued

| N° | Code | ESI MS: m/z (MH+) | NMR data |
|---|---|---|---|
| 233 | A71-Z-B5 | 539 | (400 MHz, DMSO-$d_6$): δ 12.55 (s, 1H), 11.08 (s, 1H), 8.65 (m, 1H), 8.09 (m, 2H), 7.95 (m, 2H), 7.38 (m, 1H), 7.09 (m, 2H), 4.91 (s, 2H), 3.77 (s, 2H), 3.33 (m, 2H), 2.28 (t, J = 6.7 Hz, 2H), 2.16 (s, 6H), 1.68 (m, 8H). |
| 234 | A72-Z-B5 | 551 | (400 MHz, DMSO-$d_6$): δ 12.54 (s, 1H), 11.07 (s, 1H), 8.39 (d, J = 7.5 Hz, 1H), 8.09 (m, 2H), 7.94 (m, 2H), 7.36 (m, 1H), 7.07 (m, 2H), 4.89 (s, 2H), 3.77 (m, 1H), 3.76 (s, 2H), 2.81 (m, 2H), 2.20 (s, 3H), 2.01 (m, 2H), 1.80 (m, 2H), 1.67 (s, 6H), 1.61 (m, 2H). |
| 235 | A71-Z-B1 | 572 | (400 MHz, DMSO-$d_6$): δ 12.52 (bs, 1H), 11.04 (s, 1H), 8.66 (t, J = 6.0 Hz, 1H), 8.13 (s, 1H), 8.08 (m, 2H), 7.94 (m, 2H), 7.50 (m, 2H), 7.28 (m, 1H), 4.73 (s, 2H), 3.32 (m, 2H), 2.50 (m, 2H), 2.32 (s, 6H), 1.73 (m, 2H), 1.68 (m, 6H). |
| 243 | A77-Z-B1 | 584 | (400 MHz, DMSO-$d_6$) δ ppm 1.68 (s, 6 H) 1.79-1.94 (m, 2 H) 1.99-2.10 (m, 2 H) 2.58-2.67 (m, 1 H) 2.79 (s, 3 H) 2.89-3.01 (m, 2 H) 3.44-3.54 (m, 2 H) 4.72 (br. s., 2 H) 7.23-7.33 (m, 1 H) 7.45-7.52 (m, 2 H) 7.72 (d, J = 8.54 Hz, 2 H) 8.00 (d, J = 8.05 Hz, 2 H) 8.14 (br. s., 1 H) 9.40 (br. s., 1 H) 10.34 (br. s., 1 H) 10.78 (br. s., 1 H) 12.47 (br. s., 1 H) |
| 246 | A80-Z-B1 | 487 | (400 MHz, DMSO-$d_6$) δ ppm 12.51 (br. s., 1 H), 10.93 (br. s., 1 H), 8.51 (s, 1 H), 7.93-8.21 (m, 3 H), 7.59 (m, 1 H), 7.49 (m, 2 H), 7.28 (m, 1 H), 4.74 (br. s., 2 H), 1.68 (s, 6 H). |
| 247 | A81-Z-B1 | 584 | (400 MHz, DMSO-$d_6$) δ ppm 12.52 (br. s., 1 H), 10.94 (br. s., 1 H), 8.44 (br. s., 1 H), 8.36 (br. s., 1H), 8.10-8.18 (m, 2 H), 7.62 (m, 1 H), 7.49 (m, 2 H), 7.26-7.30 (m, 1 H), 4.75 (br. s., 2 H), 3.74-3.85 (br. s. 1 H), 2.81-2.94 (br. s. 2 H), 2.25 (s, 3 H), 2.06-2.14 (br. s., 2 H), 1.77-1.86 (m, 2 H), 1.68 (s, 6 H), 1.58-1.65 (m, 2 H). |

Example 12

3-[3-Amino-4-(4-methyl-piperazin-1-yl)-benzoylamino]-6,6-dimethyl-2,6-dihydro-4H-pyrrolo[3,4-c]pyrazole-5-carboxylic acid (2,6-dichloro-phenyl)-amide (Comp. 252, A86-Z-B1)

To a solution of 3-(3-Nitro-4-fluoro-benzoylamino)-5-(2,6-dichloro-phenylcarbamoyl)-6,6-dimethyl-5,6-dihydro-4H-pyrrolo[3,4-c]pyrazole-2-carboxylic acid ethyl ester (0.28 g, 0.48 mmol) in dry THF (10 mL), N-methylpiperazine (0.16 L, 1.40 mmol) was added. The reaction was stirred at room temperature for four hours, the solvent removed under reduced pressure and the crude product purified by flash chromatography (CH$_2$Cl$_2$/MeOH 90/10) to afford 0.20 g (yield 70%) of the title compound.

ESI MS: m/z 587 (MH+);

1H NMR (401 MHz, DMSO-$d_6$) δ ppm 1.69 (s, 6H) 2.21-2.24 (m, 3H) 2.42-2.46 (m, 4H) 3.10-3.17 (m, 4H) 4.73 (s, 2H) 7.25-7.32 (m, 1H) 7.35 (d, J=8.66 Hz, 1H) 7.46-7.52 (m, 2H) 8.15 (s, 1H) 8.20 (d, J=8.66 Hz, 1H) 8.52 (d, J=1.71 Hz, 1H) 11.02 (s, 1H) 12.51 (s, 1H)

Example 13

3-(4-Amino-benzoylamino)-5-(2,6-dichloro-phenylcarbamoyl)-6,6-dimethyl-5,6-dihydro-4H-pyrrolo[3,4-e]pyrazole-2-carboxylic acid ethyl ester Formula (VII), R=4-aminophenyl, Ar=2,6-dichlorophenyl, A=NH To a solution of 3-(4-Nitro-benzoylamino)-5-(2,6-dichloro-phenylcarbamoyl)-6,6-dimethyl-5,6-dihydro-4H-pyrrolo[3,4-c]pyrazole-2-carboxylic acid ethyl ester (0.30 g, 0.53 mmol) and 10% Pd/C in EtOH (10 mL) kept to reflux, cicloexene (1 mL) was added. The reaction was refluxed for two hours, the catalyst removed by filtration through a pad of celite, the solvent concentrated under reduced pressure and the crude product purified by flash chromatography (eluant: CH$_2$Cl$_2$/Acetone 90/10) to afford 0.16 g (yield 56%) of the title compound as a yellow solid ESI MS: m/z 531 (MH+);

1H NMR (400 MHz, DMSO-$d_6$) δ ppm 1.33-1.41 (m, 3H) 1.66 (s, 6H) 4.47 (q, J=7.07 Hz, 2H) 4.80 (s, 2H) 6.03 (s, 2H) 6.63-6.67 (m, 2H) 7.28 (dd, J=8.35, 7.87 Hz, 1H) 7.47-7.51 (m, 2H) 7.61 (d, J=8.78 Hz, 2H) 8.27 (s, 1H) 10.60 (s, 1H)

By working in an analogous manner the following compound was prepared:

| N° | Code | ESI MS: m/z (MH+) | NMR data |
|---|---|---|---|
| 254 | A88-Z-B1 | 557 | (400 MHz, DMSO-$d_6$) δ ppm 1.66 (s, 6H), 2.26 (s, 3H), 2.49-2.53 (m, 4H), 2.87 (m, 4H), 4.69 (s, 1 H) 4.84 (br. s., 1 H) 6.92-6.97 (m, 1 H) 7.23-7.31 (m, 3 H) 7.46-7.50 (m, 2 H) 8.11 (br. s., 1 H) 8.15 (s, 1 H) 10.53 (br. s., 1 H) 12.34 (br. s., 1 H) |

Example 14

N-[5-(2,6-Dichloro-phenylcarbamoyl)-6,6-dimethyl-2,4,5,6-tetrahydro-pyrrolo[3,4-c]pyrazol-3-yl]-N'-hydroxy-terephthalamide (Comp. 242, A76-Z-B1)

To a solution of N-[5-(2,6-Dichloro-phenylcarbamoyl)-6,6-dimethyl-2,4,5,6-tetrahydro-pyrrolo[3,4-c]pyrazol-3-yl]-terephthalamic acid (0.60 g, 1.22 mmol) O-(Tetrahydro-pyran-4-yl)-hydroxylamine (0.30 g, 2.56 mmol) in dry CH$_2$Cl$_2$ (20 mL), O-(1H-benzotriazol-1-yl)-N,N,N',N'-tetramethyluronium tetrafluoroborate (0.60 g, 1.84 mmol) was added. The reaction was stirred four hour at room temperature, diluted with DCM (30 mL) and washed with 05N HCl (1×20 mL), then with saturated sodium hydrogencarbonate aqueous solution (1×20 mL) and finally with brine (1×20 mL). The organic phase was dried over sodium sulphate, the solvent evaporated in vacuo and the crude product purified by flash chromatography ($CH_2Cl_2$/$MeOH_3$ 90/10) to afford the tetrahydropyranyl intermediate which was dissolved in MeOH (10 ml) and added of 2N HCl (1 mL). The reaction was stirred at room temperature over night, the solvent removed under reduced pressure and the residue suspended in DCM (20 mL). The suspension was stirred for 30', the solved allowed by filtration to yield 32 mg of the title compound as a pale yellow solid (yield 49%).

ESI MS: m/z 503 ($MH^+$);

$^1H$ NMR (400 MHz, DMSO-$d_6$): δ ppm 1.69 (s, 6H) 4.75 (br. s., 2H) 7.29 (dd, J=8.41, 7.80 Hz, 1H) 7.50 (d, J=8.05 Hz, 2H) 7.87 (d, J=8.05 Hz, 2H) 8.08 (d, J=8.29 Hz, 2H) 8.16 (br. s., 1H) 9.22 (s, 1H) 11.03 (br. s., 1H) 11.40 (br. s., 1H) 12.53 (br. s., 1H)

By working in an analogous manner the following compound was prepared:

| N° | Code | ESI MS: m/z ($MH^+$) | NMR data |
|---|---|---|---|
| 248 | A82-Z-B1 | 503 | (400 MHz, DMSO-$d_6$) δ ppm 11.27 (br. s., 1 H), 10.99 (s, 1 H), 8.39 (t, J = 1.46 Hz, 1 H), 8.09-8.15 (m, 2 H), 7.88-7.95 (m, 1 H), 7.60 (t, J = 7.80 Hz, 1 H), 7.46-7.51 (m, 2 H), 7.25-7.31 (m, 1 H), 4.73 (s, 2 H), 1.68 (s, 6 H). |

Example 15

6,6-Dimethyl-3-[4-(4-methyl-4-oxy-piperazin-1-yl)-benzoylamino]-4,6-dihydro-1H-pyrrolo[3,4-c]pyrazole-5-carboxylic acid (2,6-dichloro-phenyl)-amide (Comp. 257, A92-Z-B1)

To a solution of 6,6-Dimethyl-3-[4-(4-methyl-piperazin-1-yl)-benzoylamino]-2,6-dihydro-4H-pyrrolo[3,4-c]pyrazole-5-carboxylic acid (2,6-dichloro-phenyl)-amide (0.30 g, 0.54 mmol) in a 1:1 DCM/acetone mixture (20 mL), 0.1 M solution of dimethyldioxirane (10 mL) (prepared as described in *J. Org. Chem* 1987, 52, 1800) was added. The reaction was stirred at room temperature for 1 h, the solvent evaporated in vacuo and the crude product purified by flash chromatography ($CH_2Cl_2$/$MeOH_3$/$NH_3$ 85/15/0.2) yielding 0.23 g of the title compound as a white solid (yield=73%).

ESI MS: m/z 558 ($MH^+$);

$^1H$ NMR (400 MHz, DMSO-$d_6$) δ ppm 1.67 (s, 6H) 3.03 (d, J=9.88 Hz, 2H) 3.13 (s, 3H) 3.42-3.58 (m, 4H) 3.72 (d, J=12.19 Hz, 2H) 4.70 (br. s., 2H) 7.06 (br. s., 2H) 7.28 (dd, J=8.41, 7.80 Hz, 1H) 7.46-7.51 (m, 2H) 7.93 (br. s., 2H) 8.12 (br. s., 1H) 10.62 (s, 1H) 12.42 (br. s., 1H)

By working in an analogous manner with a 5 fold excess of dimethyldioxirare and increasing the reaction time to 12 hours, the following compound was prepared:

| N° | Code | ESI MS: m/z ($MH^+$) | NMR data |
|---|---|---|---|
| 258 | A93-Z-B1 | 574 | (400 MHz, DMSO-$d_6$) δ ppm 1.68 (s, 6 H) 3.24 (s, 3 H) 4.74 (s, 2 H) 7.28 (dd, J = 8.41, 7.80 Hz, 1 H) 7.42-7.53 (m, 2 H) 8.15 (d, J = 8.66 Hz, 3 H) 8.27 (d, J = 10.24 Hz, 2 H) 11.11 (br. s., 1 H) 12.54 (br. s., 1 H) |

Purification

Several compounds of the invention of formula (I), being prepared as formerly reported, were purified by preparative HPLC.

The operative conditions are reported below:

Example 16

6,6-Dimethyl-3-[4-(4-methyl-piperazin-1-yl)-benzoylamino]-2,6-dihydro-4Hpyrrolo[3,4-c]pyrazole-5-carboxylic acid (2-chloro-6-fluoro-phenyl)-amide (Comp 267, A1-Z-B121)

To a solution of di-tert-butyl dicarbonate (101 mg, 0.46 mmol, 1.1 eq) in DCM (2 mL) was added 2-chloro-6-fluoroaniline (61 mg, 0.42 mmol, 1 eq) and N,N-dimethylpyridin-4-amine (51 mg, 0.42 mmol, 1 eq). After 1 hour of agitation at room temperature, 6,6-Dimethyl-3-[4-(4-methyl-piperazin-1-yl)-benzoylamino]-5,6-dihydro-4Hpyrrolo[3,4-c]pyrazole-2-carboxylic acid ethyl ester dihydrochloride (189 mg, 0.38 mmol, 0.9 eq), triethylamine (0.23 mL, 1.68 mmol, 4 eq) and an additional 2 mL of DCM (4 mL total). The cocktail was placed in a Personal Chemistry, Smith Creator microwave reaction station and the vial contents were irradiated at 125° C. for 10 minutes with application of continuous, simultaneous cooling. After the 10 minutes of heating time had elapsed, the solution was washed twice with water. The organic phase was collected and the solvent was removed in vacuo. The residue was dissolved in methanol (3 mL), treated with triethylamine (0.3 mL, 2.2 mmol, 5 eq) and agitated for 6 hours at 50° C. After evaporation of the solvent, the solid was purified by preparative HPLC to afford 0.012 g of the title compound in 5% overall yield.

ESI MS: m/z 526 ($MH^+$)

$^1H$ NMR (400 MHz, DMSO-$d_6$): δ 1.68 (s, 6H), 2.88 (b.s., 3H), 2.97-3.21 (m, 4H), 3.48-3.68 (m, 2H), 3.99-4.16 (m, 2H), 4.71 (s, 2H), 7.09 (d, J=9.02 Hz, 2H), 7.20-7.41 (m, 3H), 7.97 (d, J=8.01 Hz, 2H), 9.72 (b.s., 1H), 10.66 (s, 1H).

By working in an analogous manner the following compounds were prepared:

| N° | Code | ESI MS: m/z ($MH^+$) | NMR data |
|---|---|---|---|
| 265 | A1-Z-B119 | 568 | (400 MHz, DMSO-$d_6$): δ 1.69 (s, 6H), 2.26 (s, 3H), 2.88 (b.s., 3H), 3.00-3.25 (m, 4H), 3.48-3.59 (m, 2H), 4.06 (d, J = 13.29 Hz, 2H), 4.71 (s, 2H), 7.05-7.13 (m, 3H), 7.25 (d, J = 6.83 Hz, 1H), 7.48 (d, J = 7.93 Hz, 1H), 7.80 (s, 1H), 7.98 (d, J = 9.02 Hz, 2H), 9.70 (b.s., 1H), 10.65 (s, 1H). |

-continued

| N° | Code | ESI MS: m/z (MH+) | NMR data |
|---|---|---|---|
| 266 | A1-Z-B120 | 509 | (400 MHz, DMSO-$d_6$): δ 1.72 (s, 6H), 2.88 (b.s., 3H), 3.04-3.21 (m, 4H), 3.49-3.60 (m, 2H), 4.07 (d, J = 7.32 Hz, 2H), 4.77 (s, 2H), 7.05-7.13 (m, 2H), 7.41 (dd, J = 7.99 and 4.69 Hz, 1H), 7.78 (s, 1H), 7.98 (d, J = 9.02 Hz, 2H), 8.13 (dd, J = 4.69 and 1.83 Hz, 1H), 8.18 (dd, J = 7.99 and 1.83 Hz, 1H), 9.68 (b.s., 1H), 10.71 (s, 1H). |
| 268 | A1-Z-B122 | 571 | (400 MHz, DMSO-$d_6$): δ 1.68 (s, 6H), 2.88 (b.s., 3H), 2.98-3.24 (m, 4H), 3.47-3.61 (m, 2H), 3.99-4.13 (m, 2H), 4.71 (s, 2H), 7.05-7.14 (m, 2H), 7.20-7.32 (m, 2H), 7.48-7.53 (m, 1H), 7.93-8.03 (m, 3H), 9.70 (b.s., 1H), 10.66 (s, 1H). |

| N° | Code | r.t. (min) | [M + H]+ | HPLC Method |
|---|---|---|---|---|
| 269 | A1-Z-B123 | 3.8 | 578 | 2 |
| 270 | A1-Z-B124 | 3.5 | 587 | 2 |
| 271 | A1-Z-B125 | 3.6 | 577 | 2 |
| 272 | A1-Z-B126 | 3.0 | 621 | 2 |
| 273 | A1-Z-B127 | 3.8 | 579 | 2 |
| 274 | A1-Z-B128 | 4.2 | 626 | 2 |

Example 17

Semi-preparative HPLC purification was performed on the Biotage Parallex Flex 4-channel parallel purification system equipped with four $RP_{18}$ X-Terra Waters columns (19×100 mm, 55 μm). Data for each purification cycle was monitored by two wavelengths (λ=220 nm and 254 nm) where fraction collection was triggered by UV absorbance at 254 nm.

HPLC was carried out at 25° C. at a flow rate of 20 mL/min using as mobile phase A water containing 0.1% formic acid and 2% acetonitrile and as mobile phase B acetonitrile.

Two solvents gradients (a) or (b) where used:
a) 0% B for 1 minute, then to 30% B over 6 min and finally to 100% B over 2 minutes
b) 0% B for 1 minute, then to 40% B over 6 min and finally to 100% B over 2 minutes.

The injection volume was 1.5 mL.

Example 18

Several compounds of the invention of formula (I), being prepared as formerly reported, were also characterised by means of HPLC/Mass techniques, hence through retention time (r.t.) and Mass [M+H]+.

The operative conditions are reported below:
HPLC/MS Method 1

The HPLC equipment consisted of a Waters Alliance HT 2795 HPLC system equipped with a 996 Waters PDA detector and Micromass mod. ZQ single quadrupole mass spectrometer, equipped with an electrospray (ESI) ion source. Instrument control, data acquisition and data processing were providen by Millennium 4.0 and MassLynx 3.5 software.

HPLC was carried out at 25° C. at a flow rate of 1 mL/min using a RP18 Waters X Terra (4.6×50 mm, 5 μm) column. Mobile phase A was ammonium acetate 5 mM buffer (pH 5.2 with acetic acid/acetonitrile 95:5), and Mobile phase B was $H_2O$/acetonitrile (5:95); the gradient was from 10 to 90% B in 4 min then hold 90% B 1 minute. The injection volume was 10 microL.

The mass spectometer was operated in positive and in negative ion mode, the capillary voltage was set up at 3.48 kV for (ES+) and 2.76 kV for (ES−); the source temperature was 120° C.; cone was 15 V; full scan, mass range from 100 to 800 amu was set up.

HPLC/MS Method 2

The HPLC equipment consisted of a Waters Alliance HT 2795 HPLC system equipped with a 996 Waters PDA detector and Micromass mod. ZQ single quadrupole mass spectrometer, equipped with an electrospray (ESI) ion source. Instrument control, data acquisition and data processing were providen by Millennium 4.0 and MassLynx 3.5 software.

HPLC was carried out at 25° C. at a flow rate of 1 mL/min using a RP18 Waters X Terra (4.6×50 mm, 5 μm) column. Mobile phase A was ammonium acetate 5 mM buffer (pH 5.2 with acetic acid/acetonitrile 95:5), and Mobile phase B was $H_2O$/acetonitrile (5:95); the gradient was from 10 to 90% B in 8 min then hold 100% B 2 minute. The injection volume was 10 microL.

The mass spectometer was operated in positive and in negative ion mode, the capillary voltage was set up at 3.48 kV for (ES+) and 2.76 kV for (ES−); the source temperature was 120° C.; cone was 15 V; full scan, mass range from 100 to 800 amu was set up.

TABLE IV

| N° | Code | r.t. (min) | [M + H]+ | HPLC Method |
|---|---|---|---|---|
| 10 | A1-Z-B8 | 2.5 | 552 | 1 |
| 11 | A1-Z-B9 | 2.1 | 518 | 1 |
| 12 | A1-Z-B10 | 1.9 | 533 | 1 |
| 13 | A1-Z-B11 | 2.4 | 507 | 1 |
| 14 | A1-Z-B12 | 2.1 | 503 | 1 |
| 15 | A1-Z-B13 | 2.2 | 518 | 1 |
| 16 | A1-Z-B14 | 2.5 | 523 | 1 |
| 17 | A1-Z-B15 | 2.1 | 503 | 1 |
| 18 | A1-Z-B16 | 2.3 | 487 | 1 |
| 19 | A1-Z-B17 | 2.7 | 549 | 1 |
| 20 | A1-Z-B18 | 2.4 | 563 | 1 |
| 21 | A1-Z-B19 | 2.4 | 507 | 1 |
| 22 | A1-Z-B20 | 2.1 | 503 | 1 |
| 23 | A1-Z-B21 | 2.4 | 552 | 1 |
| 24 | A1-Z-B22 | 2.1 | 517 | 1 |
| 25 | A1-Z-B23 | 2.2 | 518 | 1 |
| 26 | A1-Z-B24 | 2.1 | 533 | 1 |
| 27 | A1-Z-B25 | 2.2 | 491 | 1 |
| 28 | A1-Z-B26 | 2.1 | 516 | 1 |
| 29 | A1-Z-B27 | 2.2 | 487 | 1 |
| 30 | A1-Z-B28 | 2.2 | 491 | 1 |
| 31 | A1-Z-B29 | 2.3 | 487 | 1 |
| 32 | A1-Z-B30 | 2.8 | 545 | 1 |
| 33 | A1-Z-B31 | 1.7 | 551 | 1 |
| 34 | A1-Z-B32 | 2.7 | 557 | 1 |
| 35 | A1-Z-B33 | 2.3 | 527 | 1 |
| 36 | A1-Z-B34 | 2.6 | 515 | 1 |
| 37 | A1-Z-B35 | 2.9 | 609 | 1 |
| 38 | A1-Z-B36 | 2.6 | 542 | 1 |
| 39 | A1-Z-B37 | 2.2 | 491 | 1 |

TABLE IV-continued

| N° | Code | r.t. (min) | [M + H]⁺ | HPLC Method |
|---|---|---|---|---|
| 40 | A1-Z-B38 | 2.3 | 525 | 1 |
| 41 | A1-Z-B39 | 2.3 | 519 | 1 |
| 42 | A1-Z-B40 | 2.6 | 563 | 1 |
| 43 | A1-Z-B41 | 3.0 | 609 | 1 |
| 44 | A1-Z-B42 | 2.4 | 541 | 1 |
| 45 | A1-Z-B43 | 2.7 | 586 | 1 |
| 46 | A1-Z-B44 | 2.3 | 509 | 1 |
| 47 | A1-Z-B45 | 2.2 | 509 | 1 |
| 48 | A1-Z-B46 | 2.3 | 509 | 1 |
| 49 | A1-Z-B47 | 2.6 | 541 | 1 |
| 50 | A1-Z-B48 | 1.9 | 563 | 1 |
| 51 | A1-Z-B49 | 2.6 | 542 | 1 |
| 52 | A1-Z-B50 | 2.5 | 523 | 1 |
| 53 | A1-Z-B51 | 2.1 | 533 | 1 |
| 54 | A1-Z-B52 | 2.3 | 507 | 1 |
| 55 | A1-Z-B53 | 2.4 | 599 | 1 |
| 56 | A1-Z-B54 | 2.3 | 509 | 1 |
| 57 | A1-Z-B55 | 2.2 | 563 | 1 |
| 58 | A4-Z-B1 | 2.3 | 512 | 1 |
| 63 | A7-Z-B1 | 2.2 | 458 | 1 |
| 64 | A8-Z-B1 | 2.4 | 458 | 1 |
| 65 | A9-Z-B1 | 2.3 | 496 | 1 |
| 66 | A10-Z-B1 | 2.9 | 500 | 1 |
| 67 | A11-Z-B1 | 2.6 | 479 | 1 |
| 68 | A12-Z-B1 | 1.9 | 410 | 1 |
| 69 | A13-Z-B1 | 2.2 | 469 | 1 |
| 70 | A14-Z-B1 | 2.3 | 489 | 1 |
| 71 | A15-Z-B1 | 2.1 | 489 | 1 |
| 72 | A16-Z-B1 | 2.3 | 462 | 1 |
| 73 | A17-Z-B1 | 2.2 | 444 | 1 |
| 74 | A18-Z-B1 | 2.1 | 424 | 1 |
| 75 | A19-Z-B1 | 2.4 | 470 | 1 |
| 76 | A20-Z-B1 | 2.7 | 512 | 1 |
| 77 | A21-Z-B1 | 2.6 | 523 | 1 |
| 78 | A22-Z-B1 | 2.2 | 488 | 1 |
| 79 | A23-Z-B1 | 2.3 | 474 | 1 |
| 80 | A24-Z-B1 | 2.2 | 474 | 1 |
| 81 | A25-Z-B1 | 1.8 | 408 | 1 |
| 82 | A26-Z-B1 | 1.9 | 434 | 1 |
| 83 | A27-Z-B1 | 2.3 | 513 | 1 |
| 84 | A28-Z-B1 | 2.3 | 489 | 1 |
| 85 | A29-Z-B1 | 1.7 | 394 | 1 |
| 86 | A30-Z-B1 | 2.1 | 450 | 1 |
| 87 | A31-Z-B1 | 2.3 | 480 | 1 |
| 88 | A32-Z-B1 | 2.3 | 462 | 1 |
| 89 | A33-Z-B1 | 2.1 | 504 | 1 |
| 90 | A34-Z-B1 | 2.5 | 523 | 1 |
| 91 | A35-Z-B1 | 2.7 | 528 | 1 |
| 92 | A36-Z-B1 | 2.2 | 464 | 1 |
| 93 | A36-Z-B5 | 2.2 | 431 | 1 |
| 94 | A37-Z-B5 | 2.3 | 455 | 1 |
| 95 | A38-Z-B5 | 2.7 | 479 | 1 |
| 96 | A39-Z-B5 | 1.6 | 412 | 1 |
| 97 | A40-Z-B5 | 2.7 | 439 | 1 |
| 98 | A41-Z-B5 | 2.6 | 461 | 1 |
| 99 | A42-Z-B5 | 2.4 | 443 | 1 |
| 100 | A43-Z-B5 | 2.3 | 485 | 1 |
| 101 | A44-Z-B5 | 2.3 | 455 | 1 |
| 102 | A45-Z-B5 | 2.6 | 447 | 1 |
| 103 | A46-Z-B5 | 2.6 | 445 | 1 |
| 104 | A47-Z-B5 | 2.3 | 429 | 1 |
| 105 | A48-Z-B5 | 2.4 | 441 | 1 |
| 106 | A4-Z-B5 | 2.4 | 479 | 1 |
| 107 | A49-Z-B5 | 2.5 | 447 | 1 |
| 108 | A50-Z-B5 | 2.4 | 447 | 1 |
| 109 | A51-Z-B5 | 2.4 | 447 | 1 |
| 110 | A52-Z-B5 | 2.5 | 425 | 1 |
| 111 | A53-Z-B5 | 2.9 | 480 | 1 |
| 112 | A54-Z-B5 | 2.6 | 471 | 1 |
| 113 | A55-Z-B5 | 2.7 | 467 | 1 |
| 114 | A56-Z-B5 | 2.8 | 495 | 1 |
| 115 | A57-Z-B5 | 3.1 | 497 | 1 |
| 116 | A58-Z-B5 | 2.1 | 389 | 1 |
| 117 | A59-Z-B5 | 2.4 | 417 | 1 |
| 118 | A60-Z-B5 | 2.5 | 504 | 1 |
| 119 | A61-Z-B5 | 2.7 | 467 | 1 |
| 120 | A62-Z-B5 | 3.0 | 493 | 1 |
| 121 | A63-Z-B5 | 2.0 | 430 | 1 |
| 122 | A64-Z-B5 | 2.3 | 403 | 1 |
| 123 | A65-Z-B5 | 2.4 | 454 | 1 |
| 124 | A66-Z-B5 | 1.0 | 429 | 1 |
| 125 | A67-Z-B5 | 1.9 | 419 | 1 |
| 126 | A68-Z-B5 | 1.5 | 496 | 1 |
| 129 | A1-Z-B57 | 4.2 | 543 | 2 |
| 130 | A1-Z-B58 | 4.1 | 553 | 2 |
| 131 | A1-Z-B59 | 3.5 | 502 | 2 |
| 132 | A1-Z-B60 | 3.8 | 558 | 2 |
| 133 | A1-Z-B61 | 3.9 | 502 | 2 |
| 134 | A1-Z-B62 | 4.3 | 543 | 2 |
| 135 | A1-Z-B63 | 4.2 | 543 | 2 |
| 136 | A1-Z-B64 | 3.7 | 526 | 2 |
| 137 | A1-Z-B65 | 3.1 | 524 | 2 |
| 138 | A1-Z-B66 | 4.1 | 542 | 2 |
| 139 | A1-Z-B67 | 3.8 | 508 | 2 |
| 140 | A1-Z-B68 | 3.2 | 504 | 2 |
| 141 | A1-Z-B69 | 3.4 | 488 | 2 |
| 142 | A1-Z-B70 | 3.5 | 492 | 2 |
| 143 | A1-Z-B71 | 3.2 | 492 | 2 |
| 144 | A1-Z-B72 | 3.2 | 510 | 2 |
| 145 | A1-Z-B73 | 4.4 | 558 | 2 |
| 146 | A1-Z-B74 | 3.1 | 502 | 2 |
| 147 | A1-Z-B75 | 3.0 | 504 | 2 |
| 148 | A1-Z-B76 | 3.0 | 610 | 2 |
| 149 | A1-Z-B77 | 3.4 | 504 | 2 |
| 150 | A1-Z-B78 | 3.6 | 508 | 2 |
| 151 | A1-Z-B79 | 4.0 | 524 | 2 |
| 152 | A1-Z-B80 | 3.7 | 516 | 2 |
| 153 | A1-Z-B81 | 4.1 | 558 | 2 |
| 154 | A1-Z-B82 | 3.9 | 560 | 2 |
| 155 | A1-Z-B83 | 3.7 | 510 | 2 |
| 156 | A1-Z-B84 | 3.4 | 518 | 2 |
| 157 | A1-Z-B85 | 3.8 | 530 | 2 |
| 158 | A1-Z-B86 | 4.1 | 522 | 2 |
| 159 | A1-Z-B87 | 3.7 | 546 | 2 |
| 160 | A1-Z-B88 | 3.4 | 532 | 2 |
| 161 | A1-Z-B89 | 3.2 | 522 | 2 |
| 162 | A1-Z-B90 | 3.9 | 532 | 2 |
| 163 | A1-Z-B91 | 7.2 | 576 | 2 |
| 164 | A1-Z-B92 | 3.1 | 492 | 2 |
| 165 | A1-Z-B93 | 3.1 | 516 | 2 |
| 166 | A1-Z-B94 | 3.1 | 488 | 2 |
| 167 | A1-Z-B95 | 2.5 | 534 | 2 |
| 168 | A1-Z-B96 | 3.7 | 530 | 2 |
| 169 | A1-Z-B97 | 2.8 | 534 | 2 |
| 170 | A1-Z-B98 | 4.6 | 576 | 2 |
| 171 | A1-Z-B99 | 4.2 | 560 | 2 |
| 172 | A1-Z-B100 | 4.5 | 566 | 2 |
| 173 | A1-Z-B101 | 3.0 | 564 | 2 |
| 174 | A1-Z-B102 | 3.5 | 520 | 2 |
| 175 | A1-Z-B103 | 3.9 | 502 | 2 |
| 176 | A1-Z-B104 | 3.2 | 560 | 2 |
| 177 | A1-Z-B105 | 3.2 | 499 | 2 |
| 178 | A1-Z-B106 | 3.4 | 502 | 2 |
| 179 | A1-Z-B107 | 4.3 | 542 | 2 |
| 180 | A1-Z-B108 | 3.5 | 542 | 2 |
| 181 | A1-Z-B109 | 3.5 | 510 | 2 |
| 182 | A1-Z-B110 | 3.8 | 508 | 2 |
| 183 | A1-Z-B111 | 2.2 | 576 | 1 |
| 184 | A1-Z-B112 | 2.5 | 510 | 1 |
| 187 | A51-Z-B1 | 2.3 | 480 | 1 |
| 188 | A52-Z-B1 | 2.4 | 458 | 1 |
| 189 | A53-Z-B1 | 2.8 | 513 | 1 |
| 190 | A55-Z-B1 | 2.7 | 500 | 1 |
| 191 | A56-Z-B1 | 2.7 | 528 | 1 |
| 192 | A57-Z-B1 | 3.0 | 530 | 1 |
| 193 | A58-Z-B1 | 2.0 | 422 | 1 |

TABLE IV-continued

| N° | Code | r.t. (min) | [M + H]+ | HPLC Method |
|---|---|---|---|---|
| 194 | A59-Z-B1 | 2.3 | 450 | 1 |
| 195 | A60-Z-B1 | 2.4 | 537 | 1 |
| 196 | A61-Z-B1 | 2.6 | 500 | 1 |
| 197 | A62-Z-B1 | 2.2 | 526 | 1 |
| 198 | A63-Z-B1 | 2.0 | 463 | 1 |
| 199 | A64-Z-B1 | 2.2 | 436 | 1 |
| 200 | A66-Z-B1 | 2.3 | 462 | 1 |
| 201 | A67-Z-B1 | 1.8 | 452 | 1 |
| 202 | A68-Z-B1 | 2.5 | 529 | 1 |
| 203 | A7-Z-B5 | 2.3 | 425 | 1 |
| 204 | A8-Z-B5 | 2.5 | 425 | 1 |
| 205 | A9-Z-B5 | 2.4 | 463 | 1 |
| 206 | A10-Z-B5 | 3.0 | 467 | 1 |
| 207 | A11-Z-B5 | 2.6 | 445 | 1 |
| 208 | A12-Z-B5 | 2.0 | 377 | 1 |
| 209 | A13-Z-B5 | 2.3 | 436 | 1 |
| 210 | A14-Z-B5 | 2.4 | 456 | 1 |
| 211 | A15-Z-B5 | 2.2 | 456 | 1 |
| 212 | A16-Z-B5 | 2.4 | 429 | 1 |
| 213 | A70-Z-B5 | 1.5 | 349 | 1 |
| 214 | A17-Z-B5 | 2.3 | 411 | 1 |
| 215 | A18-Z-B5 | 2.2 | 391 | 1 |
| 216 | A19-Z-B5 | 2.5 | 437 | 1 |
| 217 | A20-Z-B5 | 2.8 | 479 | 1 |
| 218 | A21-Z-B5 | 2.7 | 490 | 1 |
| 219 | A22-Z-B5 | 2.3 | 455 | 1 |
| 220 | A23-Z-B5 | 2.4 | 441 | 1 |
| 221 | A24-Z-B5 | 2.3 | 441 | 1 |
| 222 | A25-Z-B5 | 1.9 | 375 | 1 |
| 223 | A26-Z-B5 | 2.0 | 401 | 1 |
| 224 | A27-Z-B5 | 2.4 | 479 | 1 |
| 225 | A28-Z-B5 | 2.4 | 456 | 1 |
| 226 | A29-Z-B5 | 1.8 | 361 | 1 |
| 227 | A30-Z-B5 | 2.2 | 417 | 1 |
| 228 | A31-Z-B5 | 2.4 | 447 | 1 |
| 229 | A32-Z-B5 | 2.4 | 429 | 1 |
| 230 | A33-Z-B5 | 2.2 | 471 | 1 |
| 231 | A34-Z-B5 | 2.7 | 490 | 1 |
| 232 | A35-Z-B5 | 2.8 | 495 | 1 |
| 259 | A1-Z-B113 | 4.1 | 546 | 2 |
| 260 | A1-Z-B114 | 3.3 | 480 | 2 |
| 261 | A1-Z-B115 | 2.4 | 493 | 2 |
| 262 | A1-Z-B116 | 3.1 | 499 | 2 |
| 263 | A1-Z-B117 | 3.1 | 480 | 2 |
| 264 | A1-Z-B118 | 4.3 | 543 | 2 |
| 265 | A1-Z-B119 | 3.3 | 568 | 2 |
| 266 | A1-Z-B120 | 2.8 | 509 | 2 |
| 267 | A1-Z-B121 | 3.0 | 526 | 2 |
| 268 | A1-Z-B122 | 3.1 | 571 | 2 |
| 269 | A1-Z-B123 | 3.8 | 578 | 2 |
| 270 | A1-Z-B124 | 3.5 | 587 | 2 |
| 271 | A1-Z-B125 | 3.6 | 577 | 2 |
| 272 | A1-Z-B126 | 3.0 | 621 | 2 |
| 273 | A1-Z-B127 | 3.8 | 579 | 2 |
| 274 | A1-Z-B128 | 4.2 | 626 | 2 |

The invention claimed is:

1. A method for treating a disease selected from the group consisting of ovarian cancer, breast cancer, colon cancer, lung cancer, small cell lung cancer, pancreatic cancer, cervical cancer, prostate cancer, skin carcinoma, squamous cell carcinoma, hematopoietic tumors of lymphoid lineage, leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma, Burkett's lymphoma, hematopoietic tumors of myeloid lineage, acute myelogenous leukemia, chronic myelogenous leukemia, myelodysplastic syndrome, promyelocytic leukemia melanoma and osteosarcoma which comprises administering to a mammal in need thereof an effective amount of a compound of formula (I):

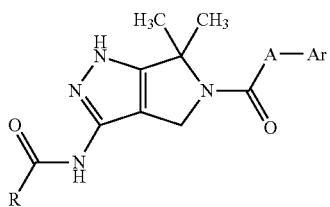

wherein:

R is hydrogen or an optionally further substituted group selected from: saturated or unsaturated, straight or branched $C_1$-$C_6$ alkyl, $C_3$-$C_6$ cycloalkyl, heterocyclyl and aryl;

A is $CH_2$ or NH;

Ar is an optionally substituted aryl, provided that when A is $CH_2$ and Ar is phenyl then R is other than 3-bromophenyl, 4-fluorophenyl, 4-tert-butylphenyl, cyclopropyl or 2-naphthyl and when A is $CH_2$ and Ar is thiophene then R is other than 3-bromophenyl, 4-fluorophenyl, 4-tert-butylphenyl, cyclopropyl, 2-naphthyl or benzyl; and isomers, tautomers, metabolites, prodrugs, carriers, N-oxides and pharmaceutically acceptable salts thereof.

2. The method according to claim 1 which provides tumor angiogenesis and metastasis inhibition as well as treatment of organ transplant rejection and host versus graft disease.

3. The method according to claim 1 further comprising subjecting the mammal in need thereof to a radiation therapy or chemotherapy regimen in combination with at least one cytostatic or cytotoxic agent.

4. The method according to claim 1 wherein the mammal in need thereof is a human.

* * * * *

SEQUENCE LISTING

<160> NUMBER OF SEQ ID NOS: 2

<210> SEQ ID NO 1
<211> LENGTH: 82
<212> TYPE: DNA
<213> ORGANISM: Artificial
<220> FEATURE:
<223> OTHER INFORMATION: forward primer

<400> SEQUENCE: 1

```
ggggacaagt ttgtacaaaa aagcaggctt attcgaaaac ctgtattttc agggccctag    60
tgctgcagtg actgcaggga ag                                             82
```

<210> SEQ ID NO 2
<211> LENGTH: 60
<212> TYPE: DNA
<213> ORGANISM: Artificial
<220> FEATURE:
<223> OTHER INFORMATION: reverse primer

<400> SEQUENCE: 2

```
ggggaccact ttgtacaaga aagctgggtt tcactatttta ttgaggactg tgaggggctt    60
```